United States Patent [19]

Sendai et al.

[11] Patent Number: 5,393,751
[45] Date of Patent: Feb. 28, 1995

[54] TRICYCLIC CARBAPENEM COMPOUNDS

[75] Inventors: Michiyuki Sendai, Suita; Tetsuo Miwa, Kobe, both of Japan

[73] Assignee: Takeda Chemical Industries, Ltd., Osaka, Japan

[21] Appl. No.: 595,287

[22] Filed: Oct. 10, 1990

[30] Foreign Application Priority Data

Oct. 11, 1989 [JP] Japan .................. 1-264345
Jul. 3, 1990 [JP] Japan .................. 2-177118

[51] Int. Cl.$^6$ ............... C07D 487/00; A01N 43/00; A61K 31/395
[52] U.S. Cl. ............................ 514/210; 540/302
[58] Field of Search ................. 540/302; 514/210

[56] References Cited

U.S. PATENT DOCUMENTS 4,600,713  7/1986  Christensen et al. ............... 540/302

OTHER PUBLICATIONS

Tetrahedron Letters vol. 22, No. 50, 5027–5030 (1981).

Primary Examiner—Johann Richter
Assistant Examiner—Rebecca Cook
Attorney, Agent, or Firm—Foley & Lardner

[57] ABSTRACT

A compound of the formula

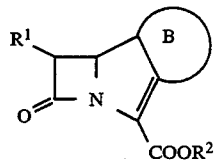

wherein $R^1$ is a hydrogen atom or a hydrocarbon group which may be substituted; $COOR^2$ represents a carboxy group which may be esterified; and ring B is a cyclic group which may be substituted or a pharmaceutically acceptable salt thereof are useful as an antibacterial agent.

7 Claims, No Drawings

TRICYCLIC CARBAPENEM COMPOUNDS

This invention relates to a novel tricyclic carbapenem compound or a salt thereof. The tricyclic carbapenem compound and a salt thereof are used as an antibacterial agent.

A large number of reports are available on carbapenem antibiotics represented by thienamycin cf. Robert B. Morin & Marvin Gorman, Chemistry and Biology of β-Lactam Antibiotics 2, 227, Academic Press Inc., 1982). With regard to tricyclic carbapenem compounds, compounds of the following formula are described in Tetrahedron Letters 22, 5027 (1981), but the compound of the present invention is a novel compound which is structurally differing much from any of these known compounds.

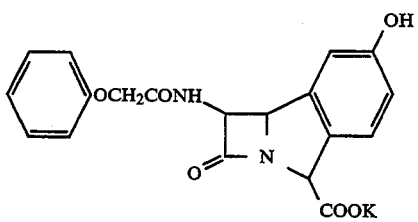

Carbapenem compounds generally have excellent antibacterial activity but have drawbacks in terms of chemical stability and stability against renal dehydropeptidase-I (DHP-I). The development of a carbapenem compound having high antibacterial activity, stability in vivo and good pharmacokinetical property has, therefore, been keenly demanded.

The object of the present invention is to provide such a carbapenem compound.

The present inventors explored various carbapenem compounds for accomplishing the above-mentioned object and have succeeded in creating a group of compounds having a completely novel structure and, at the same time, found that these compounds exhibit excellent antibacterial activity. The present invention has accordingly been conceived and accomplished.

The present invention, as such, is directed to a tricyclic carbapenem compound of the formula (I)

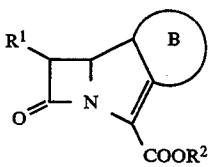

(I)

(wherein $R^1$ is a hydrogen atom or a hydrocarbon group which may optionally be substituted; $COOR^2$ represents a carboxy group which may optionally be esterified; and ring B is a cyclic group which may optionally be substituted) [hereinafter referred to sometimes as compound (I)]or a salt thereof; a process for production thereof; and an antibacterial composition containing said compound or salt.

The compound (I) and salt of the invention exhibit remarkably high antibacterial activity against a broad spectrum of pathogenic bacteria including both gram-positive and gram-negative bacteria.

Referring to the above formula (I), the hydrocabon group which may optionally be substituted, as denoted by $R^1$, includes substituted or unsubstituted lower alkyl, lower alkenyl, lower alkynyl, cycloalkyl, aralkyl and aryl groups. The lower alkyl group is a straight-chain or branched alkyl group of 1 to 6 carbon atoms, such as methyl, ethyl, n-propyl, isopropyl, n-butyl, isobutyl, sec-butyl, tert-butyl, n-pentyl, n-hexyl and so on. The lower alkenyl group is a straight-chain or branched alkenyl group of 3 to 6 carbon atoms, such as, propenyl, butenyl, pentenyl and so on. The lower alkynyl group is a straight-chain or branched alkynyl group of 3 to 6 carbon atoms, such as propynyl, butynyl, pentynyl and so on. The cycloalkyl group is a cycloalkyl group of 3 to 6 carbon atoms, such as cyclopropyl, cyclobutyl, cyclopentyl, cyclohexyl and so on. The aralkyl group is an aralkyl group of 7 to 10 carbon atoms, such as benzyl and other phenylalkyl groups. The aryl group is an aryl group of 6 to 10 carbon atoms, such as phenyl and naphthyl. These lower alkyl, lower alkenyl, lower alkynyl, cycloalkyl, aralkyl and aryl groups may respectively be substituted by 1 to 3 substituents such as cyano, amino, mono- or di($C_1$–$C_4$)alkyl(e.g. methyl, ethyl, propyl, isopropyl, butyl, etc.)amino, hydroxy, ($C_1$–$C_4$)alkyloxy, carbamoyloxy, ($C_1$–$C_4$)alkylthio, ($C_1$–$C_4$)alkylsulfonyl, halogen (e.g. fluorine, chlorine, bromine, etc.), sulfamoyl, ($C_1$–$C_4$)alkoxycarbonyl (e.g. methoxycarbonyl, ethoxycarbonyl, propoxycarbonyl, butoxycarbonyl, etc.), sulfoxy and so on.

Preferred species of $R^1$ are methyl, ethyl, propyl, hydroxymethyl, 1-hydroxyethyl, 1-hydroxypropyl, 1-hydroxy-1-methylethyl, fluoromethyl, 1- or 2-fluoroethyl, 1,1-difluoroethyl, 1-methyl-1-sulfoxyethyl, 1-aminoethyl and so on.

Referring, further, to the above formula (I), the ester residue $R^2$ of said esterified carboxy group $COOR^2$ includes those residues which are commonly found in the chemistry of β-lactams such as cephalosporins, for example the groups which form easily biologically hydrolyzed esters at the 4-position of cephalosporins (the esters capable of providing the so-called prodrugs) and those groups which are commonly used as carboxylic acid ester residues in the field of medicaments. Thus, by way of example, groups of the formula

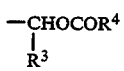

(wherein $R^3$ is hydrogen, alkyl, cycloalkyl or cycloalkylalkyl; $R^4$ is hydrogen, alkyl, cycloalkyl, alkoxy, cycloalkyloxy, cycloalkylalkyl, alkenyloxy or phenyl), phthalidyl, (2-oxo-5-methyl-1,3-dioxol-4-yl)methyl, alkoxyalkyl, alkylthioalkyl, tert-butyl, 2,2,2-tri-chloroethyl, benzyl, p-methoxybenzyl, p-nitrobenzyl, o-nitrobenzyl, phenethyl, bis(methoxyphenyl)methyl, 3,4-dimethoxybenzyl, benzhydryl, trityl, trimethylsilyl, 2-trimethylsilylethyl, allyl, etc. may be mentioned.

The alkyl group mentioned for $R^3$ and $R^4$ in the above formula and the alkyl moiety of the alkoxyalkyl and alkylthioalkyl groups, among said ester residues, include, among others, straight-chain or branched ($C_1$–$C_6$) alkyl groups (e.g. methyl, ethyl, propyl, isopropyl, butyl, 2,2-dimethylpropyl, etc.). The cycloalkyl group and the cycloalkyl moiety of the cycloalkyloxy or cycloalkylalkyl group includes, among others, ($C_3$–$C_7$)cycloalkyl groups (e.g. cyclopropyl, cyclobutyl, cyclopentyl, cyclohexyl, cycloheptyl, etc.). The alkoxy group $R^4$ and the alkoxy moiety of the alkoxyalkyl group, among said ester residues, include, among others, straight-chain or branched $C_{1-10}$ alkoxy groups (e.g. methoxy, ethoxy, propoxy, isopropoxy, butoxy, hexyloxy, decyloxy, etc.). The alkenyloxy group represented by $R^4$ includes, among others, straight-chain or branched $C_{2-7}$ alkenyloxy groups (e.g. allyloxy etc.).

Particularly preferred species of the ester residue $R^2$ are groups which give biologically labile ester derivatives and are suited for oral administration, such as acetoxymethyl, 1-acetoxyethyl, 1-acetoxypropyl, pivaloyloxymethyl, 1-isopropyloxycarbonyloxyethyl, 1-cyclohexyloxycarbonyloxyethyl, phthalidyl, (2-oxo-5-methyl-1,3-dioxol-4-yl)methyl and so on.

The cyclic group which may optionally be substituted, as indicated by ring B, is a cyclic group formed in combination with the carbon atoms in the 1- and 2-positions of a carbapenem compound of the formula:

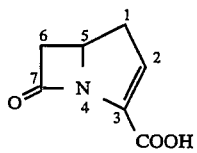

Among species of such cyclic group are saturated or unsaturated carbocyclic groups and saturated or unsaturated heterocyclic groups containing 1 to 4 heteroatoms selected from among N, S (which may be in the form of mono- or dioxide), O, etc. These carbocyclic or heterocyclic groups may be condensed groups formed by fusion of such groups to other carbocyclic or heterocyclic groups.

Ring B is preferably 5- to 8-membered ring. Ring B may be a ring formed by A taken together with the 1- and 2-positions of the carbapenem nucleus, for example the ring which can be written as

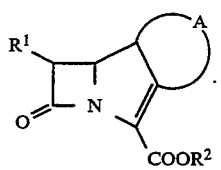

(I')

In the above formula, A is a lower alkylene or lower alkenylene group which may be interrupted by oxygen, sulfur (which may be in the form of mono- or dioxide), nitrogen, a divalent cyclic hydrocarbon group, a divalent heterocyclic group, carbonyl, or carbonimidoyl. Thus, ring B is preferably a 5- to 8-membered ring which may be interrupted by oxygen, sulfur (which may be in the form of mono- or dioxide), nitrogen, a divalent cyclic hydrocarbon group, a divalent heterocyclic group, carbonyl, or carbonimidoyl and may be substituted. Examples of the lower alkylene group A are vinylene, trimethylene, tetramethylene, pentamethylene and hexamethylene, while examples of the lower alkenylene group A include ethenylene, propenylene, butenylene, pentenylene and hexenylene.

The cyclic hydrocarbon of the divalent cyclic hydrocarbon group as a constituent of A in the above formula (I') includes, among others, cyclic saturated hydrocarbons such as cyclopropane, cyclopentane, cyclohexane, etc., cyclic unsaturated hydrocarbons such as cyclopentene, cyclohexene, etc., and aromatic hydrocarbons such as benzene, naphthalene and so on. The heterocycle of said divalent heterocyclic group is preferably a 4- to 6-membered heterocycle containing 1 to 4 heteroatoms such as nitrogen, oxygen and sulfur and includes, among others, azetidine, furan, pyrrole, pyrrolidine, thiophene, thiazole, isothiazole, thiazoline, oxazole, isooxazole, oxazoline, oxazolidine, pyrazole, pyrazoline, imidazole, imidazoline, thiadiazole, triazole, tetrazole, pyridine, pyrimidine, pyridazine, pyran, morpholine, piperazine, piperidine and so on.

As ring B, particularly preferred are 5- or 7-membered heterocycles containing one to two hetero atom(s) of N, O, S as the ring constituent element and 5- or 7-membered carbocycle, which are exemplified by tetrahydrofuran, pyrrolidine, oxazolidine, thiazolidine, imidazolidine, pyrazolidine, tetrahydropyran, dihydropyran, tetrahydrothiopyran, dihydrothiopyran, dioxane, dithiane, oxathiane, piperidine, piperazine, hexahydropyrimidine, hexahydropyridazine, tetrahydrooxazine, tetrahydrothiazine, oxepane, thiepane, perhydroazepine, perhydrodiazepine, dioxepane, dihydrodioxepine, dithiepane, oxathiepane, perhydrothiazepine, perhydrooxazepine, cyclopentane, cyclopentene, cyclohexane, cyclohexene, cycloheptane and cycloheptene.

The carbon chain, nitrogen atom, divalent cyclic hydrocarbon group, divalent heterocyclic group or carbonimidoyl group in such lower alkylene or lower alkenylene group may be substituted by such substituent groups as, for example, $C_{1-6}$ alkyl, $C_{2-6}$ alkenyl (e.g. vinyl, butenyl, propenyl, etc.), $C_{6-10}$ aryl (e.g. phenyl and naphthyl), $C_{7-12}$ aralkyl, $C_{3-6}$ cycloalkyl (e.g. cyclopropyl, cyclobutyl, cyclopentyl, etc.), the 4- to 6-membered heterocycles mentioned above, cyano, amino, mono- or di($C_{1-4}$alkyl)amino, hydroxy, $C_{1-4}$ alkyloxy, carbamoyloxy, $C_{1-4}$ alkylthio, $C_{1-4}$ alkylsulfonyl, halogen (e.g. fluorine, chlorine, bromine, etc.), sulfamoyl, $C_{1-4}$ alkoxycarbonyl, imino, $C_{1-4}$ alkylimino, carbamoyl, mono- or di($C_{1-4}$)alkylcarbamoyl and so on. The lower alkyl group as the $C_{1-6}$ alkyl which may substitute said lower alkylene or lower alkenylene group may be further substituted by suitable substituents such as the 4- to 6-membered heterocycles mentioned above, cyano, amino, mono- or di($C_{1-4}$alkyl)amino, hydroxy, $C_{1-4}$ alkyloxy, carbamoyloxy, $C_{1-4}$ alkylthio, $C_4$ alkylsulfonyl, halogen (e.g. fluorine, chlorine, bromine, etc.), sulfamoyl, $C_{1-4}$ alkoxycarbonyl, imino, $C_{1-4}$ alkylimino, carbamoyl, mono- or di($C_4$alkyl)carbamoyl and so on. The number of such substituents is preferably 1 to 3, and where a plurality of substituents are present, these substituents may be the same or different.

When ring B is a nitrogen-containing heterocycle or has an amino group or a nitrogen-containing heterocycle as the substituent, they may be substituted by lower alkyl groups to form a quaternary ammonium salt.

The preferred salt of compound (I) is a pharmaceutically acceptable salt. Examples of such pharmaceutically acceptable salt are salts with inorganic bases, salts with organic bases, salts with inorganic acids, salts with organic acids, and salts with basic or acidic amino acids. The inorganic bases capable of forming such salts include alkali metals (e.g. sodium, potassium, etc.), alkaline earth metals (e.g. calcium, magnesium, etc.) and so on. The organic bases capable of forming said salts include trimethylamine, triethylamine, pyridine, picoline, N,N'-dibenzylethylenediamine, ethanolamine, diethanolamine, tris(hydroxymethyl)aminomethane, dicyclohexylamine and so on. The inorganic acids include, among others, hydrochloric acid, hydrobromic acid, sulfuric acid, nitric acid and phosphoric acid. The organic acids include, among others, formic acid, acetic acid, trifluoroacetic acid, oxalic acid, tartaric acid, fumaric acid, maleic acid, methanesulfonic acid, benzenesulfonic acid and p-toluenesulfonic acid. The basic or acidic amino acids include, among others, arginine, lysine, ornithine, aspartic acid and glutamic acid. Of these salts, salts with bases (i.e. salts with inorganic bases, salts with organic bases and salts with basic amino acids) are salts formed with the carboxyl group of compound (I) or those with acid groups, such as carboxyl, which may be present on R or ring B, and salts with acids (i.e. salts with inorganic acids, salts with organic acids and salts with acidic amino acids) are salts formed with the substituent amino group of compound (I) or salts with basic groups, such as amino, which may be present on $R^1$ or ring B.

Compound (I), inclusive of its salt, is a useful antibiotic which exhibits antibacterial activity against gram-positive and gram-negative bacteria inclusive of clinical strains and can be used as drugs for man and domestic animals. Thus, it can be safely used as an antibacterial agent for the treatment and prevention of infections due to various bacteria.

The compound (I), inclusive of its salt, according to the present invention can be incorporated in animal diets as a bactericide for prevention of putrefaction of feedstuffs. Moreover, it can also be used as a disinfectant for eliminating harmful bacteria from medical or dental equipment and devices.

The compound (I) of the invention, inclusive of its salt, can be put to use as it is or in combination with a pharmaceutically acceptable carrier, and, if desired, other active substances and, if necessary, together with auxiliary agents such as stabilizers, dispersants, etc., in a variety of preparations such as capsules, tablets, solutions, suspensions, emulsions and so on. These preparations can be administered parenterally (for example, intravenously or intramuscularly) or orally.

Parenteral products can be supplied in ampules or in containers with an added preservative. Such products may be suspensions, solutions or emulsions in oily vehicles or aqueous solvents, and may contain the known auxiliary agents such as suspending agents, stabilizers and/or dispersants. The compound (I) or a salt thereof can also be supplied as a powder or the like which is to be dissolved in an appropriate solvent, such as sterile pyrogen-free water, just before application.

The compound (I) of the invention, inclusive of its salt, can be admixed with a suitable binder such as syrup, gum arabic, gelatin, sorbitol, gum tragacanth, polyvinylpyrrolidone, etc., a filler such as lactose, sucrose, corn starch, calcium phosphate, sorbitol, glycine, etc., a lubricant such as magnesium stearate, talc, polyethylene glycol, silica, etc., a disintegrating agent such as potato starch etc., and/or a wetting agent such as sodium laurylsulfate etc. and, then, processed into oral dosage forms such as tablets, capsules, granules, powders and so on. The tablets, granules, etc. can be film-coated by the per se known procedures. Liquid preparations such as aqueous or oil suspensions, solutions, emulsions, syrups, elixirs, etc. can also be mentioned as examples of preparations for oral administration. In these preparations, there may be incorporated other known ingredients such as antioxidants, preservatives, binders, wetting agents, lubricants, thickeners, corrigents or flavors, and so on. Furthermore, these compositions may be admixed with other active ingredients (for example, β-lactam antibiotics) to provide a pharmaceutical preparation showing a still broader antibacterial spectrum.

Compound (I) and its salt can be used as therapeutic or prophylatic agents for bacterial infections, for example respiratory tract infection, urinary tract infection, suppurative disease, biliary tract infection, intestinal infection, gyneco-obstetric infection, otorhinological infection and surgical infection in man and other mammals. The daily dosage of compound (I) or its salt depends on the patient's condition and body weight, the route of administration and other factors. Generally speaking, for parenteral administration, the daily dose for adults may be about 0.5 to 80 mg as active ingredient (compound (I) or salt thereof) per kg body weight and preferably about 1 to 40 mg on the same basis, and this dose can be advantageously administered intravenously or intramuscularly in 1 to 4 divided doses a day. The preferred oral dosage for adults is about 1 to 100 mg as active ingredient (compound (I) or salt thereof) per kg body weight.

The compound (I) of the invention can be produced by a known method or any method analogous thereto. For example, the compound of formula (I) can be produced by way of illustration, by cyclizing a compound of formula

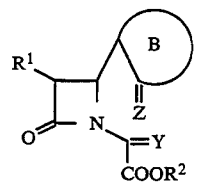

(II)

wherein $R^1$, $R^2$ and B have the meanings respectively defined hereinbefore; $=Y$ and $=Z$ respectively mean functional groups which may react with each other to form a double bond. With regard to the functional groups $=Y$ and $=Z$ and the reaction involved, those groups and reactions which are per se known can be selectively employed [Annual Reports in Organic Synthesis, 1975–1989, Academic Press, Inc., San Diego] and [F. A. Carey and R. J. Sundberg, Advanced Organic Chemistry Second Edition, Plenum Press, New York and London, 1983].

Thus, a Witrig reaction (Wittig-Horner-Emmons reaction), Peterson reaction, aldol reaction involving dehydration, and McMurray reaction using a low valence metal, inter alia, can be employed. Preferred is a Wittig reaction using $=O$, $=S$, $=Se$, $=P(R^5)_3$,

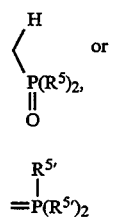

(where $R^5$ and $R^{5'}$ mean a lower alkyloxy group, a lower alkyl group or an aryl group) for $=Y$ and $=Z$. Specifically, the following process, for instance, can be employed.

Production process 1

The compound (I') can be produced by heating a compound of formula (II'):

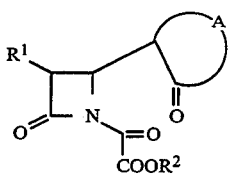
(II')

wherein $R^1$ and $R^2$ and A are respectively as defined hereinbefore (hereinafter referred to briefly as compound (II')) and a compound of formula (IV) or (IV'):

(IV)

(IV')

wherein $R^5$ and $R^{5'}$ are as defined above, if necessary followed by eliminating the protective group or groups. The reaction can be generally conducted by heating in an inert solvent.

When the structure of compound (II') includes reactive groups such as amine, hydroxy and/or carboxy, these groups may be protected by the protective groups which are mentioned hereinafter.

Referring to $R^5$ and $R^{5'}$, the lower alkyloxy group may for example be methoxy, ethoxy, propoxy, butoxy or the like; the lower alkyl group may for example be methyl, ethyl, propyl, butyl, pentyl or the like; and the aryl group may for example be phenyl or the like.

The inert solvent to be used in conducting this reaction is not critical in kind but aromatic hydrocarbons such as benzene, toluene, xylene, etc., ethers such as dioxane, diethoxyethane, tetrahydrofuran, etc. and halogenated hydrocarbons such as dichloromethane, chloroform, etc. are preferred.

The proportion of compound (IV) or (IV') are at least 2 mol equivalents and preferably 2 to 10 mol equivalents based on compound (II'). Though the proper reaction temperature depends on starting compounds (II'), (IV) and (IV'), the kind of solvent, etc., it is generally 20° to 160° C. and preferably about 80° to 140° C. The reaction time is generally about 30 minutes to 100 hours and preferably about 1 to 72 hours.

Production process 2

The compound (I') can be produced by subjecting a compound of formula (II'')

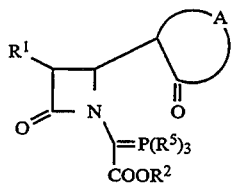
(II'')

wherein $R^1$, $R^2$, $R^5$ and A are respectively as defined hereinbefore to cyclization reaction, if necessary followed by eliminating the protective group or groups. The cyclization reaction can be conducted in an inert solvent.

When the structure of compound (II'') includes reactive groups such as amino, hydroxy and/or carboxy, these groups may be protected by the protective groups mentioned hereinafter.

This cyclization reaction is carried out in an inert solvent at a temperature within the range of about 0° to 160° C. and preferably at a temperature between about 30° and 140° C. Among preferred examples of such inert solvent are the aforementioned aromatic hydrocarbons, ethers and halogenated hydrocarbons. While the reaction time varies with the kind of compound (II'') and the reaction temperature, it is generally about 30 minutes to 100 hours and more usually about 1 to 72 hours.

Referring to formula (II') or (II''), where an amino group is present in the substituent $R^1$, $R^2$ or A, such amino group is preferably protected by a protective group. Such amino-protecting group can be selected from a broad range of groups which are used in the fields of β-lactams and peptides, for instance. Preferred are formyl, chloroacetyl, phenylacetyl, phenoxyacetyl, tert-butoxycarbonyl, benzyloxycarbonyl, p-methoxybenzyloxycarbonyl, p-nitrobenzyloxycarbonyl, 2-trimethylsilylethoxycarbonyl, 2,2,2-trichloroethoxycarbonyl, trityl, allyloxycarbonyl and so on. Where a hydroxy group is present, this hydroxy group is preferably protected. The protective group which can be used for such protection of the hydroxy group includes, among others, chloroacetyl, benzyl, p-nitrobenzyl, o-nitrobenzyl, methylthiomethyl, trimethylsilyl, tert-butyldimethylsilyl, tert-butyldiphenylsilyl, 2-tetrahydropyranyl, 4-methoxy-4-tetrahydropyranyl, p-nitrobenzyloxycarbonyl, o-nitrobenzyloxycarbonyl, allyloxycarbonyl and so on. Where a carboxy group is present, such carboxy group is preferably protected. The protective group which can be used here includes, among others, benzyl, benzhydryl, trityl, p-methoxybenzyl, p-nitrobenzyl, o-nitrobenzyl, phenethyl, 2-trimethylsilylethyl, bis(p-methoxyphenyl)methyl, tert-butyl, allyl and so on.

In the case of the compounds of the formula (II)

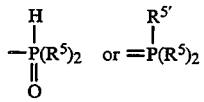

and the compounds of the formula (II) wherein =Z is =S, =P($R^5$)$_3$ or =Se, the compounds (I') can be produced from these starting compounds in accordance with the aforementioned process.

The starting compound (II) to be used in the present invention can be produced by the per se known processes or any processes analogous thereto. For example, compounds (II') and (II'') can be produced by the process illustrated in the reaction schema given below or any process analogous thereto.

(Scheme 1)

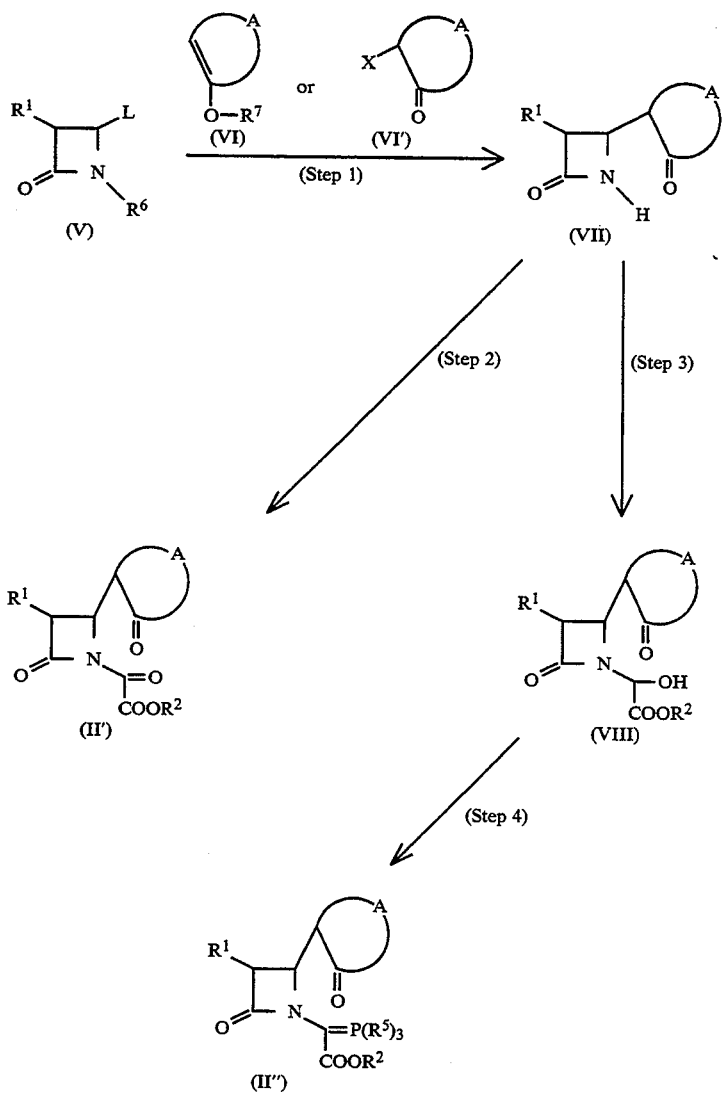

Step 1

The reaction between a compound of formula (V)

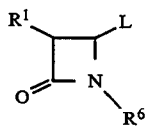

wherein $R^1$ is as defined hereinbefore; $R^6$ is a hydrogen atom or an easily removable protective group; L is acetoxy, benzoyloxy, arylsulfonyl or lower alkylsulfonyl and a compound of formula (VI)

wherein A is as defined hereinbefore; $R^7$ is an easily removable enol-protecting group, can be carried out in the presence of a Lewis acid catalyst selected from among trimethylsilyl trifluoromethanesulfonate, boron trifluoride ether complex, zinc iodide, zinc bromide, zinc chloride, magnesium chloride, titanium tetrachloride, titanium trichloride, stannous chloride, stannic chloride, stannous triflate, diethylboron triflate, ferric chloride, aluminum chloride, etc. and, if necessary, in the presence of a nitrogen-containing base such as diisopropylethylamine, triethylamine, trimethylamine, pyridine, etc. in an aprotic solvent such as hexane, benzene, toluene, dichloromethane, chloroform, dioxane, tetrahydrofuran, acetonitrile, ether and so on. When compound (VI) is 2-[(trimethylsilyl)oxy]-1,3-cyclohexadiene, a particularly preferred Lewis acid catalyst is a mixture of stannous chloride and chlorotrimethylsilane. When compound (VI) is 4-[(trimethylsilyl)oxy]-5,6-dihydro-2H-pyran, zinc bromide is a particularly preferred Lewis acid catalyst. The reaction temperature is $-100°$ to $80°$ C.

Referring to formula (V), the easily removable protective group $R^6$ may be an organosilyl group such as trimethylsilyl, t-butyldimethylsilyl, phenyldimethylsilyl, etc., benzyl, p-nitrobenzyl, p-methoxybenzyl, benzhydryl, 2,4-dimethoxybenzyl or the like.

Referring to formula (VI), the easily removable enol-protecting group represented by $R^7$ can be selected from among those used commonly in the so-called aldol reaction (Teruaki Mukaiyama: Organic Reactions, Vol. 28, John Wiley & Sons Inc., New York, 1982). Thus, for example, trimethylsilyl, t-butyldimethylsilyl, di-n-butylboryl, dimethylboryl, diethylboryl, lithium and a group of the formula $MgQ$, $ZnQ$, $AlQ_2$, $BQ_2$, $SnQ$, $ZrQ$, $Zr(cp)_2Q$ (wherein Q is F, Cl Br or triflate; cp is cyclopentadienyl) may be mentioned by way of illustration.

The reaction between compound (V) and compound (VI') of the formula

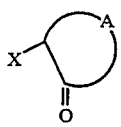

wherein A is as defined hereinbefore; X is a halogen atom can be carried out in the presence of a metal dust or a low valence metal salt, e.g. zinc dust, in an aprotic solvent such as diethyl ether, tetrahydrofuran, dioxane, benzene, hexane, cyclohexane, N,N-dimethylformamide, N,N-dimethylacetamide or the like. The reaction temperature is preferably in the range of 0° to 100° C.

After the reaction of compound (V) with compound (VI) or (VI'), the protective group is eliminated as necessary to give compound (VII).

Step 2

The compound (II') can be produced by reacting a compound of general formula (VII) with a reactive derivative, e.g. an organic acid ester or an acid halide, of an organic acid of the formula $R^2OCO-COOH$ at a temperature of $-100°$ to 80° C. When the acid halide is employed, the reaction is carried out preferably in the presence of an acid acceptor such as an aliphatic tertiary amine, an aromatic amine or an alkali metal or alkaline earth metal carbonate or hydrogen carbonate. The solvent is preferably one of the aforementioned ethers and hydrogenated hydrocarbons.

Step 3

The compound of general formula (VIII) can be produced by reacting a compound of general formula (VII) with glyoxylic acid or a suitable derivative thereof which can be represented by the formula $ROCO-CHO$, such as the hydrate or hemihydrate or the hemiacetal with a lower alkanol (e.g. methanol or ethanol). This reaction is carried out at room temperature or under heating. When the hydrate of glyoxylic acid is employed, the reaction is carried out with the byproduct water being removed azeotropically or with the aid of a suitable dehydrating agent. Preferably, this reaction is conducted in an inert solvent.

Step 4

The compound of general formula (II'') can be produced by treating a compound of general formula (VIII) with a thionyl halide (e.g. thionyl chloride) in an appropriate solvent (e.g. dioxane or tetrahydrofuran) in the presence of an organic base (e.g. an aliphatic tertiary amine such as triethylamine, etc., pyridine, picoline, lutidine, etc.), if desired under cooling (e.g. at about $-30°$ to 30° C.) to give the halide and reacting it with a trivalent phosphorus compound of general formula (IV) in the presence of said organic base. This reaction is preferably carried out in an inert solvent (e.g. the aforementioned ethers and halogenated hydrocarbons or esters such as ethyl acetate, methyl acetate, etc.) at $-10°$ to 100° C.

The compounds (II) other than (II') and (II'') can also be produced by a method analogous to the above-mentioned method or by the method described in Tetrahedron Letters 25, 2793 (1984). Furthermore, among various compounds of the formula (I), the compound (I) wherein ring B may optionally be substituted and contain 1 to 3 hetero-atoms selected from the class consisting of O, S and N as ring members can be produced by cyclizing a compound of formula (III) or (III')

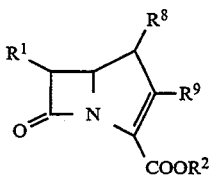 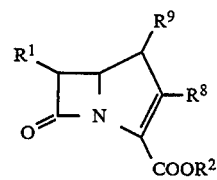

(III)                      (III')

wherein $R^1$ and $R^2$ have the meanings respectively defined hereinbefore; $R^8$ means a functional group selected from the class consisting of hydroxy, mercapto, amino, monosubstituted amino, carboxy and substituted oxycarbonyl or a lower alkyl group containing such a functional group as defined above and optionally having one or more other substituents, the carbon chain of which may optionally be interrupted by 1 or 2 hetero-atoms selected from the class consisting of oxygen, sulfur and nitrogen; $R^9$ means a leaving group, a functional group selected from the class consisting of hydroxy, carboxy and substituted oxycarbonyl, or a lower alkyl group containing such a functional group or a leaving group as defined above and optionally having one or more substituent groups, the carbon chain of which may optionally be interrupted by 1 or more hetero-atoms selected from the class consisting of oxygen, sulfur and nitrogen in the absence or presence of a reagent capable of providing a linking atomic group followed, if necessary, by elimination of any protective group or groups that may be present. This cyclization reaction is generally conducted in an inert solvent.

When compound (III) or (III') contains a reactive group such as amino, hydroxy or carboxy, such group may be protected with a protective group such as those mentioned hereinbefore.

The leaving group mentioned for $R^9$ includes, inter alia, chlorine, bromine, idodine, methanesulfonyloxy, trifluoromethanesulfonyloxy, benzenesulfonyloxy, toluenesulfonyloxy, diethylphosphoryloxy and diphenylphosphoryloxy. The substituted oxycarbonyl group includes, inter alia, phenyloxycarbonyl, p-nitrophenyloxycarbonyl, 2,4,6-trichlorophenyloxycarbonyl, succinimidoxycarbonyl and phthalimidoxycarbonyl.

The reagent which can be used in said cyclization reaction involving a linking atomic group includes various compounds having two functional groups, e.g. carbonic acid derivatives such as carbonyldiimidazoles, aldehydes such as formaldehyde, etc., ketones such as acetone etc., 1,2-dibromoethane, bromoacetic acid, etc., and primary amines such as methylamine and so on.

A reaction accelerator may be used to hasten the cyclization reaction. Though the kind of reaction accelerator depends on the species of functional groups $R^8$ and $R^9$, there can be employed various organic bases such as triethylamine, diisopropylethylamine, etc.; inorganic bases such as sodium hydrogen carbonate, sodium carbonate, potassium carbonate, etc., carbodiimides such as N,N'-dicyclohexylcarbodiimide, N-ethyl-N'-(3-dimethylaminopropyl)carbodiimide, etc., N,N'-carbonyldiimidazole, 2-chloro-1-methylpyridinium chloride, dialkyl azodicarboxylate(alkyl=ethyl, isopropyl or the like)-triphenylphosphine, 2,2'-dipyridyl disulfide-triphenylphosphine, diphenylphosphoryl azide, diethylphosphoryl cyanide and so on.

The inert solvent for this cyclization reaction is also selected according to the species of functional groups $R^8$ and $R^9$. As such, the inert solvent includes, inter alia, various amides such as N,N-dimethylformamide, N,N-dimethylacetamide, etc., ethers such as tetrahydrofuran, dioxane, diethyl ether, etc., halogenated hydrocarbons such as dichloromethane, chloroform, etc., acetonitrile, esters such as methyl acetate, ethyl acetate, etc., aromatic hydrocarbons such as benzene, toluene, etc., water, and various mixtures of such solvents.

The reaction temperature is also dependent on the kinds of functional groups $R^8$ and $R^9$ but is not so critical. However, in order to control side reactions, this cyclization reaction is preferably conducted at a comparatively low temperature, generally in the range of $-20°$ C. to $100°$ C. The reaction time also varies with different species of functional groups $R^8$ and $R^9$ and cannot be generalized. However, the reaction goes to completion in 10 minutes to 72 hours in many cases.

The starting compounds (III) and (III''), which are employed in the practice of the invention, can be synthesized by the processes described, inter alia, in Japanese Kokai Tokkyo Koho No. 69586/1980, No. 89285/1980, No. 202886/1985, No. 195382/1987, No. 303981/1988, No. 170378/1988 and No. 93586/1989 or processes analogous thereto.

The reaction products obtained by the above methods can respectively be isolated and purified by the known procedures such as solvent extraction, pH adjustment, phase transfer, salting-out, crystallization, recrystallization and chromatography. Where the reaction product has a protective group, it can be eliminated, if necessary, by the usual procedure to give the desired compound (I) or salt.

In the fields of β-lactams and peptides, the protective groups for amino, hydroxy and carboxy and the methods for protection and deprotection have been well established. For example, these protective groups can be eliminated by the known methods such as the method employing an acid, the method employing a base, the method employing hydrazine, the reductive method, the method using sodium N-methyldithiocarbamate, etc. as selected according to the kind of protective group to be removed.

The reaction product (I) obtained by the above Production Process 1 or 2 or by other methods is usually in the form of a mixture of diastereomers. Optical resolution of such a mixture can be carried out by fractional recrystallization or column chromatography. In the following description referring to compound (I), a mixture of diastereomers is meant unless otherwise indicated.

The compound (I) of the present invention has a broad antibacterial spectrum and can be used for the prevention and treatment of various diseases caused by pathogenic bacteria in man and animals.

The minimal inhibitory concentrations [MIC (μg/ml)] of a representative compound of the invention were determined by the following method. The results are shown below in the table.

Method for MIC determination

The MIC values of the test compound were determined by the agar dilution method. Thus, 1.0 ml aliquots of serial aqueous dilutions of the test compound were put in petri dishes and 9.0 ml aliquots of Trypticase Soy Agar were added and mixed. Those agar plates were respectively smeared with a suspension (about $10^8$ CFU/ml) of the test organism and incubated at $37°$ C. overnight. The lowest concentration of the test compound at which growth of the test organism was completely inhibited was taken as the minimal inhibitory concentration (MIC).

| Test organism | MIC (μg/ml) $10^8$CFU/ml Compound of Example 3 (7R:7S = 7:3) |
|---|---|
| S. aureus FDA 209P | 0.78 |
| S. aureus 308A-1 | 0.78 |
| S. aureus 1840 | 1.56 |
| S. pyogenes E-14 | 0.78 |
| S. pyogenes S-8 | 0.2 |
| S. mitis America | 0.78 |
| S. pneumoniae Type I | 0.39 |
| C. diphtheriae Tronto | <0.1 |
| E. coli NIHJ JC-2 | 0.2 |
| E. coli NIHJ O-111 | 0.2 |
| E. coli NIHJ T-7 | 0.2 |
| C. freundii IFO 12681 | 0.39 |
| C. freundii TN 474 | 1.56 |
| K. pneumoniae DT | 0.39 |
| K. oxytoca TN 1711 | 0.39 |
| E. cloacae IFO 12937 | 0.78 |
| E. cloacae TN 583 | 0.78 |
| S. marcescens IFO 12648 | 1.56 |
| P. vulgaris IFO 3988 | 3.13 |
| P. mirabilis IFO 3849 | 1.56 |
| M. morganii IFO 3168 | 3.13 |

The following reference and working examples are intended to illustrate the invention in further detail and should by no means be construed as defining the metes and bounds of the invention.

In the reference and working examples given hereunder, the procedure of elution in column chromatography was invariably carried out under TLC (thin-layer chromatography) monitoring. In TLC monitoring, Merck's 60F$_{254}$ was used as the TLC plate and the eluent for column chromatography was used as the developer. A UV detector was used for spot detection. As the column packing silica gel, Merck's Kieselguhr 60 (70~230 or 230~400 mesh) was used. The CHP-20 resin is a product of Mitsubishi Chemical Industries, Ltd. The NMR spectra were recorded with EM390 (90 MHz) and GEMINI 200 (200 MHz) using tetramethylsilane or 3-(trimethylsilyl)propionic 2,2,3,3-d$_4$ acid sodium salt as an internal or external reference and all the δ values were shown in ppm. The parenthesized figures for solvent mixtures are proportions in volume of the solvents constituting the respective mixtures. The % figures for solvent mixtures represent percents by volume. Some of the symbols used in Reference Examples and Examples have the following meanings.

s: singlet
d: doublet
t: triplet
q: quartet dd: double doublet
ddd: double double doublet
ddt: double double triplet
m: multiplet
dt: double triplet
dq: double quartet
qd: quadruple doublet
br.: broad
J: coupling constant

REFERENCE EXAMPLE 1

Production of (3S,4S)-3-[(R)-[1-(tert-butyldimethylsilyl)oxy]ethyl]-4-[(RS)-2-oxotetrahydro-2H-thiopyran-3-yl]azetidin-2-one:

To a mixed solution of (3R,4R)-4-acetoxy-3-[(R)[1-(tert-butyldimethylsilyl)oxy]ethyl]-1-trimethyl-silylazetidin-2-one (9.35 g) and 6-(trimethylsilyloxy)-3,4-dihydro-2H-thiopyran (4.25 g) in dichloromethane (25 ml) was added a dichloromethane solution (5 ml) of trimethylsilyl trifluoromethanesulfonate (690 mg) under water cooling (15° C.) and the mixture was stirred at room temperature for 4 hours. The reaction mixture was adjusted to pH 7 with 2N aqueous potassium carbonate solution and the aqueous layer was extracted with dichloromethane. The organic layer was dried over anhydrous sodium sulfate and the solvent was distilled off under reduced pressure. The residue was dissolved in tetrahydrofuran-water (7:1, 80 ml) followed by addition of pyridinium p-toluenesulfonate (126 mg) and the mixture was stirred at room temperature for 1.5 hours. The solvent was then distilled off under reduced pressure and ether (200 ml) was added to the residue. The organic layer was washed successively with water and saturated aqueous sodium chloride solution and dried over anhydrous sodium sulfate. The solvent was then distilled off under reduced pressure and the residue was purified by flash column chromatography (packing: silica gel 250 g; ethyl acetate-hexane 2:3) to give the title compound (7.68 g) (diastereomer ratio: R:S (for the configuration of thiopyran ring)=69:31).

IR (KBr): 3160, 3070, 2950, 2860, 1764, 1717, 1680, 1656 cm$^{-1}$

Configuration of thiopyran ring: R $^1$H-NMR (CDCl$_3$) δ: 0.08 (6H, s), 0.87 (9H, s), 1.22 (3H, d, J=6.2 Hz), 1.75–2.00 (1H, m), 2.02–2.22 (3H, m), 2.77 (1H, dt, J=10.8 Hz, 4.6 Hz), 3.01 (1H, dd, J=5.0 Hz, 2.4 Hz), 3.07–3.25 (2H, m), 4.12–4.26 (1H, m), 4.27 (1H, dd, J=4.6 Hz, 2.4 Hz), 5.77 (1H, brs)

Configuration of thiopyran ring: S $^1$H-NMR (CDCl$_3$) δ: 0.08 (6H, s), 0.88 (9H, s), 1.25 (3H, d, J=6.0 Hz), 1.50–1.75 (1H, m), 2.02–2.22 (3H, m), 2.51–2.66 (1H, m), 2.71–2.78 (1H, m), 3.07–3.25 (2H, m), 3.65 (1H, dd, J=10.0 Hz, 2.0 Hz), 4.10–4.24 (1H, m), 6.23 (1H, brs)

REFERENCE EXAMPLES 2

Production of (3S,4S)-3-[(R)-1-(trimethylsilyloxy)-ethyl]-4-[(RS)-2-oxotetrahydro-2H-thiopyran-3-yl]azetidin-2-one:

To a suspension of the compound of Reference Example 1 (1.72 g) in acetonitrile (13 ml) was added boron trifluoride etherate (1.17 g) at 0° C. and the mixture was stirred at the same temperature for 3 hours. This reaction mixture was poured in ice-water (50 ml) and adjusted to pH 7 with 1N-aqueous sodium hydroxide solution. After salting-out, the system was extracted with ethyl acetate-tetrahydrofuran and the extract was dried over anhydrous sodium sulfate. Finally the solvent was distilled off under reduced pressure to give (3S,4S)-3-[(R)-1-hydroxyethyl]-4-[(RS)-2-oxotetrahydro-2H-thiopyran-3-yl]azetidin-2-one (1.15 g). A suspension (15 ml) of this product in dichloromethane was cooled to 0° C., and chlorotrimethylsilane (1.63 g) and, then, triethylamine (1.52 g) were added. The mixture was stirred at room temperature for 3 hours. The solvent and the excess reagents were distilled off under reduced pressure and ether (30 ml) was added to the residue. The insolubles were filtered off and the filtrate was concentrated under reduced pressure. To a suspension (22.5 ml) of the oily residue in ethyl acetate-methanol (1:1) was added silica gel (12.6 g) and the mixture was stirred for 10 hours. The silica gel was filtered off and the solvent was distilled off under reduced pressure. The residue was purfied by flash column chromatography (packing: silica gel 25 g; ethyl acetate-hexane 1:2) to give the title compound (874 mg) [diastereomer ratio: R:S (the configuration of thiopyran ring)=66:34]. The spectral data on purified samples of the respective isomers are given below.

Configuration of thiopyran ring: R

IR (KBr): 3220, 2965, 1758, 1645 cm$^{-1}$ $^1$H-NMR (CDCl$_3$) δ: 0.12 (9H, s), 1.24 (3H, d, J=6.2 Hz), 1.75–2.00 (1H, m), 2.04–2.23 (3H, m), 2.77 (1H, ddd, J=10.6 Hz, 5.2 Hz, 4.6 Hz), 3.02 (1H, dd, J=6.0 Hz, 2.4 Hz), 3.13–3.22 (2H, m), 4.18 (1H, qd, J=6.2 Hz, 6.0 Hz), 4.20 (1H, dd, J=4.6 Hz, 2.4 Hz), 5.80 (1H, brs)

Configuration of thiopyran ring: S

IR (KBr): 3240, 2950, 1760, 1650 cm$^{-1}$ $^1$H-NMR (CDCl$_3$) δ: 0.12 (9H, s), 1.29 (3H, d, J=6.2 Hz), 1.48–1.80 (1H, m), 2.03–2.29 (3H, m), 2.46–2.66 (1H, m), 2.74 (1H, ddd, J=6.6 Hz, 2.0 Hz, 1.2 Hz), 3.13–3.23 (2H, m), 3.56 (1H, dd, J=10.0 Hz, 2.0 Hz), 4.03–4.20 (1H, m), 6.23 (1H, brs)

REFERENCE EXAMPLE 3

Production of allyl [(3S,4S)-2-oxo-4-[(RS)-2-oxotetrahydro-2H-thiopyran-3-yl]-3-[(R)-1-(trimethylsilyloxy)-ethyl]azetidin-1-yl]glyoxylate:

To a solution of the compound of Reference Example 2 [294 mg, R:S (the configuration of thiopyran ring)=79:21] in dichloromethane (3 ml) was added a solution of triethylamine (395 mg) in dichloromethane (2 ml), followed by addition of a solution of allyl chloroglyoxylate (145 mg) in dichloromethane (2 ml) dropwise at −20° C. over a period of 15 minutes. The mixture was stirred at the same temperature for a further 50 minutes, after which time a solution of allyl chloroglyoxylate (145 mg) in dichloromethane (2 ml) was added, followed by stirring for 30 minutes. The solvent was then distilled off under reduced pressure and the residue was diluted with ethyl acetate (20 ml), washed successively with water and saturated aqueous sodium chloride solution and dried over anhydrous sodium sulfate. The solvent was distilled off under reduced pressure. To a solution of the residue in toluene-dichloromethane (3:5, 8 ml) were added N,O-bis(trimethylsilyl)trifluoroacetamide (1 ml) and a catalyst amount of 4-(dimethylamino)pyridine and the mixture was stirred at 45° C. for 30 minutes. The solvent was then distilled off under reduced pressure and the residue was purified by flash column chromatography (packing: silica gel 15 g; ethyl acetate-hexane 1:6) to give the title compound (332 mg) [diastereomer ratio: R:S (the configuration of thiopyran ring)=75:25].

IR (Neat): 2955, 2800, 1810, 1753, 1700, 1650, 1440, 1380 cm$^{-1}$

Configuration of thiopyran ring: R

¹H-NMR (CDCl₃) δ: 0.10 (9H, s), 1.23 (3H, d, J=6.4 Hz), 1.73-2.30 (4H, m), 3.12-3.24 (3H, m), 3.28 (1H, dd, J=4.6 Hz, 3.4 Hz), 4.25 (1H, dq, J=6.4 Hz, 4.8 Hz), 4.43 (1H, dd, J=4.8 Hz, 3.4 Hz), 4.81 (2H, dt, J=6.0 Hz, 1.2 Hz), 5.32 (1H, ddd, J=10.2 Hz, 2.4 Hz, 1.2 Hz), 5.41 (1H, ddd, J=17.2 Hz, 2.4 Hz, 1.2 Hz), 5.97 (1H, ddd, J=17.2 Hz, 10.2 Hz, 6.0 Hz)

Configuration of thiopyran ring: S

¹H-NMR (CDCl₃) δ: 0.09 (9H, s), 1.23 (3H, d, J=6.4 Hz), 1.73-2.30 (4H, m), 3.12-3.24 (3H, m), 3.40-3.52 (1H, m), 4.17-4.32 (1H, m), 4.81 (2H, dt, J=6.0 Hz, 1.2 Hz), 4.86 (1H, dd, J=4.0 Hz, 3.8 Hz), 5.32 (1H, ddd, J=10.2 Hz, 2.4 Hz, 1.2 Hz), 5.41 (1H, ddd, J=17.2 Hz, 2.4 Hz, 1.2 Hz), 5.97 (1H, ddd, J=17.2 Hz, 10.2 Hz, 6.0 Hz)

REFERENCE EXAMPLE 4

Production of (3S,4S)-3-[(R)-[1-(tert-butyldimethylsilyl)oxy]ethyl]-4-[(RS)-2-oxotetrahydrothiophen-3-yl]azetidin-2-one:

Using (3R,4R)-4-acetoxy-3-[(R)-[1-(tert-butyldimethylsilyl)oxy]ethyl]-1-trimethylsilylazetidin-2-one (7.14 g) and 4,5-dihydro-2-(trimethylsilyloxy)thiophene (4.51 g), the title compound (6.00 g) was produced by generally the same procedure as Reference Example 1. [Diastereomer ratio: R:S (the configuration of thiophene ring)=66:34] The spectral data on purified samples of the respective isomers are given below.

Configuration of thiophene ring: R

IR (KBr): 3180, 3100, 2960, 2940, 2865, 1763, 1728, 1700 cm⁻¹ ¹H-NMR (CDCl₃) δ: 0.08 (6H, s), 0.87 (9H, s), 1.23 (3H, d, J=6.4 Hz) 2.17-2.34 (1H, m), 2.37-2.54 (1H, m), 2.80 (1H, ddd, J=11.0 Hz, 7.0 Hz, 4.0 Hz), 2.96 (1H, dd, J=5.2 Hz, 2.6 Hz), 3.34-3.41 (2H, m), 4.14-4.26 (2H, m), 5.71 (1H, brs)

Configuration of thiophene ring: S

IR (KBr): 3200, 2970, 2940, 2865, 1770, 1734, 1700 cm⁻¹ ¹H-NMR (CDCl₃) δ: 0.08 (6H, s), 0.88 (9H, s), 1.23 (3H, d, J=6.2 Hz) 1.91-2.23 (1H, m), 2.40-2.65 (2H, m), 2.79-2.83 (1H, m), 3.29-3.40 (2H, m), 3.62 (1H, dd, J=9.2 Hz, 2.0 Hz), 4.20 (1H, qd, J=6.2 Hz, 5.4 Hz), 6.42 (1H, brs)

REFERENCE EXAMPLE 5

Production of (3S,4S)-3-[(R)-1-(trimethylsilyloxy)-ethyl]-4-[(RS)-2-oxotetrahydrothiophen-3-yl]azetidin-2-one:

Using the compound of Reference Example 4 (1.32 g), the procedure of Reference Example 2 was followed to give the title compound (1.07 g) [diastereomer ratio: R:S (the configuration of thiophene ring)=64:36]. The spectral data on purified samples of the respective isomers are given below.

Configuration of thiophene ring: R

IR (KBr): 3225, 2960, 1763, 1720, 1690 cm⁻¹ ¹H-NMR (CDCl₃) δ: 0.13 (9H, s), 1.25 (3H, d, J=6.2 Hz), 2.16-2.54 (2H, m), 2.81 (1H, ddd, J=11.2 Hz, 7.0 Hz, 4.2 Hz), 2.97 (1H, dd, J=6.0 Hz, 2.4 Hz), 3.34-3.41 (2H, m), 4.12 (1H, dd, J=4.2 Hz, 2.4 Hz), 4.18 (1H, qd, J=6.2 Hz, 6.0 Hz), 5.71 (1H, brs)

Configuration of thiophene ring: S

IR (KBr): 3280, 2960, 1760, 1690 cm⁻¹ ¹H-NMR (CDCl₃) δ: 0.13 (9H, s), 1.27 (3H, d, J=6.2 Hz), 1.09-2.14 (1H, m), 2.41-2.68 (2H, m), 2.81 (1H, ddd, J=7.0 Hz, 2.0 Hz, 1.4 Hz), 3.29-3.40 (2H, m), 3.52 (1H, dd, J=9.4 Hz, 2.0 Hz), 4.13 (1H, dq, J=7.0 Hz, 6.2 Hz), 6.42 (1H, brs)

REFERENCE EXAMPLE 6

Production of allyl [(3S,4S)-2-oxo-4-[(R)-2-oxotetrahydrothiophen-3-yl]-3-[(R)-1-(trimethylsilyloxy)-ethyl]azetidin-1-yl]glyoxylate:

Using the compound of Reference Example 5 (710 mg), the procedure of Reference Example 3 was followed to give the title compound (499 mg). In addition, the diastereomer (120 mg) of the title compound was obtained.

IR (KBr): 2980, 1803, 1753, 1700, 1690, 1395 cm⁻¹ ¹H-NMR (CDCl₃) δ: 0.10 (9H, s), 1.24 (3H, d, J=6.4 Hz), 2.20-2.60 (2H, m), 3.07 (1H, dt, J=10.0 Hz, 6.6 Hz), 3.23-3.56 (3H, m), 4.28 (1H, dq, J=6.4 Hz, 4.4 Hz), 4.40 (1H, dd, J=6.4 Hz, 3.2 Hz), 4.81 (2H, brd, J=6.0 Hz), 5.32 (1H, brd, J=10.2 Hz), 5.41 (1H, brd, J=17.2 Hz), 5.97 (1H, ddt, J=17.2 Hz, 10.2 Hz, 6.0 Hz)

REFERENCE EXAMPLE 7

The two diastereomers obtained in Reference Example 2 were respectively reacted in the same manner as Reference Example 3 to give allyl [(3S,4S)-2-oxo-4-[(R)-2-oxotetrahydro-2H-thiopyran-3-yl]-3-[(R)-1-(trimethylsilyloxy)-ethyl]azetidin-1-yl]glyoxylate (R-compound) and allyl [(3S,4S)-2-oxo-4-[(S)-2-oxotetrahydro-2H-thiopyran-3-yl]-3-[(R)-1-(trimethylsilyloxy)ethyl]azetidin-1-yl]glyoxylate (S-compound)

Configuration of thiopyran ring: R: colorless crystals (m.p., 82°-84° C.)

IR (KBr): 2970, 2910, 1800, 1756, 1697, 1655, 1397 cm⁻¹

Configuration of thiopyran ring: S: colorless oil

IR (KBr): 2950, 1800, 1750, 1697, 1650 cm⁻¹

REFERENCE EXAMPLE 8

A mixed solution of (3R,4R)-4-acetoxy-3-[(R)-1-[(tert-butyldimethylsilyl)oxy]ethyl]-1-azetizin-2-one (4.0 g) and 1-[(trimethylsilyl)oxy]-3,4-dihydronaphthalene (3.34 g) in dichloromethane (15 ml) was added to a dichloromethane solution of trimethylsilyl trifluoromethanesulfonate (311 mg) at 0° C. and the mixture was stirred for 2.5 hours. To this reaction mixture was added saturated aqueous sodium hydrogen carbonate solution and the mixture was further stirred for 10 minutes. The aqueous layer was extracted with dichloromethane. The organic layer was dried over anhydrous sodium sulfate and the solvent was distilled off under reduced pressure. Finally the residue was purified by flash column chromatography (packing: silica gel 200 g; ether-toluene 1:4) to give 1.77 g and 1.59 g of colorless crystals of (3S,4R)-3-[(R)-1-[(tert-butyldimethylsilyl)oxy]ethyl]-4-[(R)-1,2,3,4-tetrahydro-1-oxonaphthalen-2-yl]azetidin-2-one (R-compound) and (3S,4R)-3-[(R)-1-[(tert-butyldimethylsilyl)oxy]ethyl]-4-[(S)-1,2,3,4-tetrahydro-1-oxonaphthalen-2-yl]azetidin-2-one (S-compound), respectively.

R-compound:

IR (KBr): 2965, 2940, 2865, 1765, 1718, 1683, 1603 cm⁻¹

S-compound:

IR (KBr): 3220, 2960, 2940, 2865, 1764, 1730, 1688, 1600 cm⁻¹

Generally in the same manner as above, the following compounds were synthesized.

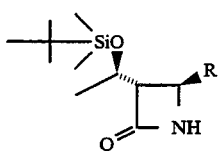
| R | Configuration of 4-substituent | m.p. (°C.) | IR(cm$^{-1}$) |
|---|---|---|---|
| (2-methylcyclohexanone) | R | 109–111 | (KBr) 3170, 3100, 2930, 2860, 1755, 1715 |
| (2-methylcyclohexanone) | S | 97–102 | (KBr) 3180, 2940, 2860, 1760, 1710 |
| (2-methylcycloheptanone) | R | 112–114 | (KBr) 3150, 3080, 2930, 2850, 1755, 1710 |
| (2-methylcycloheptanone) | S | 98–100 | (KBr) 3160, 3090, 2930, 2850, 1760, 1720, 1700 |
| (3-methyltetrahydrothiopyran-4-one) | R | 147–152 | (KBr) 3240, 2950, 2920, 2850, 1760, 1720 |
| (3-methyltetrahydrothiopyran-4-one) | S | 142–143 | (KBr) 3250, 2950, 2920, 2850, 1760, 1730, 1700 |
| (methyl-dihydrobenzothiophenone) | R & S mixture | | (KBr) 3450, 3200, 2970, 2945, 2860, 1755, 1695 |
| (2-methyltetrahydropyran-3-one) | R & S mixture | | (Neat) 2950, 2930, 2850, 1760, 1725 |

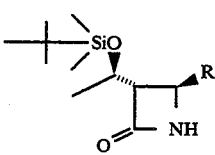

| R | Configuration of 4-substituent | m.p. (°C.) | IR(cm⁻¹) |
|---|---|---|---|
| (tetrahydronaphthalenone with OCH₂CH(NH-COO-allyl)) | R & S mixture | | (KBr) 3250, 2950, 1760, 1725, 1678, 1603, 1530 |
| (tetrahydrothiopyranone, methyl) | R | | (Neat) 2960, 2930, 2860, 1760, 1710 |
| (tetrahydrothiopyranone, methyl) | S | | (Neat) 2960, 2930, 2860, 1755, 1710 |
| (N-allyloxycarbonyl piperidinone, methyl) | R | | (Neat) 2960, 2940, 2860, 1760, 1700 |
| (N-allyloxycarbonyl piperidinone, methyl) | S | | (Neat) 2960, 2940, 2860, 1760, 1700 |

REFERENCE EXAMPLE 9

To stannous chloride (379 mg) was added a dichloromethane solution (10 ml) of chlorotrimethylsilane (217 mg) followed by addition of a dichloromethane solution (10 ml) of (3R,4R)-4-acetoxy-3-[(R)-1-[(tert-butyldimethylsilyl)oxy]ethyl]-1-trimethylsilylazetidin-2-one (7.19 g). To this suspension was added a dichloromethane solution (10 ml) of 2-[(trimethylsilyl)oxy]-1,3-cyclohexadiene (4.05 g) dropwise at room temperature over a period of 1 hour. The mixture was stirred at 25° C. for 2 hours, at the end of which time a dichloromethane solution (10 ml) of 2-[(trimethylsilyl)oxy]-1,3-cyclohexadiene (5.38 g) was added dropwise over a period of 1 hour. The mixture was further stirred for 5 hours and then allowed to stand at 0° C. overnight. The solvent was then distilled off under reduced pressure. To the residue were added ether (100 ml) and aqueous sodium hydrogen carbonate solution (30 ml) and the mixture was stirred for 10 minutes. The insolubles were filtered off and the aqueous layer was extracted with ether. The ether layer was washed with saturated aqueous sodium chloride solution and dried over anhydrous sodium sulfate. The solvent was then distilled off under reduced pressure and the residue was dissolved in THF-water (17:2, 95 ml). To this solution was added pyridinium p-toluenesulfonate (610 mg) and the mixture was stirred at room temperature for 1 hour. The solvent was distilled off under reduced pressure and ether (150 ml) was added to the residue. The organic layer was washed successively with water and saturated sodium chloride solution and dried over anhydrous sodium sulfate. The solvent was then distilled off under reduced pressure and the residue was purified by flash column chromatography (packing: silica gel 300 g; ether-hexane 5:1) to give (3S,4R)-3-[(R)-1-[(tert-butyldimethylsilyl)oxy]ethyl]-4-[(R)-2-oxo-3-cyclohexen-1-yl]azetidin-2-one (R-compound; 1.01 g) and (3S,4R)-3-[(R)-1-[(tert-butyldimethylsilyl)oxy]ethyl]-4-[(S)-2-oxo-3-cyclohexen-1-yl]azetidin-2-one (S-compound; 0.96 g).

R-compound

IR (KBr): 3000–3100, 2960, 2940, 2860, 1760, 1710, 1677 cm$^{-1}$ $^1$H-NMR (CDCl$_3$) δ: 0.08 (6H, s), 0.87 (9H, s), 1.23 (3H, d, J=6.2 Hz), 1.60–2.60 (5H, m), 3.02 (1H, dd, J=5.2 & 2.4 Hz), 4.23 (1H, qd, J=6.2 & 6.0 Hz), 4.29 (1H, dd, J=4.4 & 2.4 Hz), 5.69 (1H, brs), 6.05 (1H, dt, J=10.2 & 1.8 Hz), 6.96–7.70 (1H, m)

S-compound:

IR (KBr): 3260, 2960, 2940, 2860, 1760, 1730, 1678 cm$^{-1}$ $^1$H-NMR (CDCl$_3$) δ: 0.07 (3H, s), 0.08 (3H, s), 0.88 (9H, s), 1.25 (3H, d, J=6.2 Hz), 1.60–1.84 (1H, m), 2.08–2.53 (4H, m), 2.76 (1H, ddd, J=5.8, 2.0 & 1.0 Hz), 3.60 (1H, dd, J=10.2 & 2.0 Hz), 4.18 (1H, qd, J=6.2 & 6.0 Hz), 6.03 (1H, dd, J=10.0 & 1.8 Hz), 6.36 (1H, brs), 6.96–7.80 (1H, m)

REFERENCE EXAMPLE 10

The compounds obtained in Reference Examples 8, 9, and 12 were respectively subjected to the same reaction as Reference Example 2 to give the following compounds.

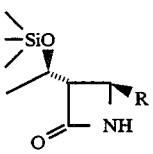

| R | Configuration of 4-substituent | m.p. (°C.) | IR(cm$^{-1}$) |
|---|---|---|---|
| ![naphthalenone with methyl] | R | | (Neat) 3260, 2960, 1760, 1685, 1600 |
| ![naphthalenone with methyl] | S | | (KBr) 3255, 2970, 1760, 1688, 1600 |
| ![methylcyclohexanone] | R | 95–99 | (KBr) 2960, 2900, 1760, 1705 |
| ![methylcyclohexanone] | S | 71–73 | (KBr) 2950, 2870, 1770, 1755 |
| ![methylcycloheptanone] | R | 77–81 | (KBr) 2930, 2850, 1755, 1705, 1680 |
| ![methylcycloheptanone] | S | | (Neat) 2930, 2850, 1755, 1700, 1455 |
| ![methyl thiopyranone] | R & S mixture | | (Neat) 2350, 2950, 1760, 1700 |

-continued

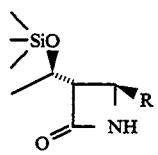

| R | Configuration of 4-substituent | m.p. (°C.) | IR(cm$^{-1}$) |
|---|---|---|---|
| (4,5,6,7-tetrahydro-5-methyl-4-oxobenzothiophene) | R | | (Neat) 3260, 2950, 1750, 1670, 1520 |
| (4,5,6,7-tetrahydro-5-methyl-4-oxobenzothiophene) | S | 130–131 | (KBr) 3250, 3100, 3075, 2950, 2850, 1752, 1670, 1520 |
| (2-methyl-tetrahydropyran-3-one) | R & S mixture | | (Neat) 2960, 2860, 1760, 1725 |
| (tetrahydronaphthalenone with allyl carbamate) | R | | (KBr) 3320, 2950, 1755, 1720, 1667, 1600, 1528 |
| (2-methyl-tetrahydrothiopyran-3-one) | R | | (Neat) 2950, 1760, 1710 |
| (2-methyl-tetrahydrothiopyran-3-one) | S | | (Neat) 2960, 1760, 1710 |
| (N-allyloxycarbonyl-3-methyl-4-piperidinone) | R | | (Neat) 2970, 1765, 1700 |
| (N-allyloxycarbonyl-3-methyl-4-piperidinone) | S | | (Neat) 2960, 1760, 1700 |

-continued

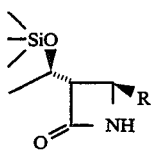

| R | Configuration of 4-substituent | m.p. (°C.) | IR(cm$^{-1}$) |
|---|---|---|---|
| (2-oxocyclohex-3-enyl) | R | | (KBr) 3225, 2965, 1760, 1717, 1673 |
| (2-oxocyclohex-3-enyl) | S | | (KBr) 3225, 2965, 1760, 1735, 1673 |
| (2-oxocyclohexyl) | R & S mixture | | (Neat) 3270, 2960 2855, 1760 1720 |

REFERENCE EXAMPLE 11

The compounds of Reference Example 10 were reacted in generally the same manner as Reference Example 3 to give the following compounds.

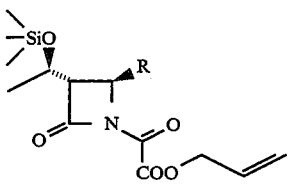

| R | Configuration of 4-substituent | m.p. (°C.) | IR(cm$^{-1}$) |
|---|---|---|---|
| (1-oxo-tetrahydronaphthyl) | R | 102–105 | (KBr) 2965, 1795, 1755, 1693, 1678 |
| (1-oxo-tetrahydronaphthyl) | S | 97–98 | (KBr) 2960, 1805, 1750, 1690, 1673, 1600 |
| (2-oxocyclohexyl) | R | 95–96 | (KBr) 2940, 1810, 1760, 1715, 1680 |

-continued
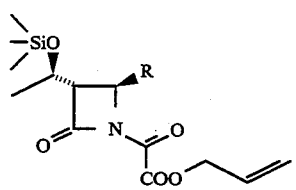
| R | Configuration of 4-substituent | m.p. (°C.) | IR(cm$^{-1}$) |
|---|---|---|---|
| (2-methylcyclohexanone) | S | | (Neat) 2960, 2870, 1805, 1755, 1710 |
| (2-methylcycloheptanone) | R | | (Neat) 2930, 2850, 1805, 1755, 1700 |
| (2-methylcycloheptanone) | S | | (Neat) 2930, 2850, 1805, 1755, 1700 |
| (6-methylcyclohex-2-enone) | R | | (KBr) 2960, 1804, 1753, 1685, 1667 |
| (6-methylcyclohex-2-enone) | S | | (KBr) 2960, 1804, 1753, 1685, 1667 |
| (3-methyltetrahydrothiopyran-4-one) | R | 127–134 | (KBr) 2960, 2900, 1805, 1760, 1700 |
| (3-methyltetrahydrothiopyran-4-one) | S | 65–70 | (KBr) 2950, 1810, 1760, 1700 |
| (methyl-thienocyclohexanone) | R | 113 | (KBr) 3100, 3075, 2950, 1800, 1756, 1687, 1668, 1525 |

-continued
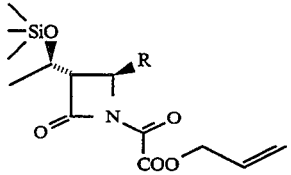
| R | Configuration of 4-substituent | m.p. (°C.) | IR(cm$^{-1}$) |
| --- | --- | --- | --- |
| 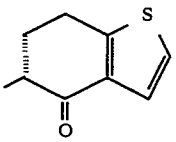 | S | 122 | (KBr) 3120, 3080, 2950, 1805, 1750, 1692, 1660, 1528 |
| 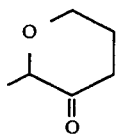 | R & S mixture | | (Neat) 2950, 2850, 1805, 1850, 1720, 1700 |
| 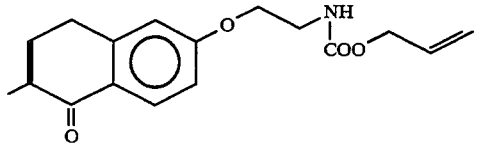 | R | | (Neat) 3390, 3080, 2960, 1805, 1760, 1725, 1700, 1600, 1525 |
| 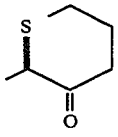 | R | | (Neat) 2970, 1815, 1765, 1710, 1580 |
| 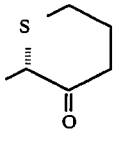 | S | | (Neat) 2960, 1810, 1760, 1715, 1575 |
| 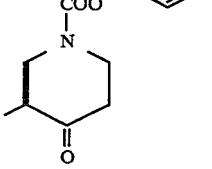 | R | | (Neat) 2960, 1810, 1760, 1710 |
| 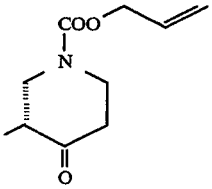 | S | | (Neat) 2960, 1810, 1760, 1705 |
| 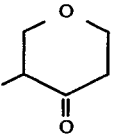 | R & S mixture | | (Neat) 2960, 1810, 1760, 1700 |

REFERENCE EXAMPLE 12

1) In dichloromethane (40 ml) was suspended tin (II) triflate (4.58 g) followed by addition of 1-ethylpiperidine (1.70 ml) at −15° C. Then, tetrahydro-4H-pyran-4-one (1.00 g) was added. The mixture was stirred at the same temperature for 25 minutes, after which a solution of (3R,4R)-4-acetoxy-3-[(R)-[1-(tert-butyldimethylsilyl)oxy]ethyl]azetidin-2-one (2.59 g) in dichloromethane (20 ml) was added. The mixture was stirred at −10°~15° C. for 7.5 hours. Then, under ice-cooling, the reaction mixture was diluted with aqueous sodium hydrogen carbonate solution and stirred for 10 minutes. The organic layer was separated, washed with aqueous sodium chloride solution and dried. The solvent was then distilled off under reduced pressure and the residue was purified by column chromatography (column packing: silica gel, 100 g; ethyl acetate-hexane=1:1). The procedure gave 1.04 g of (3S,4R)-3-[(R)-[1-(tert-butyldimethylsilyl)oxy]ethyl]-4-[(RS)-4-oxotetrahydropyran-3-yl]azetidin-2-one. m.p. 97°–98° C.

IR(Neat): 3300, 2955, 2930, 2855, 1760, 1715 cm$^{-1}$
Anal Calcd for $C_{16}H_{29}NO_4Si$: C,58.68; H,8.93; N,4.28
Found: C,58.45; H,8.97; N,3.90

2) In dichloromethane (50 ml) was dissolved (3R,4R)-4-acetoxy-3-[(R)-1-(tert-butyldimethylsilyl)oxy]ethyl]-azetidin-2-one (2.87 g) followed by addition of 4-[(trimethysilyl)oxy]-5,6-dihydro-2H-pyran (3.4 g). Then, zinc bromide (0.76 g) was added with ice-cooling. The mixture was stirred at the same temperature for 30 minutes and, then, at room temperature for 16 hours. This reaction mixture was diluted with saturated aqueous sodium hydrogen carbonate solution (50 ml), stirred for 10 minutes, and extracted with dichloromethane. The extract was washed with aqueous sodium chloride solution and dried and the solvent was distilled off under reduced pressure. The residue was then purified by silica gel column chromatography to give 3.26 g of (3S,4R)-3-[(R)-[1-(tert-butyldimethylsilyl)oxy]ethyl]-4-[(RS)-4-oxotetrahydropyran-3-yl]azetidin-2-one.

REFERENCE EXAMPLE 13

To a solution of 1,4-dithian-2-one (8.05 g) in dichloromethane (40 ml) was added a solution of triethylamine (6.68 g) in dichloromethane (5 ml), followed by addition of a solution of trimethylsilyl trifluoromethanesulfonate (16.0 g) in dichloromethane (20 ml). The mixture was stirred for 2.5 hours. To this reaction mixture was added a solution of (3R,4R)-4-acetoxy-3-[(R)-[1-(tert-butyldimethylsilyl)oxy]ethyl]azetidin-2-one (17.25 g) in dichloromethane (30 ml) and the mixture was stirred at 0° C. for 4 hours. The reaction mixture was then diluted with saturated aqueous sodium hydrogen carbonate solution and ice-water, stirred and extracted with dichloromethane. The organic layer was dried over anhydrous sodium sulfate and the solvent was distilled off under reduced pressure. The residue was dissolved in THF-water (7:1, 160 ml) followed by addition of pyridinium p-toluenesulfonate (2.52 mg), and the mixture was stirred at room temperature for 1 hour. The solvent was then distilled off under reduced pressure and the residue was dissolved in ether, washed with water and saturated aqueous sodium chloride solution in that order and dried over anhydrous sodium sulfate. The solvent was distilled off under reduced pressure and the residue was purified by flash column chromatography (packing; silica gel; ethyl acetate-hexane=2:3) to give 16.74 g of (3S,4S)-3-[(R)-1-[(tert-butyldimethylsilyl)oxy]ethyl]-4-[(RS)-3-oxo-1,4-dithian-2-yl]azetidin-2-one.

IR (KBr): 3400, 3210, 2930, 2895, 1755, 1718, 1670 cm$^{-1}$

REFERENCE EXAMPLE 14

The compound of Reference Example 13 was treated in the same manner as in Reference Example 2 to give (3S,4S)-3-[(R)-1-(trimethylsilyloxy)-ethyl]-4-[(R)-3-oxo-1,4-dithian-2-yl]azetidin-2-one (R-form) and (3S,4S)-3-[(R)-1-(trimethylsilyloxy)-ethyl]-4-[(S)-3-oxo-1,4-dithian-2-yl]azetidin-2-one (S-form).

Configuration of thiopyran ring: R
IR(Neat): 3260, 2955, 1760, 1683 cm$^{-1}$
Configuration of thiopyran ring: S
IR (KBr): 3340, 2975, 2950, 2925, 2860, 1765, 1670 cm$^{-1}$

REFERENCE EXAMPLE 15

A solution of (3S,4S)-3-[(R)-1-(trimethylsilyloxy)-ethyl]-4-[(R)-3-oxo-1,4-dithian-2-yl]azetidin-2-one (650 mg), prepared in Reference Example 14, in dichloromethane (10 ml) was cooled at 0° C. and a solution of pyridine (483 mg) in dichloromethane (2 ml) and a solution of allyl chloroglyoxylate (603 g) in dichloromethane (3 ml) were added. The mixture was stirred at the same temperature for 2 hours. To this mixture was added ethanol (187 mg) at 0° C. and the mixture was stirred for 10 minutes, after which ether (30 ml) was added. The organic layer was washed with water, saturated copper sulfate solution and saturated aqueous sodium chloride solution in the order mentioned and dried over anhydrous magnesium sulfate. The solvent was then distilled off under reduced pressure and the residue was purified by flash column chromatography (packing: silica gel; ethyl acetate-hexane=1:5). The procedure gave allyl [(3S,4S)-2-oxo-4-[(R)-3-oxo-1,4-dithian-2-yl]-3-[(R)-1-(trimethylsilyloxy)ethyl]azetidin-1-yl]glyoxylate as a colorless oil (853 mg).

IR (KBr): 2950, 1817, 1750, 1680 cm$^{-1}$ $^1$H-NMR (CDCl$_3$) δ: 0.10 (9H, s), 1.23 (3H, d, J=6.4 Hz), 3.05–3.55 (5H, m), 4.18–4.35 (1H, m), 4.45–4.55 (2H, m), 4.73–4.85 (2H, m), 5.27–5.50 (2H, m), 5.87–6.08 (1H, m)

In the same manner as above, allyl [(3S,4S)-2-oxo-4-[(S)-3-oxo-1,4-dithian-2-yl]-3-[(R)-1-(trimethylsilyloxy)-ethyl]azetidin-1-yl]glyoxylate was obtained.

$^1$H-NMR (CDCl$_3$) δ: 0.09 (9H, s), 1.33 (3H, d, J=6.4 Hz), 3.05–3.55 (5H, m), 4.18–4.35 (1H, m), 4.45–4.55 (1H, m), 4.73–4.85 (2H, m), 4.98 (1H, dd, J=3.6 & 2.8 Hz), 5.27–5.50 (2H, m), 5.87–6.08 (1H, m)

REFERENCE EXAMPLE 16

A mixed solution of 2-mercaptoethanol (25.0 g) and pyridinium p-toluenesulfonate (8.04 g) in dichloromethane (400 ml) was cooled with ice and 3,4-dihydro-2H-pyran (70 g) was gradually added. The mixture was stirred at room temperature for 3 hours. Then, 3,4-dihydro-2H-pyran (10.8 g) was further added and the mixture was stirred for an additional 3 hours. To this reaction mixture was added ether (1 l) and the organic layer was washed with aqueous sodium chloride solution and dried over anhydrous sodium sulfate and the solvent was distilled off under reduced pressure. The procedure gave 78.8 g of tetrahydropyran-2-yl 2-[(tetrahydropyran-2-yl)thio]ethyl ether as a colorless oil.

IR(Neat): 2940, 2860, 1460, 1448, 1437, 1347, 1320 cm$^{-1}$ $^1$H-NMR (CDCl$_3$) δ: 1.42–2.02 (12H, m), 2.68–3.01 (2H, m), 3.45–3.75 (3H, m), 3.82–3.99 (2H, m), 4.01–4.16 (1H, m), 4.61–4.68 (1H, m), 4.87–4.97 (1H, m)

REFERENCE EXAMPLE 17

To a solution of the compound of Reference Example 16 (78.8 g) in ethanol (1.5 ) was added pyridinium p-toluenesulfonate (8.04 g) and the mixture was stirred at 55° C. for 4 hours. To this reaction mixture was added 1N-NaOH (ca. 30 ml) and the solvent was distilled off under reduced pressure. To the residue was added ether (300 ml) and the suspension was dried over anhydrous sodium sulfate. The insolubles were filtered off and the filtrate was concentrated under reduced pressure. The residue was subjected to vacuum distillation to give 42.4 g of 2-[(tetrahydropyran-2-yl)thio]ethanol. bp 93°–94° C. /0.2 mmHg IR(Neat): 3400, 2940, 2860 cm$^{-1}$ $^1$H-NMR (CDCl$_3$) δ: 1.46–2.03 (6H, m), 2.79 (1H, ddd, J=14.8 Hz, 8.2 Hz, 4.2 Hz), 2.91 (1H, ddd, J=14.8 Hz, 5.0 Hz, 3.4 Hz), 3.45–3.91 (4H, m), 4.06–4.18 (1H, m), 4.73 (1H, dd, J=7.8 Hz, 3.2 Hz)

REFERENCE EXAMPLE 18

To a solution of chloroacetic acid (22.7 g) in tetrahydrofuran-DMPU (5:1, 300 ml) was added a solution of butyllithium (0.24 mol) in hexane (150 ml) at −78° C. and the resulting suspension was warmed to room temperature. Separately, a solution of butyllithium (0.24 mol) in hexane (150 ml) was added to a solution of 2-[(tetrahydropyran-2-yl)thio]ethanol (38.9 g) in tetrahydrofuran (200 ml) at −78° C. and this solution was also warmed to room temperature. This solution and the above suspension were pooled and refluxed for 18 hours. After cooling, the reaction mixture was diluted with ice-aqueous sodium chloride solution (water-saturated NaCl solution=3:1, 400 ml) and the unreacted chloroacetic acid was extracted with ether (200 ml×6). The aqueous layer was adjusted to pH 2 with 4N-hydrochloric acid and extracted with ether (200 ml×3). The organic layer was washed successively with aqueous sodium chloride solution (saturated aqueous sodium chloride solution-water=1:1, 200 ml×2) and saturated aqueous sodium chloride solution (100 ml) and dried over anhydrous sodium sulfate. Finally the solvent was distilled off under reduced pressure to give 27.0 g of [2-[(tetrahydropyran-2-yl)thio]ethoxy]acetic acid as a colorless oil.

IR(Neat): 3500–2400, 2950, 2870, 1740, 1440 cm$^{-1}$ $^1$H-NMR (CDCl$_3$) δ: 1.50–2.05 (6H, m), 2.75–3.02 (2H, m), 3.47–3.62 (1H, m), 3.68–3.85 (2H, m), 4.05–4.18 (3H, m), 4.91 (1H, dd, J=6.2 Hz, 3.6 Hz), 6.30 (1H, brs)

REFERENCE EXAMPLE 19

To a solution of [2-[(tetrahydropyran-2-yl)thio]ethoxy]acetic acid (1.54 g) in acetone (35 ml) was added 1N-silver nitrate solution (35 ml) and the mixture was stirred at room temperature for 3 hours. The white precipitate was collected by filtration and washed with water and acetone. The resultant white powder was suspended in dichloromethane (20 ml) and hydrogen sulfide gas was bubbled through the suspension for 15 minutes. The resulting black precipitate was filtered off and the filtrate was concentrated under reduced pressure to give 807 mg of (2-mercaptoethoxy)acetic acid as a colorless oil.

IR(Neat): 3500–2400, 2950, 2560, 1738 cm$^{-1}$ $^1$H-NMR (CDCl$_3$) δ: 1.62 (1H, t, J=8.2 Hz), 2.76 (2H, dt, J=8.2 Hz, 6.2 Hz), 3.72 (2H, t, J=6.2 Hz), 4.20 (2H, s), 8.33 (1H, brs)

REFERENCE EXAMPLE 20

To a solution of (2-mercaptoethoxy)acetic acid (800 mg) in dichloromethane (5 ml) was added a solution of N,N′-dicyclohexylcarbodiimide (1.21 g) in dichloromethane (8 ml) at 0° C. and the mixture was stirred at room temperature for 1 hour. The reaction mixture was diluted with 1N-potassium hydrogen sulfate (6 ml) and stirred for 10 minutes, after which it was filtered through celite to remove the insolubles. The filtrate was washed successively with water, saturated sodium hydrogen carbonate solution and water and dried over anhydrous sodium sulfate. The solvent was then distilled off under reduced pressure and the residue was purified by flash column chromatography (ethyl acetate-hexane=1:5) to give 694 mg of 1,4-oxathian-3-one as a colorless oil.

IR(Neat): 2960, 2870, 1663, 1453, 1420, 1310, 1230, 1125 cm$^{-1}$ $^1$H-NMR (CDCl$_3$) δ: 3.34 (1H, d, J=10.4 Hz), 3.34 (1H, t, J=1.6 Hz), 4.05 (1H, d, J=10.4 Hz), 4.05 (1H, t, J=1.6 Hz), 4.27 (2H, s)

REFERENCE EXAMPLE 21

The procedure of Reference Example 13 was repeated except that 1,4-oxathian-3-one was used in lieu of 1,4-dithian-2-one to give (3S,4S)-3-[(R)-1-[tert-butyldimethylsilyl)oxy]ethyl]-4-[(RS)-3-oxo-1,4-oxathian-2-yl]azetidin-2-one (diastereomer ratio, 1:1).

IR (KBr): 3230, 3100, 2955, 2930, 2900, 2860, 1768, 1720, 1675 cm$^{-1}$

REFERENCE EXAMPLE 22

To a solution of the product compound of Reference Example 21 (3.46 g) in acetonitrile (20 ml) was added boron trifluoride etherate (2.23 ml) at 0° C. and the mixture was stirred at the same temperature for 4 hours. The reaction mixture was then poured in ice-water, adjusted to pH 7.0 and extracted with ethyl acetate. The extract was dried and the solvent was distilled off under reduced pressure. The residue was then purified by silica gel column chromatography (eluent: ethyl acetate). The resulting oil (2.20 g) was dissolved in dichloromethane (35 ml) followed by addition of chlorotrimethylsilane (3.1 g) and pyridine (2.63 g) in that order at 0° C. The mixture was stirred at the same temperature for 1.5 hours. The solvent was then distilled off and ether (50 ml) was added to the residue. The insolubles were filtered off and the solvent was distilled off. To the residue were added ethyl acetate-methanol (1:1, 50 ml) and silica gel (15 g) and the mixture was stirred at room temperature for 5 hours and, then, filtered. The filtrate was concentrated under reduced pressure and the residue was purified by flash column chromatography (packing: silica gel, 50 g; ethyl acetate-hexane=2:3) to give 1.73 g of (3S,4S)-3-[(R)-1-(trimethylsilyloxy)-ethyl]-4-[(RS)-3-oxo-1,4-oxathian-2-yl]azetidin-2-one (diastereomer ratio, 1:1) as a colorless oil.

IR(Neat): 3480, 3200, 2955, 2880, 1760, 1660 cm$^{-1}$

REFERENCE EXAMPLE 23

The compound synthesized in Reference Example 22 was reacted in the same manner as in Reference Example 15 to give allyl [(3S,4S)-2-oxo-4-[(R)-3-oxo-1,4-oxathian-2-yl]-3-[(R)-1-(trimethylsilyloxy)-ethyl]azetidin-1-yl]glyoxylate (R-form) and allyl [(3S,4S)-2-oxo-4-[(S)-3- oxo-1,4-oxathian-2-yl]-3-[(R)-1-(trimethylsilyloxy)-ethyl]azetidin-1-yl]glyoxylate (S-form).

Configuration of thiopyran ring: R
IR(Neat): 2970, 2875, 1805, 1765, 1705, 1668 cm$^{-1}$
Configuration of thiopyran ring: S
IR(Neat): 2950, 2860, 1810, 1755, 1663 cm$^{-1}$

EXAMPLE 1

Allyl (5S,6S,7RS)-5-[(R)-1-(trimethylsilyloxy)-ethyl]-4-oxo-3-aza-11-thiatricyclo[5.4.0.0$^{3,6}$]undec-1-ene-2-carboxylate

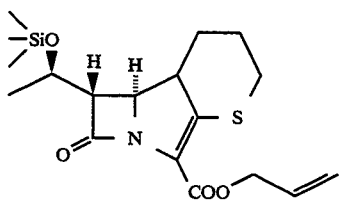

To a toluene solution (3 ml) of the compound of Reference Example 3 (322 mg, the configuration of thiopyran ring, R:S=75:25) were added hydroquinone (3 mg) and triethyl phosphite (647 mg) in the order mentioned and the mixture was stirred at 90° C. for 2 hours and, then, under reflux for 24 hours. The solvent was distilled off under reduced pressure and the residue was purified by flash columnchromatography (packing- :silica gel 15 g; ethyl acetate-hexane 1:6) to give the title compound (212 mg) (diastereomer ratio, 7R:7S=69:31).

IR (KBr): 2955, 1782, 1713, 1660, 1560, 1440, 1370 cm$^{-1}$ 7R-compound: $^1$H-NMR (CDCl$_3$) δ: 0.13 (9H, s), 1.25 (3H, d, J=6.2 Hz), 1.50–2.30 (4H, m), 2.62–2.97 (2H, m), 3.00–3.24 (1H, m), 3.29 (1H, dd, J=6.8 Hz, 4.0 Hz), 4.20 (1H, dq, J=6.2 Hz, 6.2 Hz), 4.24 (1H, dd, J=11.2 Hz, 4.0 Hz), 4.71 (1H, brdd, J=13.4 Hz, 5.4 Hz), 4.80 (1H, brdd, J=13.4 Hz, 5.4 Hz), 5.25 (1H, brd, J=10.6 Hz), 5.45 (1H, brd, J=17.2 Hz), 5.86–6.40 (1H, m) 7S-compound: $^1$H-NMR (CDCl$_3$) δ: 0.13 (9H, s), 1.29 (3H, d, J=6.2 Hz), 1.50–2.30 (4H, m), 2.62–2.97 (2H, m), 3.00–3.24 (1H, m), 3.09 (1H, dd, J=7.4 Hz, 2.2 Hz), 3.64 (1H, dd, J=9.0 Hz, 2.2 Hz), 4.20 (1H, dg, J=6.2 Hz, 6.2 Hz), 4.71 (1H, brdd, J=13.4 Hz, 5.4 Hz), 4.80 (1H, brdd, J=13.4 Hz, 5.4 Hz), 5.25 (1H, brd, J=10.6 Hz), 5.45 (1H, brd, J=17.2 Hz), 5.86–6.40 (1H, m)

EXAMPLE 2

Allyl (5S,6S,7RS)-5-[(R)-1-hydroxyethyl]-4-oxo-3-aza-11-thiatricyclo[5.4.0.0$^{3,6}$]undec-1-ene-2-carboxylate

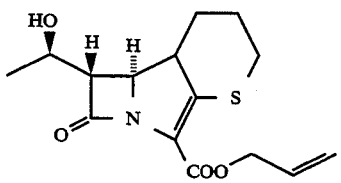

To the compound (208 mg) of Example 1 was added a solution of pyridinium p-toluenesulfonate (1.0 mg) in tetrahydrofuran-water (2:1, 6 ml) at room temperature and the mixture was stirred for 25 minutes. The reaction mixture was diluted with ethyl acetate (30 ml) and water (5 ml) and extracted with ethyl acetate. The organic layer was washed successively with water and saturated aqueous sodium chloride solution and dried over anhydrous sodium sulfate. The solvent was then distilled off under reduced pressure and the residue was purified by flash column chromatography (packing- :silica gel 12 g; ethyl acetate-hexane 3:2) to give the title compound (130 mg) (diastereomer ratio, 7R:7S=66:34)

IR(KBr): 3500, 2975, 2940, 1770, 1693, 1568 cm$^{-1}$
7R-compound:

$^1$H-NMR (CDCl$_3$) δ: 1.32 (3H, d, J=6.4 Hz), 1.50–2.32 (4H, m), 1.79 (1H, brs), 2.62–2.95 (2H, m), 3.03–3.30 (1H, m), 3.32 (1H, dd, J=6.4 Hz, 3.6 Hz), 4.17–4.34 (1H, m), 4.33 (1H, dd, J=10.8 Hz, 3.6 Hz), 4.70 (1H, ddt, J=13.4 Hz, 5.6 Hz, 1.2 Hz), 4.82 (1H, ddt, J=13.4 Hz, 5.6 Hz, 1.2 Hz), 5.26 (1H, brd, J=10.4 Hz), 5.46 (1H, brd, J=17.2 Hz), 5.98 (1H, ddt, J=17.2 Hz, 10.4 Hz, 5.6 Hz)

7S-compound:
$^1$H-NMR (CDCl$_3$) δ: 1.35 (3H, d, J=6.4 Hz), 1.50–2.32 (4H, m), 1.79 (1H, brs), 2.62–2.95 (2H, m), 3.03–3.30 (1H, m), 3.13 (1H, dd, J=6.6 Hz, 2.2 Hz), 3.77 (1H, dd, J=9.4 Hz, 2.2 Hz), 4.17–4.34 (1H, m), 4.70 (1H, ddt, J=13.4 Hz, 5.6 Hz, 1.2 Hz), 4.82 (1H, ddt, J=13.4 Hz, 5.6 Hz, 1.2 Hz), 5.26 (1H, brd, J=10.4 Hz), 5.46 (1H, brd, J=17.2 Hz), 5.98 (1H, ddt, J=17.2 Hz, 10.4 Hz, 5.6 Hz)

EXAMPLE 3

Sodium (5S,6S,7RS)-5-[(R)-1-hydroxyethyl]-4-oxo-3-aza-11-thiatricyclo[5.4.0.0$^{3,6}$]undec-1-ene-2-carboxylate

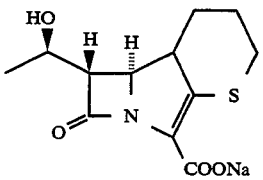

To a solution of the compound of Example 2 (126 mg) in tetrahydrofuran-dichloromethane (1:1, 2 ml) was added a solution of triphenylphosphine (10.7 mg) in tetrahydrofuran-dichloromethane (1:1, 2 ml), followed by addition of a mixed solution of sodium 2-ethylhexanoate (67.6 mg) and tetrakis(triphenylphosphine)palladium (0) (15.7 mg) in tetrahydrofuran-dichloromethane (1:1, 4 ml). The mixture was stirred at room temperature for 30 minutes and, then, anhydrous ether (8 ml) was added. The reaction mixture was cooled to 0° C and the resulting precipitate was collected by filtration and washed with ether-tetrahydrofuran. The white powder thus obtained was dried in vacuo to give the title compound (97 mg) (diastereomer ratio, 7R:7S=70:30).

IR(KBr): 3400, 2970, 2940, 1775, 1608, 1598, 1400 cm$^{-1}$ 7R-compound:
$^1$H-NMR (D$_2$O) δ: 1.27 (3H, d, J=6.4 Hz), 1.40–1.70 (1H, m), 1.90–2.30 (3H, m), 2.60–2.97 (2H, m), 3.15–3.34 (1H, m), 3.50 (1H, dd, J=5.8 Hz, 3.6 Hz), 4.10–4.32 (1H, m), 4.30 (1H, dd, J=5.4 Hz, 3.6 Hz)

7S-compound:
$^1$H-NMR (CDCl$_3$) δ: 1.29 (3H, d, J=6.4 Hz), 1.40–1.70 (1H, m), 1.90–2.30 (3H, m), 2.60–2.97 (2H, m), 3.15–3.34 (1H, m), 3.37 (1H, dd, J=6.0 Hz, 2.2 Hz ), 3.76 (1H, dd, J=9.2 Hz, 2.2 Hz), 4.10–4.32 (1H, m)

EXAMPLE 4

Allyl (5S,6S,7R)-5-[(R)-1-(trimethylsilyloxy)-ethyl]-4-oxo-3-aza-10-thiatricyclo[5.3.0.0³,⁶]dec-1-ene-2-carboxylate

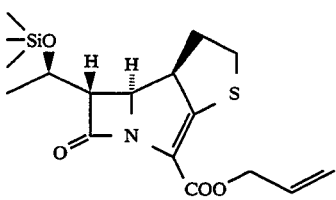

To a toluene solution (6 ml) of the compound of Reference Example 6 (491 mg) were added hydroquinone (4 mg) and triethyl phosphite (1.02 g) in the order mentioned and the mixture was stirred at 90° C. for 2 hours and, then, under reflux for 66 hours. The solvent was distilled off under reduced pressure and the residue was purified by flash column chromatography (packing:silica gel 15 g; ethyl acetate-hexane 1:6) to give the title compound (36 mg ).

IR (Neat): 2975, 1783, 1705, 1660, 1590 cm⁻¹ ¹H-NMR (CDCl₃) δ: 0.13 (9H, s), 1.24 (3H, d, J=6.2 Hz ), 1.70–1.93 (1H, m), 2.14–2.26 (1H, m), 3.40 (1H, dd, J=6.0 Hz, 4.6 Hz), 3.44 (1H, dd, J=11.8 Hz, 6.6 Hz), 3.61 (1H, ddd, J=11.8 Hz, 11.8 Hz, 4.8 Hz), 3.73 (1H, ddd, J=13.4 Hz, 11.0 Hz, 5.8 Hz), 4.20 (1H, qd, J=6.4 Hz, 6.0 Hz), 4.30 (1H, dd, J=11.0 Hz, 4.6 Hz), 4.76 (2H, d, J=6.0 Hz), 5.33 (1H, d, J=10.4 Hz), 5.42 (1H, brd, J=16.8 Hz), 5.97 (1H, ddt, J=16.8 Hz, 10.4 Hz, 6.0 Hz)

EXAMPLE 5

Allyl (5S,6S,7R)-5-[(R)-1-hydroxyethyl]-4-oxo-3-aza-10-thiatricyclo[5.3.0.0³,⁶]dec-1-ene-2-carboxylate

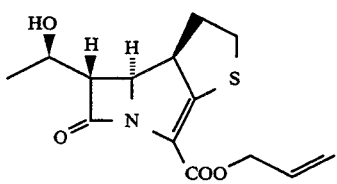

The title compound (14 mg) was produced from the compound (33 mg) of Example 4 in generally the same manner as Example 2

IR (CHCl³): 3300, 1785, 1718, 1600 cm⁻¹ ¹H-NMR (CDCl₃) δ: 1.30 (3H, d, J=6.4 Hz), 1.61 (1H, brs), 1.72–1.94 (1H, m), 2.19–2.32 (1H, m), 3.40 (1H, dd, J=6.0 Hz, 4.6 Hz), 3.44 (1H, dd, J=11.8 Hz, 6.6 Hz), 3.62 (1H, ddd, J=11.8 Hz, 11.8 Hz, 4.8 Hz), 3.77 (1H, ddd, J=13.4 Hz, 11.0 Hz, 4.8 Hz), 4.17–4.32 (1H, m), 4.35 (1H, dd, J=11.0 Hz, 4.6 Hz), 4.71 (1H, ddt, J=14.2 Hz, 5.6 Hz, 1.4 Hz), 4.78 (1H, ddt, J=14.2 Hz, 5.6 Hz, 1.4 Hz), 5.26 (1H, ddd, J=10.4 Hz, 1.4 Hz, 1.4 Hz), 5.44 (1H, ddd, J=17.4 Hz, 1.4 Hz, 1.4 Hz), 5.97 (1H, ddt, J=17.4 Hz, 10.4 Hz, 5.6 Hz)

EXAMPLE 6

Sodium (5S,6S,7R)-5-[(R)-1-hydroxyethyl]-4-oxo-3-aza-10-thiatricyclo[5.3.0.0³,⁶]dec-1-ene-2-carboxylate

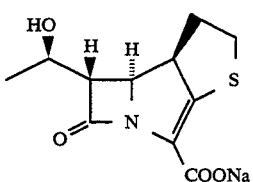

To a solution of the compound of Example 5 (14 mg) in tetrahydrofuran-dichloromethane (1:1, 0.2 ml) was added triphenylphosphine (1.2 mg) followed by addition of a mixed solution of sodium 2-ethylhexanoate (7.9 mg) and tetrakis(triphenylphosphine)palladium (0) (1.8 mg) in tetrahydrofuran-dichloromethane (1:1, 0.2 ml). The mixture was stirred at room temperature for 30 minutes and, then, anhydrous ether (5 ml) was added. The mixture was cooled to 0° C. and the resulting precipitate was collected by centrifugation and washed with ether-tetrahydrofuran. The white powder thus obtained was dried in vacuo to give the title compound (8.5 mg)

IR (KBr): 3440, 2930, 1780, 1620, 1580, 1400 cm⁻¹ ¹H-NMR (D₂) δ: 1.25 (3H, d, J=6.4 Hz), 1.70–1.94 (1H, m), 2.04–2.30 (1H, m), 3.42 (1H, dd, J=11.4 Hz, 7.0 Hz), 3.52–3.68 (2H, m), 3.79 (1H, ddd, J=13.2 Hz, 11.2 Hz, 5.4 Hz), 4.24 (1H, qd, J=6.4 Hz, 6.0 Hz), 4.34 (1H, dd, J=11.2 Hz, 4.2 Hz)

EXAMPLE 7

The stereoisomers of Reference Example 7 were respectively reacted as in Examples 1, 2 and 3 to give the optically active compounds corresponding to the racemic compounds of Examples 1, 2 and 3. The IR data on these compounds are presented below.

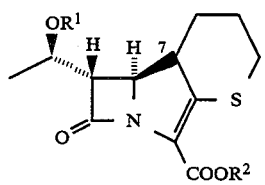

| No. | R¹ | R² | Configuration at 7-position | Appearance | IR(cm⁻¹) |
| --- | --- | --- | --- | --- | --- |
| 1) | SiMe₃ | CH₂CH=CH₂ | R | Oil | (Neat) 2970, 1786, 1718, 1650, 1570 |
| 2) | H | CH₂CH=CH₂ | R | Oil | (Neat) 3480, 2945, 1780, 1700, 1648, 1563 |

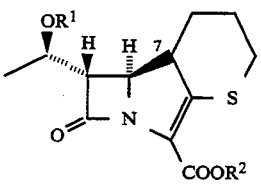

| No. | R¹ | R² | Configuration at 7-position | Appearance | IR(cm⁻¹) |
|---|---|---|---|---|---|
| 3) | H | Na | R | Powder | (KBr) 3400, 2970, 2940, 1772, 1600 1570, 1400 |
| 4) | SiMe₃ | CH₂CH=CH₂ | S | Oil | (Neat) 2950, 2930, 2855, 1755, 1710, 1642, 1550 |
| 5) | H | CH₂CH=CH₂ | S | Needles | (KBr) 3425, 2925, 1765, 1710, 1640, 1550 |
| 6) | H | Na | S | Powder | (KBr) 3400, 2940, 1758, 1590, 1400 |

EXAMPLE 8

Sodium (10S,11R,12S)-12-[(R)-1-hydroxyethyl]-13-oxo-14-azatetracyclo[8.5.0.0$^{2,7}$.0$^{11,14}$]pentadeca-2,4,6,15(1)-tetraene-15-carboxylate

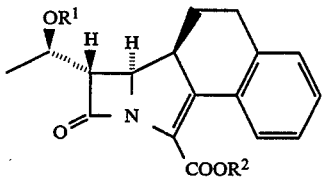

(1) To a solution of allyl [(3S,4R)-2-oxo-4-[(R)-1,2,3,4-tetrahydro-1-oxonaphthalen-2-yl]-3-[(R)-1-(trimethylsilyloxy)-ethyl]azetidin-1-yl]glyoxylate (530 mg) in toluene (12 ml) were added hydroquinone (5 mg) and triethyl phosphite (993 mg) in the order mentioned and the mixture was stirred at 90° C. for 2 hours and, then, under reflux for 42 hours. The solvent was distilled off under reduced pressure and the residue was purified by flash column chromatography (packing: silica gel 20 g; ethyl acetate-hexane 1:10) to give 229 mg of allyl (10S,11R,12S)-12-[(R)-1-(trimethylsilyloxy)-ethyl]-13-oxo-14-azatetracyclo[8.5.0.0$^{2,7}$0$^{11,14}$]pentadeca-2,4,6,15(1)-tetraene-15-carboxylate (R¹=SiMe₃, R²=CH₂CH=CH₂) as colorless needles. m.p.: 122°–125° C.

IR (KBr): 2960, 1770, 1730, 1643, 1605 cm⁻¹ ¹H-NMR (CDCl₃) δ: 0.15 (9H, s), 1.28 (3H, d, J=6.2 Hz), 1.75–2.20 (2H, m), 3.07 (2H, dd, J=8.8 Hz, 3.4 Hz), 3.19 (1H, ddd, J=13.8 Hz, 10.2 Hz, 4.0 Hz), 3.29 (1H, dd, J=6.4 Hz, 3.4 Hz), 4.25 (1H, qd, J=6.4 Hz, 6.2 Hz), 4.28 (1H, dd, J=10.2 Hz, 3.4 Hz), 4.73 (1H, ddt, J=13.4 Hz, 5.8 Hz, 1.4 Hz), 4.82 (1H, ddt, J=13.4 Hz , 5.8 Hz, 1.4 Hz), 5.26 (1H, ddd, J=10.4 Hz, 2.6 Hz, 1.4 Hz), 5.41 (1H, ddd, J=17.2 Hz, 2.6 Hz, 1.4 Hz), 5.98 (1H, ddt, J=17.2 Hz, 10.4 Hz, 5.8 Hz), 7.09–7.26 (3H, m), 7.76 (1H, dd, J=7.4 Hz, 1.8 Hz)

(2) To a solution of the compound prepared according to (1) (219 mg) in THF-water (2:1, 7 ml) was added a solution of pyridinium p-toluenesulfonate (0.9 mg) in THF-water (2:1, 1 ml) at room temperature and the mixture was stirred for 1 hour. The reaction mixture was diluted with ethyl acetate (40 ml) and water (10 ml) and extracted with ethyl acetate. The organic layer was washed successively with water and aqueous sodium chloride solution and dried over anhydrous sodium sulfate. The solvent was then distilled off under reduced pressure and the residue was purified by silica gel column chromatography (ethyl acetate-hexane 2:3) to give 153 mg of allyl (10S,11R,12S)-12-[(R)-1-hydroxyethyl]-13-oxo-14-azatetracyclo-[8.5.0.0$^{2,7}$.0$^{11,14}$]pentadeca-2,4,6,15(1)-tetraene-15-carboxylate (R¹=H, R²=CH₂CH=CH₂) as colorless prisms. m.p. 133°–134° C.

IR (KBr): 3460, 2945, 1790, 1723, 1648, 1600 cm⁻¹ ¹H-NMR (CDCl₃) δ: 1.37 (3H, d, J=6.2 Hz), 1.77 (1H, d, J=4.8 Hz), 1.80–2.20 (2H, m), 3.04–3.14 (2H, m), 3.23 (1H, ddd, J=13.6 Hz, 10.4 Hz, 4.0 Hz), 3.33 (1H, dd, J=6.6 Hz, 3.4 Hz), 4.20–4.36 (1H), 4.35 (1H, dd, J=10.4 Hz, 3.4 Hz), 4.73 (1H, ddt, J=13.2 Hz, 5.8 Hz, 1.4 Hz), 4.84 (1H, ddt, J=13.2 Hz, 5.8 Hz, 1.4 Hz, 5.27 (1H, ddd, J=10.4 Hz, 2.6 Hz, 1.4 Hz), 5.41 (1H, ddd, J=17.2 Hz, 2.6 Hz, 1.4 Hz), 5.98 (1H, ddt, J=17.2 Hz, 10.4 Hz, 5.8 Hz), 7.09–7.30 (3H, m), 7.77 (1H, dd, J=7.8 Hz, 1.8 Hz)

(3) To a solution of the compound prepared according to (2) in THF-dichloromethane (1:1, 2.5 ml) was added triphenylphosphine (11.5 mg) followed by addition of a mixed solution of sodium 2-ethylhexanoate (73 mg) and tetrakis(triphenylphosphine)palladium (0) (16.9 mg) in THF-dichloromethane (1:1, 3.31 ml). The mixture was stirred at room temperature for 30 minutes, at the end of which time anhydrous ether (15 ml) was added. The mixture was cooled to 0° C. and the resulting precipitate was collected by filtration and washed with ether-THF. The powder thus obtained was purified by Diaion CHP-20 column chromatography (aq. MeOH, 0→5% ) and freeze-dried to give 115 mg of the title compound (R¹=H, R²=Na) as powder.

IR (KBr): 3400, 2930, 1750, 1588, 1390 cm⁻¹ ¹H-NMR (D₂O) δ: 1.31 (3H, d, J=6.4 Hz), 1.72–1.96 (1H, m), 2.14 (1H, ddd, J=12.2 Hz, 7.4 Hz, 3.8 Hz), 2.98–3.08 (2H, m), 3.26 (1H, ddd, J=13.6 Hz, 10.6 Hz, 3.8 Hz), 3.58 (1H, dd, J=5.6 Hz, 3.6 Hz), 4.28 (1H, qd, J=6.4 Hz, 5.6 Hz), 4.38 (1H, dd, J=10.6 Hz, 3.6 Hz), 7.10–7.27 (3H, m), 7.46 (1H, d, J=7.4 Hz)

EXAMPLE 9

Sodium (10R,11R,12S)-12-[(R)-1-hydroxyethyl]-13-oxo-14-azatetracyclo[8.5.0.0$^{2,7}$.0$^{11,14}$]pentadeca-2,4,6,15(1)-tetraene-15-carboxylate

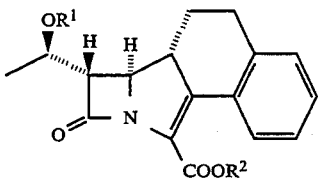

The following compounds were produced in generally the same manner as in Example 8. (1) Allyl (10R,11R,12S)-12-[(R)-1-(trimethylsilyloxy)ethyl]-13-oxo-14-azatetracyclo[8.5.0.0$^{2,7}$.0$^{11,14}$]pentadeca-2,4,6,15(1)-tetraene-15-carboxylate (R$^1$=SiMe$_3$, R$^2$=CH$_2$CH=CH$_2$)

IR (Neat): 2960, 2940, 1772, 1710, 1650, 1600 cm$^{-1}$ 1H-NMR (CDCl$_3$) δ: 0.16 (9H, m), 1.31 (3H, d, J=6.2 Hz), 1.74–2.04 (1H, m), 2.17–2.32 (1H, m), 2.99 (2H, dd, J=8.6 Hz, 4.0 Hz), 3.21 (1H, dd, J=7.2 Hz, 2.6 Hz), 3.30 (1H, ddd, J=12.4 Hz, 8.0 Hz, 4.8 Hz), 3.74 (1H, dd, J=8.0 Hz, 2.6 Hz), 4.21 (1H, dd, J=7.2 Hz, 6.2 Hz), 4.74 (1H, ddt, J=13.6 Hz, 5.6 Hz, 1.4 Hz), 4.83 (1H, ddt, J=13.6 Hz, 5.6 Hz, 1.4 Hz), 5.27 (1H, ddd, J=10.6 Hz, 2.8 Hz, 1.4 Hz), 5.47 (1H, ddd, J=17.2 Hz, 2.8 Hz, 1.4 Hz), 6.00 (1H, ddt, J=17.2 Hz, 10.6 Hz, 5.6 Hz), 7.12–7.33 (3H, m), 8.46 (1H, dd, J=8.0 Hz, 1.8 Hz)

(2) Allyl (10R,11R,12S)-12-[(R)-1-hydroxyethyl]-13-oxo-14-azatetracyclo[8.5.0.0$^{2,7}$.0$^{11,14}$]pentadeca-2,4,6,15(1)-tetraene-15-carboxylate (R$^1$=H, R$^2$=CH$_2$CH=CH$_2$) m.p.: 93°–95° C.

IR (KBr): 3460, 2945, 1790, 1723, 1648, 1600 cm$^{-1}$ 1H-NMR (CDCl$_3$) δ: 1.38 (3H, d, J=6.2 Hz), 1.80 (1H, brs), 1.80–2.06 (1H, m), 2.28 (1H, ddd, J=12.8 Hz, 8.8 Hz, 4.4 Hz), 3.00 (2H, dd, J=8.8 Hz, 4.4 Hz), 3.26 (1H, dd, J=6.4 Hz, 2.6 Hz), 3.32 (1H, ddd, J=12.8 Hz, 8.2 Hz, 4.6 Hz), 3.84 (1H, dd, J=8.2 Hz, 2.6 Hz), 4.20–4.37 (1H, m), 4.75 (1H, ddt, J=13.4 Hz, 5.6 Hz, 1.4 Hz), 4.85 (1H, ddt, J=13.4 Hz, 5.6 Hz, 1.4 Hz), 5.28 (1H, ddd, J=10.8 Hz, 2.6 Hz, 1.4 Hz), 5.46 (1H, ddd, J=17.2 Hz, 2.6 Hz, 1.4 Hz), 6.00 (1H, ddt, J=17.2 Hz, 10.8 Hz, 5.6 Hz), 7.10–7.35 (3H, m), 8.44 (1H, dd, J=8.6 Hz, 1.6 Hz)

(3) Title compound (R$^1$=H, R$^2$=Na)

IR (KBr): 3400, 2940, 1755, 1590, 1400 cm−1 1H-NMR (D$_2$O) δ: 1.33 (3H, d, J=6.2 Hz), 1.66–1.93 (1H, m), 2.22–2.38 (1H, m), 2.96 (2H, dd, J=8.2 Hz, 3.6 Hz), 3.39 (1H, ddd, J=13.0 Hz, 8.4 Hz, 4.4 Hz), 3.49 (1H, dd, J=5.6 Hz, 2.2 Hz), 3.90 (1H, dd J=8.4 Hz, 3.6 Hz), 4.27 (1H, qd, J=6.2 Hz, 5.6 Hz), 7.15–7.22 (3H, m), 7.96 (1H, d, J=6.6 Hz)

EXAMPLE 10

Sodium (5S,6R,7S)-5-[(R)-1-hydroxyethyl]-4-oxo-3-azatricyclo[5.4.0.0$^{3,6}$]undec-1-ene-2-carboxylate

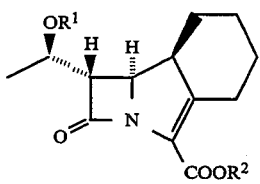

The following compounds were produced in generally the same manner as in Example 8.

(1) Allyl (5S,6R,7S)-5-[(R)-1-(trimethylsilyloxy)ethyl]-4-oxo-3-azatricyclo[5.4.0.0$^{3,6}$]undec-1-ene-2-carboxylate (R$^1$=SiMe$_3$, R$^2$=CH$_2$CH=CH$_2$)

IR (Neat): 2930, 2860, 1780, 1720, 1635 cm$^{-1}$ 1H-NMR (CDCl$_3$) δ: 0.13 (9H, s), 1.26 (3H, d, J=6.0 Hz), 1.2–2.2 (7H, m), 2.7–2.9 (1H, m), 3.16 (1H, dd, J=3.2 & 6.8 Hz), 3.4–3.5 (1H, m), 4.08 (1H, dd, J=3.2 & 10.2 Hz), 4.18 (1H, dq, J=6.8 & 6.0 Hz), 4.67 (1H, ddt, J=5.5, 13.6 & 1.4 Hz), 4.80 (1H, ddt, J=5.5, 13.6 & 1.4 Hz), 5.25 (1H, dq, J=10.4 & 1.4 Hz), 5.43 (1H, dq, J=17.2 & 1.4 Hz), 5.97 (1H, ddt, J=10.4, 17.2 & 5.5 Hz)

(2) Allyl (5S,6R,7S)-5-[(R)-1-hydroxyethyl]-4-oxo-3-azatricyclo[5.4.0.0$^{3,6}$]undec-1-ene-2-carboxylate (R$^1$=H, R$^2$=CH$_2$CH=CH$_2$)

IR (Neat): 3480, 2930, 2860, 1755, 1715, 163.0 cm$^{-1}$ 1H-NMR (CDCl$_3$) δ: 1.33 (3H, d, J=6.2 Hz), 1.2–2.2 (7H, m), 1.74 (1H, d, J=4.8 Hz), 2.8–2.9 (1H, m), 3.21 (1H, dd, J=3 & 6.6 Hz), 3.4–3.5 (1H, m), 4.18 (1H, dd, J=3 & 10.2 Hz), 4.24 (1H, ddq, J=4.8, 6.6 & 6.2 Hz), 4.68 (1H, ddt, J=5.5, 13.4 & 1.5 Hz), 4.81 (1H, ddt, J=5.5, 13.4 & 1.5 Hz), 5.26 (1H, dq, J=10.4 & 1.5 Hz), 5.42 (1H, dq, J=17.2 & 1.5 Hz), 5.98 (1H, ddt, J=10.4, 17.2 & 5.5 Hz)

Title compound (R$^1$=H, R$^2$=Na)

IR (KBr): 3410, 2900, 2830, 1740, 1630, 1580 cm$^{-1}$ 1H-NMR (D$_2$O) δ: 1.28 (3H, d, J=6.6 Hz), 1.2–2.2 (7H, m), 2.8–3.0 (1H, m), 3.1–3.3 (1H, m), 3.34 (1H, dd, J=3 & 6.2 Hz), 4.13 (1H, dd, J=3 & 10 Hz), 4.23 (1H, dq, J=6.2 & 6.6 Hz) Analysis:

|  | C | H | N |
| --- | --- | --- | --- |
| Calcd. for C$_{13}$H$_{16}$NNaO$_4$.H$_2$O: | 53.61 | 6.23 | 4.81 |
| Found: | 53.73 | 6.11 | 4.66 |

EXAMPLE 11

Sodium (5S,6R,7R)-5-[(R)-1-hydroxyethyl]-4-oxo-3-azatricyclo[5.4.0.0$^{3,6}$]undec-1-ene-2-carboxylate and derivatives thereof

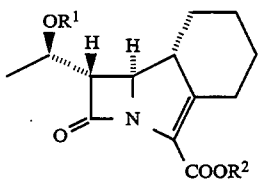

The following compounds were produced in the same manner as in Example 8.

(1) Allyl (5S,6R,7R)-5-[(R)-1-(trimethylsilyloxy)ethyl]-4-oxo-3-azatricyclo[5.4.0.0$^{3,6}$]undec-1-ene-2-carboxylate (R$^1$=SiMe$_3$, R$^2$=CH$_2$CH=CH$_2$)

IR (Neat): 2930, 2860, 1780, 1715, 1630 cm$^{-1}$ 1H-NMR (CDCl$_3$) δ: 0.13 (9H, s), 1.27 (3H, d, J=6.2 Hz), 1.3–2.2 (7H, m), 2.8–2.9 (1H, m), 3.08 (1H, dd, J=2.8 & 7.6 Hz), 3.4–3.5 (1H, m), 3.60 (1H, dd, J=2.8 & 7.6 Hz), 4.15 (1H, dq, J=7.6 & 6.2 Hz), 4.66 (1H, ddt, J=5.5, 13.5 & 1.4 Hz), 4.80 (1H, ddt, J=5.5, 13.5 & 1.4 Hz), 5.25 (1H, dq, J=10.4 & 1.4 Hz), 5.43 (1H, dq, J=17.2 & 1.4 Hz), 5.97 (1H, ddt, J=10.4, 17.2 & 5.5 Hz)

(2) Allyl (5S,6R,7R)-5-[(R)-1-hydroxyethyl]-4-oxo-3-azatricyclo[5.4.0.0$^{3,6}$]undec-1-ene-2-carboxylate m.p. 120°–121° C.

IR (KBr): 3430, 2930, 2850, 1765, 1720, 1630 cm$^{-1}$
1H-NMR (CDCl$_3$) δ: 1.33 (3H, d, J=6.2 Hz), 1.2–2.3 (7H, m), 1.76 (1H, d, J=4.8 Hz), 2.8–3.0 (1H, m), 3.13 (1H, dd, J=2.8 & 6.6 Hz), 3.4–3.5 (1H, m), 3.71 (1H, dd, J=2.8 & 7.6 Hz), 4.22 (1H, ddq, J=4.8, 6.6 & 6.2 Hz), 4.68 (1H, ddt, J=5.5, 13.4 & 1.5 Hz), 4.81 (1H, ddt, J=5.5, 13.4 & 1.5 Hz), 5.26 (1H, dq, J=10.4 & 1.5 Hz), 5.42 (1H, dq, J=17.5 & 1.5 Hz), 5.98 (1H, ddt, J=10.4, 17.2 & 5.5 Hz) Analysis:

|  | C | H | N |
|---|---|---|---|
| Calcd. for C$_{15}$H$_{21}$NO$_4$: | 65.96 | 7.27 | 4.81 |
| Found: | 66.00 | 7.40 | 4.66 |

(3) Title compound (R$^1$=H, R$^2$=Na)
IR (KBr): 3430, 2920, 2850, 1745, 1630, 1590 cm$^{-1}$
1H-NMR (CDCl$_3$) δ: 1.28 (3H, d, J=6.4 Hz), 1.2–2.2 (7H, m), 2.9–3.2 (2H, m), 3.34 (1H, dd, J=2.6 & 5.8 Hz), 3.69 (1H, dd, J=2.6 & 7.4 Hz), 4.21 (1H, dq, J=5.8 & 6.4 Hz) Analysis:

|  | C | H | N |
|---|---|---|---|
| Calcd. for C$_{13}$H$_{16}$NNaO$_4$.H$_2$O: | 53.61 | 6.23 | 4.81 |
| Found: | 53.70 | 6.20 | 4.68 |

EXAMPLE 12

Sodium (5S,6R,7S)-5-[(R)-1-hydroxyethyl]-4-oxo-3-azatricyclo[5.5.0.0$^{3,6}$]dodec-1-ene-2-carboxylate

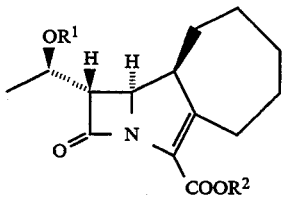

The following compounds were produced in generally the same manner as in Example 8.

(1) Allyl (5S,6R,7S)-5-[(R)-1-(trimethylsilyloxy)ethyl]-4-oxo-3-azatricyclo[5.5.0.0$^{3,6}$]dodec-1-ene-2-carboxylate (R$^1$=SiMe$_3$, R$^2$=CH$_2$CH=CH$_2$)
IR (Neat): 2920, 2850, 1780, 1715, 1650, 1610 cm$^{-1}$
1H-NMR (CDCl$_3$) δ: 0.13 (9H, s), 1.27 (3H, d, J=6.2 Hz), 1.2–2.2 (8H, m), 2.6–3.2 (3H, m), 3.23 (1H, dd, J=3.2 & 7.0 Hz), 4.10 (1H, dd, J3.2 & 10.3 Hz), 4.18 (1H, dq, J=7.0 & 6.2 Hz), 4.67 (1H, ddt, J=5.4, 13.6 & 1.5 Hz), 4.80 (1H, ddt, J=5.4, 13.6 & 1.5 Hz), 5.25 (1H, dq, J=10.4 & 1.5 Hz), 5.44 (1H, dq, J=17.2 & 1.5 Hz), 5.98 (1H, ddt, J=10.4, 17.2 & 5.4 Hz)

(2) Allyl (5S,6R,7S)-5-[(R)-1-hydroxyethyl]-4-oxo-3-azatricyclo[5.5.0.0$^{3,6}$]dodec-1-ene-2-carboxylate (R$^1$=H, R$^2$=CH$_2$CH=CH$_2$) m.p.: 75°–79° C.
IR (KBr): 3410, 2960, 2920, 2850, 1755, 1710, 1610 cm$^{-1}$ 1H-NMR (CDCl$_3$) δ: 1.34 (3H, d, J=6.2 Hz), 1.2–2.0 (8H, m), 1.74 (1H, d, J=4.8 Hz), 2.6–3.2 (3H, m), 3.28 (1H, dd, J=3.0 & 6.8 Hz), 4.19 (1H, dd, J=3.0 & 10.2 Hz), 4.25 (1H, ddq, J=4.8, 6.6 & 6.2 Hz), 4.67 (1H, ddt, J=5.4, 13.4 & 1.5 Hz), 4.82 (1H, ddt, J=5.4, 13.4 & 1.5 Hz), 5.26 (1H, dq, J=10.6 & 1.5 Hz), 5.44 (1H, dq, J=17.2 & 1.5 Hz), 5.98 (1H, ddt, J=10.6, 17.2 & 5.4 Hz) Analysis:

|  | C | H | N |
|---|---|---|---|
| Calcd. for C$_{17}$H$_{23}$NO$_4$: | 66.86 | 7.59 | 4.59 |
| Found: | 66.92 | 7.78 | 4.32 |

(3) Title compound (R$^1$=H, R$^2$=Na)
IR (KBr): 3420, 2920, 2850, 1745, 1615, 1580 cm$^{-1}$
1H-NMR (D$_2$O) δ: 1.29 (3H, d, J=6.4 Hz), 1.2–2.0 (8H, m), 2.4–2.6 (1H, m), 2.8–3.0 (1H, m), 3.1–3.3 (1H, m), 3.38 (1H, dd, J=2.7 & 6.1 Hz), 4.12 (1H, dd, J=2.7 & 9.9 Hz), 4.23 (1H, dq, J=6.1 & 6.4 Hz), Analysis:

|  | C | H | N |
|---|---|---|---|
| Calcd. for C$_{14}$H$_{18}$NNaO$_4$.H$_2$O: | 55.08 | 6.60 | 4.59 |
| Found: | 55.24 | 6.69 | 4.38 |

EXAMPLE 13

Sodium (5S,6R,7R)-5-[(R)-1-hydroxyethyl]-4-oxo-3-azatricyclo[5.5.0.0$^{3,6}$]dodec-1-ene-2-carboxylate

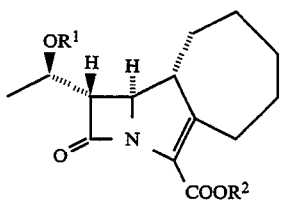

The following compounds were produced in generally the same manner as in Example 8.

(1) Allyl (5S,6R,7R)-5-[(R)-1-(trimethylsilyloxy)ethyl]-4-oxo-3-azatricyclo[5.5.0.0$^{3,6}$]dodec-1-ene-2-carboxylate (R$^1$=SiMe$_3$, R$^2$=CH$_2$CH=CH$_2$)
IR (Neat): 2920, 2850, 1770, 1705, 1645, 1610 cm$^{-1}$
1H-NMR (CDCl$_3$) δ: 0.14 (9H, s), 1.29 (3H, d, J=6.2 Hz), 1.4–1.9 (8H, m), 2.8–2.9 (2H, m), 3.07 (1H, dd, J=2.4 & 7.8 Hz), 3.1–3.3 (1H, m), 3.58 (1H, dd, J=2.4 & 8.8 Hz), 4.14 (1H, dq, J=7.8 & 6.2 Hz), 4.66 (1H, ddt, J=5.4, 13.6 & 1.5 Hz), 4.80 (1H, ddt, J=5.4, 13.6 & 1.5 Hz), 5.25 (1H, dq, J=10.4 & 1.5 Hz), 5.44 (1H, dq, J=17.2 & 1.5 Hz), 5.97 (1H, ddt, J=10.4, 17.2 & 5.4 Hz)

(2) Allyl (5S,6R,7R)-5-[(R)-1-hydroxyethyl]-4-oxo-3-azatricyclo[5.5.0.0$^{3,6}$]dodec-1-ene-2-carboxylate (R$^1$=H, R$^2$=CH$_2$CH=CH$_2$) m.p.: 86°–88° C.
IR (KBr): 3410, 2920, 2850, 1760, 1720, 1610 cm$^{-1}$
1H-NMR (CDCl$_3$) δ: 1.35 (3H, d, J=6.4 Hz), 1.4–2.8 (8H, m), 1.78 (1H, d, J=5.0 Hz), 2.7–2.9 (2H, m), 3.12 (1H, dd, J=2.4 & 6.80Hz ), 3.1–3.3 (1H, m), 3.69 (1H, dd, J=2.4 & 8.8 Hz), 4.22 (1H, ddq, J=5.0, 6.8 & 6.2 Hz), 4.66 (1H, ddt, J=5.4, 13.4 & 1.5 Hz), 4.81 (1H, ddt, J=5.4, 13.4 & 1.5 Hz), 5.26 (1H, dq, J=10.4 & 1.5 Hz), 5.44 (1H, dq, J=17.2 & 1.5 Hz), 5.98 (1H, ddt, J=10.4, 17.2 & 5.4 Hz) Analysis:

|  | C | H | N |
|---|---|---|---|
| Calcd. for C$_{17}$H$_{23}$NO$_4$.0.1 H$_2$O: | 66.47 | 7.61 | 4.56 |
| Found: | 66.47 | 7.67 | 4.51 |

(3) Title compound (R$^1$=H, R$^2$=Na)
IR (KBr): 3420, 2920, 2850, 1745, 1590 cm$^{-1}$ 1H-NMR (D$_2$) δ: 1.29 (3 H, d, J=6.4 Hz), 1.2–2.0 (8H, m), 2.5–2.9 (2H, m), 3.31 (1H, dd, J=2.2 & 6.0 Hz), 3.3–3.4

(1H, m), 3.71 (1H, dd, J=2.2 & 9.0 Hz), 4.21 (1H, dd, J=6.0 & 6.4 Hz) Analysis

|  | C | H | N |
|---|---|---|---|
| Calcd. for C$_{14}$H$_{18}$NNaO$_4$.1.3 H$_2$O: | 54.04 | 6.67 | 4.50 |
| Found: | 53.73 | 6.47 | 4.88 |

EXAMPLE 14

Sodium (5S,6R,7S)-5-[(R)-1-hydroxyethyl]-4-oxo-3-azatricyclo[5.4.0.0$_{3,6}$]undeca-1,10-diene-2-carboxylate

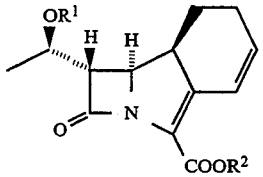

The following compounds were produced in generally the same manner as in Example 8.

(1) Allyl (5S,6R,7S)-5-[(R)-1-(trimethylsilyloxy)ethyl]-4-oxo-3-azatricyclo[5.4.0.0$^{3,6}$]undeca-1,10-diene-2-carboxylate ((R$^1$=SiMe$_3$, R$^2$=CH$_2$CH=CH$_2$) m.p.: 80°–90° C.

IR(KBr): 2960, 1780, 1710, 1602, 1575 cm$^{-1}$ $^1$H-NMR (CDCl$_3$) δ: 0.14 (9H, s), 1.24 (3H, d, J=6.2 Hz), 1.60–1.80 (1H, m), 1.90–2.03 (1H, m), 2.33–2.45 (2H, m), 3.16 (1H, ddd, J=13.4 Hz, 11.2 Hz, 4.6 Hz), 3.29 (1H, dd, J=6.0 Hz, 4.4 Hz), 4.21 (1H, dq, J=6.2 Hz, 6.0 Hz), 4.26 (1H, dd, J=11.2 Hz, 4.4 Hz), 4.17 (1H, ddt, J=13.4 Hz, 5.8 Hz, 1.4 Hz), 4.82 (1H, ddt, J=13.4 Hz, 5.8 Hz, 1.4 Hz), 5.26 (1H, ddd, J=10.4 Hz, 2.6 Hz, 1.4 Hz), 5.43 (1H, ddd, J=17.2 Hz, 2.6 Hz, 1.4 Hz), 5.98 (1H, ddt, J=17.2 Hz, 10.4 Hz, 5.8 Hz), 6.02–6.10 (1H, m), 6.96 (1H, dt, J=10.0 Hz, 2.0 Hz)

(2) Allyl (5S,6R,7S)-5-[(R)-1-hydroxyethyl]-4-oxo-3-azatricyclo[5.4.0.0$^{3,6}$]undeca-1,10-diene-2-carboxylate (R$^1$=H, R$^2$=CH$_2$CH=CH$_2$)

IR (Neat): 3450, 2940, 1775, 1710, 1650, 1618, 1580, 1543 cm$^{-1}$ $^1$H-NMR (CDCl$_3$) δ: 1.32 (3H, d, J=6.4 Hz), 1.63–1.77 (2H, m), 2.00 (1H, ddd, J=12.0 Hz, 7.0 Hz, 3.0 Hz, 3.0 Hz), 2.34–2.47 (2H, m), 3.19 (1H, ddd, J=14.0 Hz, 11.2 Hz, 3.6 Hz), 3.33 (1H, dd, J=6.2 Hz, 4.0 Hz), 4.18–4.34 (1H, m), 4.32 (1H, dd, J=11.2 Hz, 4.0 Hz), 4.71 (1H, ddt, J=13.4 Hz, 5.6 Hz, 1.4 Hz), 4.83 (1H, ddt, J=13.4 Hz, 5.8 Hz, 1.4 Hz), 5.26 (1H, ddd, J=10.2 Hz, 3.0 Hz, 1.6 Hz), 5.42 (1H, ddd, J=17.4 Hz, 3.0 Hz, 1.6 Hz), 5.98 (1H, ddt, J=17.4 Hz, 10.2 Hz, 5.8 Hz), 6.07 (1H, dt, J=10.0 Hz, 4.4 Hz), 6.97 (1H, dt, J=10.0 Hz, 1.8 Hz)

(3) Title compound (R$^1$=H, R$^2$=Na)

IR (KBr): 3410, 2930, 1760, 1598, 1570, 1405, 1380 cm$^{-1}$ $^1$H-NMR (D$^2$O) δ: 1.27 (3H, d, J=6.4 Hz), 1.53–1.80 (1H, m), 1.94–2.08 (1H, m), 2.30–2.42 (2H, m), 3.21 (1H, ddd, J=14.4 Hz, 11.0 Hz, 4.2 Hz), 3.51 (1H, dd, J=5.2 Hz, 4.0 Hz), 4.25 (1H, qd, J=6.4 Hz, 5.2 Hz), 4.29 (1H, dd, J=11.0 Hz, 4.0 Hz), 6.03 (1H, dt, J=10.2 Hz, 4.0 Hz), 6.79 (1H, d, J=10.2 Hz) Analysis:

|  | C | H | N |
|---|---|---|---|
| Calcd. for C$_{13}$H$_{14}$NNaO$_4$.1.2 H$_2$O: | 53.31 | 5.64 | 4.78 |
| Found: | 53.40 | 5.56 | 5.07 |

EXAMPLE 15

Sodium (5S,6R,7R)-5-[(R)-1-hydroxyethyl]-4-oxo-3-azatricyclo[5.4.0.0$^{3,6}$]undeca-1,10-diene-2-carboxylate

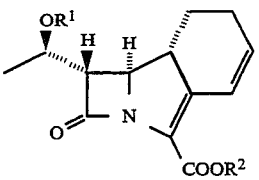

The following compounds were produced in generally the same manner as in Example 8.

(1) Allyl (5S,6R,7R)-5-[(R)-1-(trimethylsilyloxy)ethyl]-4-oxo-3-azatricyclo[5.4.0.0$^{3,6}$]undeca-1,10-diene-2-carboxylate (R$^1$=SiMe$_3$, R$^2$=CH$_2$CH=CH$_2$)

IR (Neat): 2950, 1775, 1715, 1660, 1608, 1578 cm$^{-1}$ $^1$H-NMR (CDCl$_3$) δ: 0.14 (9H, s), 1.30 (3H, d, J=6.0 Hz), 1.60–1.80 (1H, m), 2.07–2.23 (1H, m), 2.27–2.42 (2H, m), 3.08–3.38 (1H, m), 3.11 (1H, dd, J=7.6 Hz, 2.4 Hz), 3.68 (1H, dd, J=9.2 Hz, 2.4 Hz), 4.16 (1H, dq, J=7.6 Hz, 6.0 Hz), 4.70–4.82 (2H, m), 5.26 (1H, ddd, J=10.2 Hz, 1.4 Hz, 0.8 Hz), 5.42 (1H, ddd, J=17.4 Hz, 1.4 Hz 0.8 Hz), 5.97 (1H, ddt, J=17.4 Hz, 10.2 Hz, 5.4 Hz), 6.21 (1H, ddd, J=10.2 Hz, 4.6 Hz, 3.6 Hz), 6.97 (1H, dt, 10.2 Hz, 1.8 Hz)

(2) Allyl (5S,6R,7R)-5-[(R)-1-hydroxyethyl]-4-oxo-3-azatricyclo[5.4.0.0$^{3,6}$]undeca-1,10-diene-2-carboxylate (R$^1$=H, R$^2$CH$_2$CH=CH$_2$) m.p.: 109°–110° C.

IR (KBr): 3410, 2920, 1767, 1718, 1645, 1608, 1580 cm$^{-1}$ $^1$H-NMR (CDCl$_3$) δ: 1.36 (3H, d, J=6.2 Hz), 1.62–1.84 (2H, m), 2.10–2.25 (1H, m), 2.30–2.42 (2H, m), 3.15 (1H, dd, J=6.8 Hz), 3.18 (1H, ddd, J=13.2 Hz, 9.2 Hz, 4.0 Hz), 3.80 (1H, dd, J=9.2 Hz, 2.4 Hz), 4.14–4.22 (1H, m), 4.70 (1H, ddt, J=13.4 Hz, 5.6 Hz, 1.4 Hz), 4.80 (1H, ddt, J=13.4 Hz, 5.6 Hz, 1.4 Hz), 5.26 (1H, ddd, J=10.4 Hz, 2.8 Hz, 1.4 Hz), 5.42 (1H, ddd, J=17.2 Hz, 2.8 Hz, 1.4 Hz), 5.97 (1H, ddt, J=17.2 Hz, 10.4 Hz, 5.6 Hz), 6.17–6.28 (1H, m), 6.98 (1H, dt, J=10.2 Hz, 1.6 Hz)

(3) Title compound (R$^1$=H, R$^2$=Na)

IR (KBr): 3400, 2930, 1745, 1570, 1408, 1380 cm$^{-1}$ $^1$H-NMR (CDCl$_3$) δ: 1.31 (3H, d, J=6.4 Hz), 1.54–1.77 (1H, m), 2.10–2.26 (1H, m), 2.26–2.40 (2H, m), 3.29 (1H, ddd, J=14.4 Hz, 9.2 Hz, 4.0 Hz), 3.37 (1H, dd, J=6.2 Hz, 2.2 Hz), 3.79 (1H, dd, J=9.2 Hz, 2.2 Hz), 4.23 (1H, qd, J=6.4 Hz, 6.2 Hz), 6.23 (1H, dt, J=10.2 Hz, 3.6 Hz), 6.86 (1H, d, J=10.2 Hz) Analysis:

|  | C | H | N |
|---|---|---|---|
| Calcd. for C$_{13}$H$_{14}$NNaO$_4$.1.5 H$_2$O: | 52.35 | 5.74 | 4.70 |
| Found: | 51.96 | 5.36 | 5.03 |

EXAMPLE 16

Sodium (5S,6S,7S )-5-[(R)-1-hydroxyethyl]-4-oxo-9-thia-3-azatricyclo[5.4.0.0$^{3,6}$]undec-1-ene-2-carboxylate

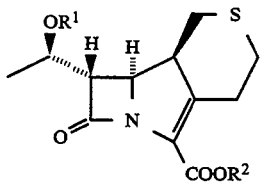

The following compounds were produced in generally the same manner as in Example 8.

(1) Allyl (5S,6S,7S)-5-[(R)-1-(trimethylsilyloxy)ethyl]-4-oxo-9-thia-3-azatricyclo[5.4.0.0³,⁶]undec-1-ene-2-carboxylate (R¹=SiMe₃, R²=CH₂CH=CH₂)

IR (Neat): 2950, 2900, 1780, 1720, 1650, 1630 cm⁻¹
1H-NMR (CDCl₃) δ: 0.13 (9H, s), 1.26 (3H, d, J=6.2 Hz), 2.3–2.9 (5H, m), 3.17 (1H, dd, J=3.4 & 6.8 Hz), 3.1–3.3 (2H, m), 3.82 (1H, dt, J=13 & 3 Hz), 4.14 (1H, dd, J=3.4 & 10.2 Hz), 4.18 (1H, dq, J=6.8 & 6.2 Hz), 4.68 (1H, ddt, J=5.4, 13.6 & 1.4 Hz), 4.80 (1H, ddt, J=5.4, 13.6 & 1.4 Hz), 5.26 (1H, dq, J=10.4 & 1.4 Hz), 5.43 (1H, dq, J=17.2 & 1.4 Hz), 5.96 (1H, ddt, J=10.4, 17.2 & 5.4 Hz)

(2) Allyl (5S,6S,7S)-5-[(R)-1-hydroxyethyl]-4-oxo-9-thia-3-azatricyclo[5.4.0.0³,⁶]undec-1-ene-2-carboxylate (R¹=H, R²=CH₂CH=CH₂) m.p.: 85°–95° C.

IR (KBr): 3430, 2970, 2910, 1770, 1710, 1635 cm⁻¹
1H-NMR (CDCl₃) δ: 1.34 (3H, d, J=6.2 Hz), 1.72 (1H, d, J=5.6 Hz), 2.3–3.0 (5H, m), 3.20 (1H, dd, J=2.8 & 6.6 Hz), 3.1–3.3 (1H, m), 3.74 (1H, dd, J=2.8 & 7.4 Hz), 3.86 (1H, dt, J=15 & 2.6 Hz), 4.24 (1H, ddq, J=5.6, 6.6 & 6.2 Hz), 4.43 (1H, ddt, J=5.4, 13.2 & 1.4 Hz), 4.82 (1H, ddt, J=5.4, 13.2 & 1.4 Hz), 5.28 (1H, dq, J=10.4 & 1.4 Hz), 5.43 (2H, dq, J=17.2 & 1.4 Hz), 5.97 (1H, ddt, J=10.4, 17.2 & 5.4 Hz)

(3) Title compound (R¹=H, R²=Na)
IR (KBr): 3400, 2960, 2910, 1750, 1630, 1590 cm⁻¹
1H-NMR (D₂O) δ: 1.28 (3H, d, J=6.4 Hz), 2.3–2.8 (5H, m), 3.1–3.3 (1H, m), 3.42 (1H, dd, J=3.2 & 5.9 Hz), 3.5–3.6 (1H, m), 4.22 (1H, dd, J=3.2 & 9.8 Hz), 4.24 (1H, dq, J=5.9 & 6.4 Hz) Analysis:

|  | C | H | N |
|---|---|---|---|
| Calcd. for C₁₂H₁₄NNaO₄S.1.4 H₂O: | 45.54 | 5.35 | 4.43 |
| Found: | 45.72 | 5.23 | 4.29 |

EXAMPLE 17

Sodium (5S,6S,7R)-5-[(R)-1-hydroxyethyl]-4-oxo-9-thia-3-azatricyclo[5.4.0.0³,⁶]undec-1-ene-2-carboxylate

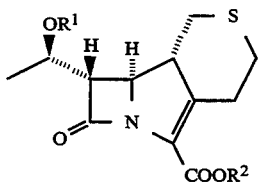

The following compounds were produced in generally the same manner as in Example 8.

(1) Allyl (5S,6S,7R)-5-[(R)-1-(trimethylsilyloxy)ethyl]-4-oxo-9-thia-3-azatricyclo[5.4.0.0³,⁶]undec-1-ene-2-carboxylate (R¹=SiMe₃, R²=CH₂CH=CH₂)

IR (Neat): 2950, 2900, 1780, 1720, 1650, 1625 cm⁻¹
1H-NMR (CDCl₃) δ: 0.13 (9H, s), 1.27 (3H, d, J=6.2 Hz), 2.2–3.0 (5H, m), 3.15 (1H, dd, J=2.8 & 7.0 Hz), 3.2–3.3 (1H, m), 3.63 (1H, dd, J=2.8 & 7.6 Hz), 3.8–3.9 (1H, m), 4.16 (1H, dq, J=7.0 & 6.2 Hz), 4.69 (1H, ddt, J=5.4, 13.4 & 1.4 Hz), 4.80 (1H, ddt, J=5.4, 13.4 & 1.4 Hz), 5.26 (1H, dq, J=10.4 & 1.4 Hz), 5.43 (1H, dq, J=17.2 & 1.4 Hz), 5.97 (1H, ddt, J=10.4, 17.2 & 5.4 Hz)

(2) Allyl (5S,6S,7R)-5-[(R)-1-hydroxyethyl]-4-oxo-9-thia-3-azatricyclo[5.4.0.0³,⁶]undec-1-ene-2-carboxylate (R¹=H, R²CH₂CH=CH₂) m.p.: 150°–153° C.

IR(KBr): 3420, 2960, 2930, 1780, 1710, 1625 cm⁻¹
1H-NMR (CDCl₃) δ: 1.34 (3H, d, J=6.4 Hz), 1.75 (1H, d, J=5.6 Hz), 2.4–2.9 (5H, m), 3.1–3.3 (1H, m), 3.22 (1H, dd, J=3.2 & 6.4 Hz), 3.83 (1H, dt, J=12.6 & 3.3 Hz), 4.24 (1H, dd, J=3.2 & 10.1 Hz), 4.25 (1H, d, quintet, J=5.6 & 6.4 Hz), 4.69 (1H, ddt, J=5.4, 13.4 & 1.4 Hz), 4.82 (1H, ddt, J=5.4, 13.4 & 1.4 Hz), 5.28 (1H, dq, J=10.4 & 1.4 Hz), 5.43 (1H, dq, J=17.2 & 1.4 Hz), 5.98 (1H, ddt, J=10.4, 17.2 & 5.4 Hz) Analysis:

|  | C | H | N |
|---|---|---|---|
| Calcd. for C₁₅H₁₉NO₄S.0.5 H₂O: | 56.59 | 6.33 | 4.40 |
| Found: | 56.79 | 6.26 | 4.42 |

(3) Title compound (R¹=H, R²=Na)
IR (KBr): 3400, 2960, 2910, 1735, 1620, 1590 cm⁻¹
1H-NMR (D₂O) δ: 1.28 (3H, d, J=6.4 Hz), 2.2–3.1 (5H, m), 3.2–3.4 (1H, m), 3.44 (1H, dd, J=2.8 & 5.7 Hz), 3.5–3.6 (1H, m), 3.74 (1H, dd, J=2.8 & 7.3 Hz), 4.23 (1H, dq, J=5.7 & 6.4 Hz) Analysis:

|  | C | H | N |
|---|---|---|---|
| Calcd. for C₁₂H₁₄NNaO₄S.1.4 H₂O: | 45.54 | 5.34 | 4.42 |
| Found: | 65.68 | 5.30 | 4.28 |

EXAMPLE 18

Sodium (9S,10R,11S)-11-[(R)-1-hydroxyethyl]-12-oxo-5-thia-13-azatetracyclo[7.5.0.0²,⁶.0¹⁰,¹³]tetradeca-2(6),3,14(1)-triene-14-carboxylate

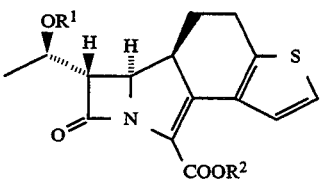

The following compounds were produced in generally the same manner as in Example 8.

(1) Allyl (9S,10R,11S)-11-[(R)-1-(trimethylsilyloxy)ethyl]-12-oxo-5-thia-13-azatetracyclo[7.5.0.0²,⁶.0¹⁰,¹³]-tetradeca-2(6),3,14(1)-triene-14-carboxylate
R¹=SiMe₃, R₂=CH₂CH=CH₂) m.p.: 103°–104° C.

IR (KBr): 2955, 1777, 1718, 1647, 1610 cm⁻¹ 1H-NMR (CDCl₃) δ: 0.15 (9H, s), 1.27 (3H, d, J=6.2 Hz), 1.86–2.22 (2H, m), 2.95–3.32 (3H, m), 3.32 (1H, dd, J=6.2 Hz, 4.0 Hz), 4.23 (1H, dq, J=6.2 Hz, 6.2 Hz), 4.28 (1H, dd, J=11.2 Hz, 4.0 Hz), 4.74 (1H, ddt, J=13.4 Hz, 5.4 Hz, 1.4 Hz), 4.82 (1H, ddt, J=13.4 Hz, 5.4 Hz, 1.4 Hz), 5.27 (1H, ddd, J=10.6 Hz, 2.6 Hz, 1.4 Hz), 5.46 (1H, ddd, J=17.2 Hz, 2.6 Hz, 1.4 Hz), 6.00 (1H, ddt, J=17.2 Hz, 10.6 Hz, 5.4 Hz), 7.11 (1H, d, J=5.4 Hz), 7.78 (1H, d, J=5.4 Hz)

(2) Allyl (9S,10R,11S)-11-[(R)-1-hydroxyethyl]-12-oxo-5-thia-13-azatetracyclo[7.5.0.0$^{2,6}$.0$^{10,13}$]tetradeca-2(6),3,14(1)-triene-14-carboxylate (R$^1$=H, R$^2$=CH$_2$CH=CH$_2$)

IR (Neat): 3450, 2940, 1780, 1713, 1650, 1600 cm$^{-1}$ 1H-NMR (CDCl$_3$) δ: 1.36 (3H, d, J=6.2 Hz), 1.75 (1H, d, J=4.6 Hz), 1.87–2.26 (2H, m), 3.06–3.20 (2H, m), 3.16–3.35 (1H, m), 3.35 (1H, dd, J=6.4 Hz, 3.8 Hz), 4.20–4.35 (1H, m), 4.36 (1H, dd, J=11.2 Hz, 3.8 Hz), 4.74 (1H, ddt, J=13.4 Hz, 5.8 Hz, 1.4 Hz), 4.85 (1H, ddt, J=13.4 Hz, 5.8 Hz, 1.4 Hz), 5.28 (1H, ddd, J=10.4 Hz, 2.8 Hz, 1.4 Hz), 5.45 (1H, ddd, J=17.2 Hz, 2.8 Hz, 1.4 Hz), 6.00 (1H, ddt, J=17.2 Hz, 10.4 Hz, 5.8 Hz), 7.12 (1H, d, J=5.4 Hz), 7.78 (1H, d, J=5.4 Hz)

(3) Title compound (R$^1$=H, R$^2$=Na)

IR (KBr): 3400, 2975, 1760, 1650, 1590 cm$^{-1}$ 1H-NMR (D$_2$O) δ: 1.30 (3H, d, J=6.4 Hz), 1.80–2.06 (1H, m), 2.10–2.20 (1H, m), 2.85–3.12 (2H, m), 3.30 (1H, ddd, J=13.6 Hz, 10.6 Hz, 3.2 Hz), 3.56 (1H, dd, J=6.4 Hz, 4.0 Hz), 4.28 (1H, dq, J=6.4 Hz, 6.4 Hz), 4.38 (1H, dd, J=10.6 Hz, 4.0 Hz), 7.22 (1H, d, J=5.4 Hz), 7.37 (1H, d, J=5.4 Hz) Analysis:

|  | C | H | N |
|---|---|---|---|
| Calcd. for C$_{15}$H$_{14}$NNaO$_4$S.1.5 H$_2$O: | 50.84 | 4.84 | 3.95 |
| Found: | 50.77 | 4.53 | 3.66 |

EXAMPLE 19

Sodium (9R,10R,11S)-11-[(R)-1-hydroxyethyl]-12-oxo-5-thia-13-azatetracyclo[7.5.0.0$^{2,6}$.0$^{10,13}$]tetradeca-2(6),3,14(1)-triene-14-carboxylate

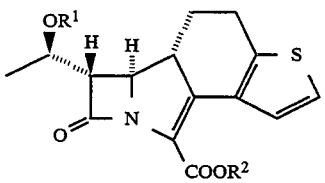

The following compounds were produced in generally the same manner as in Example 8.

(1) Allyl (9R,10R,11S)-11-[(R)-1-(trimethylsilyloxy)ethyl]-oxy-5-thia-13-azatetracyclo[7.5.0.0$^{2,6}$.0$^{10,13}$]-tetradeca-2(6),3,14(1)-triene-14-carboxylate (R$^1$=SiMe$_3$, R$^2$=CH$_2$CH=CH$_2$)

IR (Neat): 3080, 2960, 1765, 1705, 1640, 1570, 1500 cm$^{-1}$ 1H-NMR (CDCl$_3$) δ: 0.16 (9H, s), 1.32 (3H, d, J=6.2 Hz), 1.75–2.06 (1H, m), 2.05–2.40 (1H, m), 2.97 (1H, ddd, J=17.2 Hz, 5.2 Hz), 3.06–3.20 (1H, m), 3.15 (1H, dd, J=7.6 Hz, 2.4 Hz), 3.29 (1H, ddd, J=12.6 Hz, 9.4 Hz, 4.2 Hz), 3.72 (1H, dd, J=9.2 Hz, 2.2 Hz), 4.20 (1H, dq, J=7.6 Hz, 6.2 Hz), 4.73 (1H, ddt, J=13.6 Hz, 5.4 Hz, 1.4 Hz), 4.83 (1H, ddt, J=13.6 Hz, 5.4 Hz, 1.4 Hz), 5.27 (1H, ddd, J=10.6 Hz, 3.0 Hz, 1.4 Hz), 5.47 (1H, ddd, J=17.2 Hz, 3.0 Hz, 1.4 Hz), 6.00 (1H, ddt, J=17.2 Hz, 10.6 Hz, 5.4 Hz), 7.11 (1H, d, J=5.4 Hz), 8.16 (1H, d, J=5.4 Hz)

(2) Allyl (9R,10R,11S)-11-[(R)-1-hydroxyethyl]-12-oxo-5-thia-13-azatetracyclo [7.5.0.0$^{2,6}$.0$^{10,13}$]tetradeca-2(6),3,14(1)-triene-14-carboxylate (R$^1$=H, R$^2$=CH$_2$CH=CH$_2$)

IR (KBr): 3410, 3100, 2925, 1760, 1710, 1650, 1575 cm$^{-1}$ 1H-NMR (CDCl$_3$) δ: 1.39 (3H, d, J=6.2 Hz), 1.75 (1H, d, J=4.6 Hz), 1.97 (1H, dddd, J=13.0 Hz, 12.4 Hz, 11.8 Hz, 5.4 Hz), 2.36 (1H, dddd, J=12.4 Hz, 5.4 Hz, 4.2 Hz, 2.2 Hz), 2.98 (1H, ddd, J=17.6 Hz, 11.8 Hz, 5.4 Hz), 3.14 (1H, ddd, J=17.6 Hz, 5.4 Hz, 2.2 Hz), 3.19 (1H, dd, J=6.8 Hz, 2.4 Hz), 3.31 (1H, ddd, J=13.0 Hz, 9.0 Hz, 4.2 Hz), 3.84 (1H, dd, J=9.0 Hz, 2.4 Hz), 4.20–4.36 (1H, m), 4.75 (1H, ddt, J=13.4 Hz, 5.6 Hz, 1.4 Hz), 4.86 (1H, ddt, J=13.4 Hz, 5.6 Hz, 1.4 Hz), 5.27 (1H, ddd, J=10.6 Hz, 2.8 Hz, 1.4 Hz), 5.48 (1H, ddd, J=17.2 Hz, 2.8 Hz, 1.4 Hz), 6.00 (1H, ddt, J=17.2 Hz, 10.6 Hz, 5.6 Hz), 7.12 (1H, d, J=5.4 Hz), 8.17 (1H, d, J=5.4 Hz)

(3) Title compound (R$^1$=H, R$^2$=Na)

IR (KBr): 3400, 2925, 1745, 1600 cm−1 1H-NMR (D$_2$O) δ: 1.33 (3H, d, J=6.2 Hz), 1.65–1.94 (1H, m), 2.28–2.44 (1H, m), 2.92 (1H, ddd, J=16.8 Hz, 12.0 Hz, 4.8 Hz), 3.08 (1H, ddd, J=16.8 Hz, 5.0 Hz, 2.0 Hz), 3.40 (1H, ddd, J=13.2 Hz, 9.2 Hz, 4.6 Hz), 3.43 (1H, dd, J=6.2 Hz, 2.0 Hz), 3.85 (1H, dd, J=9.2 Hz, 4.6 Hz), 4.26 (1H, dq, J=6.2 Hz, 6.2 Hz), 7.25 (1H, d, J=5.4 Hz), 7.81 (1H, d, J=5.4 Hz) Analysis:

|  | C | H | N |
|---|---|---|---|
| Calcd. for C$_{15}$H$_{14}$NNaO$_4$OS.2.0 H$_2$O: | 49.58 | 4.99 | 3.85 |
| Found: | 49.78 | 4.76 | 3.71 |

EXAMPLE 20

Sodium (5S,6S,7S)-5-[(R)-1-hydroxyethyl]-4-oxo-8-oxa-3-azatricyclo[5.4.0.0$^{3,6}$]undec-1-ene-2-carboxylate

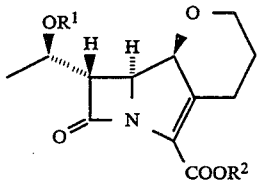

The following compounds were produced in generally the same manner as in Example 8.

(1) Allyl (5S,6S,7S)-5-[(R)-1-(trimethylsilyloxy)ethyl]-4oxo-8-oxa-3-azatricyclo[5.4.0.0$^{3,6}$]undec-1-ene-2-carboxylate (R$^1$=SiMe$_3$, R$^2$=CH$_2$CH=CH$_2$)

IR (Neat): 2960, 2850, 1790, 1710, 1650 cm$^{-1}$ 1H-NMR (CDCl$_3$) δ: 0.13 (9H, s), 1.22 (3H, d, J=6.2 Hz), 1.7–1.9 (2H, m), 2.3–2.5 (1H, m), 3.4–3.5 (1H, m), 3.59 (1H, dd, J=3.6 & 5.4 Hz), 3.6–3.7 (1H, m), 4.0–4.1 (1H, m), 4.13 (1H, dd, J=3.6 & 8.6 Hz), 4.26 (1H, dq, J=5.4 & 6.2 Hz), 4.37 (1H, d, J=8.6 Hz), 4.70 (1H, ddt, J=5.4, 13.4 & 1.4 Hz), 4.81 (1H, ddt, J=5.4, 13.4 & 1.4 Hz), 5.26 (1H, dq, J=10.4 & 1.4 Hz), 5.43 (1H, dq, J=17.2 & 1.4 Hz), 5.97 (1H, ddt, J=10.4, 17.2 & 5.4 Hz)

(2) Allyl (5S,6S,7S)-5-[(R)-1-hydroxyethyl]-4-oxo-8-oxa-3-azatricyclo[5.4.0.0$^{3,6}$]undec-1-ene-2-carboxylate (R$^1$=H, R$^2$CH$_2$CH=CH$_2$)

IR (KBr): 3500, 2960, 2940, 2920, 1770, 1705, 1640 cm$^{-1}$ 1H-NMR (CDCl$_3$) δ: 1.32 (3H, d, J=6.2 Hz), 1.4–1.9 (3H, m), 2.3–2.5 (1H, m), 3.4–3.5 (1H, m), 3.6–3.8 (1H, m), 3.65 (1H, dd, J=3.6 & 6.2 Hz), 4.0–4.1 (1H, m), 4.18 (1H, dd, J=3.6 & 8.4 Hz), 4.2–4.3 (1H, m), 4.42 (1H, d, J=8.4 Hz), 4.71 (1H, ddt, J=5.4, 13.4 & 1.4 Hz), 4.83 (1H, ddt, J=5.4, 13.4 & 1.44 Hz), 5.28 (1H, dq, J=10.4 & 1.4 Hz), 5.43 (1H, dq, J=17.2 & 1.4 Hz), 5.98 (1H, ddt, J=10.4, 17.2 & 5.4 Hz) Analysis:

|  | C | H | N |
|---|---|---|---|
| Calcd. for C$_{15}$H$_{19}$NO$_5$: | 61.42 | 6.53 | 4.78 |

|        | C     | H    | N    |
|--------|-------|------|------|
| Found: | 61.22 | 6.62 | 4.50 |

(3) Title compound ($R^1$=H, $R^2$=Na)

IR (KBr): 3420, 2960, 2920, 2850, 1770, 1590, 1400 $cm^{-1}$ $^1$H-NMR ($D_2$) δ: 1.27 (3H, d, J=6.6 Hz), 1.6–1.9 (2H, m), 2.42 (1H, dd, J=5.4 & 12.6 Hz), 3.2–3.3 (1H, m), 3.53 (1H, dd, J=3.5 & 5.2 Hz), 3.79 (1H, dt, J=3.0 & 11.7 Hz), 4.0–4.1 (1H, m), 4.18 (1H, dd, J=3.5 & 8.4 Hz), 4.29 (1H, dq, J=5.2 & 6.6 Hz), 4.60 (1H, d, J=8.4 Hz) Analysis:

|                                       | C     | H    | N    |
|---------------------------------------|-------|------|------|
| Calcd. for $C_{12}H_{14}NNaO_5$·0.9 $H_2O$: | 49.45 | 5.46 | 4.81 |
| Found:                                | 49.66 | 5.21 | 4.59 |

EXAMPLE 21

Sodium (5S,6S,7R)-5-[(R)-1-hydroxyethyl]-4-oxo-8-oxa-3-azatricyclo[5.4.0.0$^{3,6}$]undec-1-ene-2-carboxylate

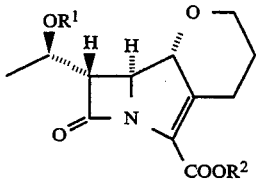

The following compounds were produced in generally the same manner as in Example 8.

(1) Allyl (5S,6S,7R)-5-[(R)-1-(trimethylsilyloxy)ethyl]-4-oxo-8-oxa-3-azatricyclo[5.4.0.0$^{3,6}$]undec-1-ene-2-carboxylate ($R^1$=SiMe$_3$, $R^2$=CH$_2$CH=CH$_2$)

IR (Neat): 2950, 2850, 1780, 1720, 1600 $cm^{-1}$ $^1$H-NMR (CDCl$_3$) δ: 0.14 (9H, s), 1.28 (3H, d, J=6.2 Hz), 1.7–1.9 (2H, m), 2.2–2.4 (1H, m), 3.15 (1H, dd, J=3.1 & 6.6 Hz), 3.3–3.6 (2H, m), 3.90 (1H, dd, J=3.1 & 5.8 Hz), 4.0–4.1 (1H, m), 4.20 (1H, dq, J=6.6 Hz & 6.2 Hz), 4.64 (1H, d, J=5.8 Hz), 4.70 (1H, dd, J=5.4, 13.6 & 1.4 Hz), 4.80 (1H, ddt, J=5.4, 13.6 & 1.4 Hz), 5.26 (1H, dq, J=10.4 & 1.4 Hz), 5.43 (1H, dq, J=17.2 & 1.4 Hz), 5.97 (1H, ddt, J=10.4, 17.2 & 5.4 Hz)

(2) Allyl (5S,6S,7R)-5-[(R)-1-hydroxyethyl]-4-oxo-8-oxa-3-azatricyclo[5.4.0.0$^{3,6}$]undec-1-ene-2-carboxylate ($R^1$=H, $R^2$=CH$_2$CH=CH$_2$)

IR(KBr): 3430, 2960, 2940, 2930, 2850, 1780, 1720, 1635 $cm^{-1}$ $^1$H-NMR (CDCl$_3$) δ: 1.36 (3H, d, J=6.4 Hz), 1.6–1.9 (3H, m), 2.2–2.4 (1H, m), 3.23 (1H, dd, J=3.2 & 6.4 Hz), 3.4–3.5 (1H, m), 3.5–3.7 (1H, m), 3.95 (1H, dd, J=3.2 & 5.8 Hz), 4.0–4.1 (1H, m), 4.22 (1H, quintet, J=6.4 Hz), 4.68 (1H, d, J=5.8 Hz), 4.70 (1H, ddt, J=5.6, 13.4 & 1.4 Hz), 4.82 (1H, ddt, J=5.6, 13.4 & 1.4 Hz), 5.28 (1H, dq, J=10.6 & 1.4 Hz), 5.43 (1H, dq, J=17.2 & 1.4 Hz), 5.98 (1H, ddt, J=10.6, 17.2 & 5.6 Hz) Analysis:

|                          | C     | H    | N    |
|--------------------------|-------|------|------|
| Calcd. for $C_{15}H_{19}NO_5$: | 61.42 | 6.53 | 4.78 |
| Found:                   | 61.45 | 6.38 | 4.54 |

(3) Title compound ($R^1$=H, $R^2$=Na)

IR(KBr): 3400, 2970, 2930, 2850, 1740, 1590, 1400 $cm^{-1}$ $^1$H-NMR ($D_2O$) δ: 1.29 (3H, d, J=6.2 Hz), 1.6–1.9 (2H, m), 2.2–2.4 (1H, m), 3.0–3.2 (1H, m), 3.51 (1H, dd, J=3.2 & 5.4 Hz), 3.71 (1H, dt, J=2.4 & 12.0 Hz), 3.91 (1H, dd, J=3.2 & 5.2 Hz), 4.0–4.1 (1H, m), 4.27 (1H, dq, J=5.4 Hz & 6.2 Hz), 4.95 (1H, d, J=5.4 Hz) Analysis:

|                                       | C     | H    | N    |
|---------------------------------------|-------|------|------|
| Calcd. for $C_{12}H_{14}NNaO_5$·1 $H_2O$: | 49.15 | 5.50 | 4.78 |
| Found:                                | 49.16 | 5.33 | 4.69 |

EXAMPLE 22

Sodium (5S,6S,7S)-5-[(R)-1-hydroxyethyl]-4-oxo-8-thia-3-azatricyclo[5.4.0.0$^{3,6}$]undec-1-ene-2-carboxylate

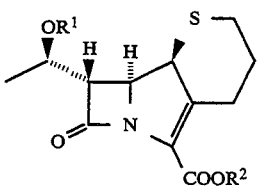

The following compounds were produced in generally the same manner as in Example 8.

(1) Allyl (5S,6S,7S)-5-[(R)-1-(trimethylsilyloxy)ethyl]-4-oxo-8-thia-3-azatricyclo[5.4.0.0$^{3,6}$]undec-1-ene-2-carboxylate ($R^1$=SiMe$_3$, $R^2$=CH$_2$CH=CH$_2$)

IR(KBr): 2950, 1780, 1715, 1630, 1570 $cm^{-1}$ (2) Allyl (5S,6S,7S)-5-[(R)-1-hydroxyethyl]-4-oxo-8-thia-3-azatricyclo[5.4.0.0$^{3,6}$]undec-1-ene-2-carboxylate ($R^1$=H, $R^2$=CH$_2$CH=CH$_2$)

IR(Neat): 3480, 2940, 1770, 1710, 1630 $cm^{-1}$ $^1$H-NMR (CDCl$_3$) δ: 1.32 (3H, d, J=6.2 Hz), 1.73 (1H, d, J=5.0 Hz), 1.7–2.3 (3H, m), 2.7–3.0 (2H, m), 3.40 (1H, dd, J=3 & 6 Hz), 3.6–3.7 (1H, m), 4.05 (1H, d, J=9.2 Hz), 4.24 (1H, ddq, J=5.0, 6.0 & 6.2 Hz), 4.33 (1H, dd, J=3.0 & 9.2 Hz), 4.69 (1H, ddt, J=5.6, 13.4 & 1.6 Hz), 4.83 (1H, ddt, J=5.6, 13.4 & 1.6 Hz), 5.27 (1H, dq, J=10.4 & 1.6 Hz), 5.44 (1H, dq, J=17.2 & 1.6 Hz), 5.98 (1H, ddt, J=10.4, 17.2 & 5.6 Hz)

(3) Title compound ($R^1$=H, $R^2$=Na)

IR (KBr): 3430, 2920, 1760, 1630, 1580 $cm^{-1}$ $^1$H-NMR ($D_2O$) δ: 1.28 (3H, d, J=6.4 Hz), 1.4–2.3 (3H, m), 2.8–3.1 (2H, m), 3.3–3.4 (1H, m), 3.40 (1H, dd, J=2.8 & 5.8 Hz), 4.19 (1H, d, J=9.2 Hz), 4.23 (1H, dq, J=5.8 & 6.4 Hz), 4.32 (1H, dd, J=2.8 & 9.2 Hz)

EXAMPLE 23

Sodium (5S,6S,7R)-5-[(R)-1-hydroxyethyl]-4-oxo-8-thia-3-azatricyclo[5.4.0.0$^{3,6}$]undec-1-ene-2-carboxylate

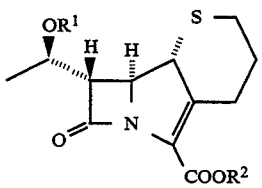

The following compounds were produced in generally the same manner as in Example 8.

(1) Allyl (5S,6S,7R)-5-[(R)-1-(trimethylsilyloxy)ethyl]-4-oxo-8-thia-3-azatricyclo[5.4.0.0$^{3,6}$]undec-1-ene-2-carboxylate ($R^1$=SiMe$_3$, $R^2$=CH$_2$CH=CH$_2$)

IR (KBr): 2690, 1790, 1710 cm$^{-1}$ $^1$H-NMR (CDCl$_3$) δ: 0.14 (9H, s), 1.26 (3H, d, J=6.2 Hz), 1.8–2.3 (3H, m), 2.6–2.9 (2H, m), 3.25 (1H, dd, J=3.1 & 6.6 Hz), 3.6–3.7 (1H, m), 3.74 (1H, dd, J=3.1 & 7.0 Hz), 4.15 (1H, d, J=7.0 Hz), 4.16 (1n, dq, J=6.6 6.2 Hz), 4.70 (1H, ddt, J=5.4, 13.5 & 1.4 Hz), 4.81 (1H, ddt, J=5.4, 13.5 & 1.4 Hz), 5.26 (1H, dq, J=10.4 & 1.4 Hz ), 5.44 (1H, dq, J=17.2 & 1.4 Hz), 5.97 (1H, ddt, J=10.4, 17.2 & 5.4 )

(2) Allyl (5S, 6S, 7R )-5-[(R)-1-hydroxyethyl]-4-oxo-8-thia-3-azatricyclo[5.4.0.0$^{3,6}$]undec-1-ene-2-carboxylate (R=H, R$^2$=CH$_2$CH=CH$_2$) m.p.: 107°–117° C.

IR (KBr): 3440, 2940, 1780, 1720, 1620 cm$^{-1}$ $^1$H-NMR (CDCl$_3$) δ: 1.33 (3H, d, J=6.4 Hz), 1.78 (1H, d, J=4.8 Hz), 1.8–2.3 (3H, m), 2.6–3.0 (2H, m), 3.32 (1H, dd, J=3.1 & 6.1 Hz), 3.6–3.7 (1H, m), 3.83 (1H, dd, J=3.1 & 6.5 Hz), 4.17 (1H, d, J=6.5 Hz), 4.24 (1H, ddq, J=4.8 Hz, 6.1 & 6.4 Hz), 4.70 (1H, ddt, J=5.4, 13.4 & 1.6 Hz), 4.82 (1H, ddt, J=5.6, 13.4 & 1.6 Hz), 5.27 (1H, dq, J=10.6 & 1.6 Hz), 5.43 (1H, dq, J=17.2 & 1.6 Hz), 5.98 (1H, ddt, J=10.4, 17.2 & 5.4 Hz) Analysis:

|  | C | H | N |
|---|---|---|---|
| Calcd. for C$_{15}$H$_{19}$NO$_4$S.0.2 H$_2$O: | 57.56 | 6.25 | 4.48 |
| Found: | 56.67 | 6.10 | 4.44 |

(3) Title compound (R$^1$=H, R$^2$=Na)

IR (KBr): 3400, 2930, 1755, 1620, 1590 cm$^{-1}$ $^1$H-NMR (D$_2$O) δ: 1.28 (3H, d, J=6.4 Hz), 1.6–2.3 (3H, m), 2.6–2.8 (2H, m), 2.93 (1H, dt, J=2.0 & 13.1 Hz), 3.3–3.4 (1H, m), 3.58 (1H, dd, J=3.0 & 5.7 Hz), 3.80 (1H, dd, J=3.0 & 6.2 Hz), 4.23 (1H, dq, J=5.7 & 6.4 Hz), 4.40 (1H, d, J=6.2 Hz)

EXAMPLE 24

(5S,6R,7R)-9-Allyl-5-[(R)-1-hydroxyethyl]-4-oxo-3,9-diazatricyclo[5.4.0.0$^{3,6}$]undec-1-ene-2-carboxylic acid

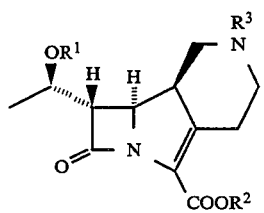

The following compounds were produced in generally the same manner as in Example 8.

(1) Allyl (5S,6R,7R)-9-allyloxycarbonyl-5-[(R)-1-(trimethylsilyloxy)ether]-4-oxo-3,9-diazatriccyclo-[5.4.0.0$^{3,6}$]undec-1-ene-2-carboxylate (R$^1$=SiMe$_3$, R$^2$=CH$_2$CH=CH$_2$, R$^3$=COOCH$_2$CH=CH$_2$)

IR (neat): 2950, 1785, 1710 cm$^{-1}$ (2) Allyl (5S,6R,7R)-8-allyloxycarbonyl-5-[(R)-1-hydroxyethyl]-4-oxo-3,9-diazatricyclo[5.4.0.0$^{3,6}$]undec-1-ene-2-carboxylate (R$^1$=H, R$^2$=CH$_2$CH=CH$_2$, R$^3$=COOCH$_2$CH=CH$_2$)

IR (KBr): 3450, 2930, 1780, 1705, 1650 cm$^{-1}$ (3) Title compound (R$^1$=R$^2$=H, R$^3$=CH$_2$CH=CH$_2$)

IR (KBr): 3430, 2980, 2930, 1760, 1650, 1590 cm$^{-1}$ $^1$H-NMR (D$_2$O) δ: 1.26 (3H, d, J=6.2 Hz), 2.5–2.9 (3H, m), 3.2–3.8 (6H, m), 3.41 (1H, dd, J=3.4 & 5.4 Hz), 4.24 (1H, dq, J=5.4 & 6.2 Hz), 4.29 (1H, dd, J=3.4 & 10.6 Hz), 5.51 (1H, dd, J=1.2 & 17.4 Hz), 5.51 (1H, dd, J=1.2 & 9.8 Hz), 5.94 (1H, ddt, J=9.8, 17.4 & 6.8 Hz)

EXAMPLE 25

(5S,6R,7S)-9-Allyl-5-[(R)-1-hydroxyethyl]-4-oxo-3,9diazatricyclo[5.4.0.0$^{3,6}$]undec-1-ene-2-carboxylic acid

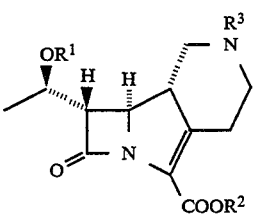

The following compounds were produced in generally the same manner as Example 8.

(1) Allyl (5S,6R,7S)-9-allyloxycarbonyl-5-[(R)-1-(trimethylsilyloxy)ethyl]-4-oxo-3,9-diazatricyclo[5.4.0.0$^{3,6}$]undec-1-ene-2-carboxylate (R$^1$=SiMe$_3$, R$^2$=CH$_2$CH=CH$_2$, R$^3$=COOCH$_2$CH=CH$_2$)

IR (Neat): 2960, 1785, 1710 cm$^{-1}$ (2) Allyl (5S,6R,7S)-9-allyloxycarbonyl-5-[(R)-1-hydroxyethyl]-4-oxo-3,9-diazatricyclo[5.4.0.0$^{3,6}$]undec-1-ene-2-carboxylate (R$^1$=H, R$^2$=CH$_2$CH=CH$_2$, R$^3$COOCH$_2$CH=CH$_2$)

IR (KBr): 3430, 2940, 2880, 1785, 1710, 1640 cm$^{-1}$ (3) Title compound (R$^1$=R$^2$=H, R$^3$=CH$_2$CH=CH$_2$)

IR (KBr): 3430, 2970, 2930, 1760, 1600 cm$^{-1}$ $^1$H-NMR (D$_2$O) δ: 1.28 (3H, d, J=6.4 Hz), 2.4–2.6 (1H, m) , 2.7–3.0 (2H, m), 3.3–3.8 (6H, m), 3.50 (1H, dd, J=2.8 & 5.8 Hz), 3.86 (1H, dd, J=2.8 & 7.4 Hz), 4.24 (1H, dq, J=5.8 & 6.4 Hz), 5.55 (1H, d, J=17.4 Hz), 5.56 (1H, d, J=9.6 Hz), 5.95 (1H, ddt, J=9.6, 17.4 & 7.2 Hz)

EXAMPLE 26

(10S,11R,12S)-5-(2-Aminoethoxy)-12-[(R)-1-hydroxyethyl]-13-oxo-14-azatetracyclo-[8.5.0.0$^{2,7}$.0$^{11,14}$]pentadeca-2,4,6,15(1)tetraene15-carboxylic acid

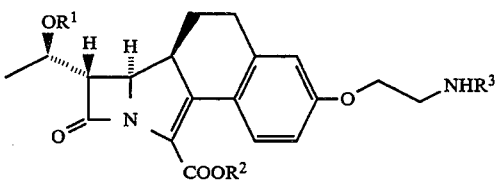

The following compounds were produced in generally the same manner as Examples in 8(1) and 8(2).

(1) Allyl (10S,11R,12S)-5-[2-[(allyloxycarbonyl)amino]-ethoxy]-12-[(R)-1-(trimethylsilyloxy)ethyl]-13-oxo-14-azateracyclo[8.5.0.0$^{2,7}$.0$^{11,14}$]pentadeca-2,4,6,15(1)-tetraene-15-carboxylate (R$^1$=SiMe$_3$, R$^2$=CH$_2$CH=CH$_2$, R$^3$=COOCH$_2$CH=CH$_2$)

IR(Neat): 3350, 3080, 2950, 1780, 1720, 1650, 1605 cm$^{-1}$ $^1$H-NMR (CDCl$_3$) δ: 0.15 (9H, s), 1.28 (3H, d, J=6.2 Hz), 1.73–2.20 (2H, m), 2.97–3.25 (3H, m), 3.26 (1H, dd, J=6.8 Hz, 3.2 Hz), 3.58 (1H, t, J=5.2 Hz), 3.60 (1H, t, J=5.2 Hz), 4.04 (2H, t, J=5.2 Hz), 4.16–4.31 (2H, m), 4.59 (2H, d, J=5.2 Hz), 4.65–4.90 (2H, m), 5.08–5.50 (5H, m), 5.80–6.10 (2H, m), 6.64 (1H, d, J=2.2 Hz), 6.71 (1H, dd, J=8.8 Hz, 2.2 Hz), 7.83 (1H, d, J=8.8 Hz)

(2) Allyl (10S,11R,12S)-5-[2-[(allyloxycarbonyl)amino]ethoxy]-12-[(R)-1-hydroxyethyl]-13-oxo-14- azatetracyclo[8.5.0.0$^{2,7}$.0$^{11,14}$]pentadeca-2,4,6,15(1)-tetraene-15-carboxylate (R$^1$=H, R$^2$=CH$_2$CH=CH$_2$, R$^3$=COOCH$_2$CH$_2$CH=CH$_2$)

IR (Neat): 3390, 2940, 1773, 1718, 1650, 1610 cm$^{-1}$
1H-NMR (CDCl$_3$) δ: 1.36 (3H, d, J=6.4 Hz), 1.60–2.20 (3H, m), 2.96–3.10 (2H, m), 3.19 (1H, ddd, J=14.2 Hz, 10.4 Hz, 4.0 Hz), 3.30 (1H, dd, J=6.8 Hz, 3.2 Hz), 3.56 (1H, t, J=5.2 Hz), 3.61 (1H, t, J=5.4 Hz), 4.04 (2H, t, J=5.2 Hz), 4.20–4.37 (1H, m), 4.32 (1H, dd, J=10.4 Hz, 3.2 Hz), 4.58 (2H, d, J=6.0 Hz), 4.65–4.92 (2H, m), 5.10–5.48 (5H, m), 5.82–6.12 (2H, m), 6.64 (1H, d, J=2.2 Hz), 6.72 (1H, dd, J=8.6 Hz, 2.2 Hz), 7.84 (1H, d, J=8.6 Hz)

(3) Title compound (R$^1$=R$^2$=R$^3$=H)

In THF-ethanol (2:1, 6 ml) were dissolved the compound obtained in (2) (443 mg), triphenylphosphine (72 mg), dimedone (257 mg) and tetrakis(triphenylphosphine)palladium (0) (31.8 mg) and the solution was stirred in an argon gas stream at room temperature for 4 hours. The resulting precipitate was recovered by filtration and washed with THF-ethanol to give 316 mg of the title compound as an ocher powder. IR (KBr): 3400, 2970, 2940, 1760, 1640–1570, 1500 cm$^{-1}$ 1H-NMR (Me$_2$SO-d$_6$-D$_2$O) δ: 1.16 (3H, d, J=6.2 Hz), 1.50–2.25 (2H, m), 2.75–3.10 (2H, m), 3.10–3.20 (1H, m), 3.23 (1H, dd, J=6.2 Hz, 3.6 Hz), 3.62 (2H, t, J=6.4 Hz), 3.98 (1H, dq, J=6.2 Hz, 6.2 Hz), 4.00–4.20 (2H, m), 4.16 (1H, dd, J=10.8 Hz, 3.6 Hz), 6.62 (1H, dd, J=8.8 Hz, 2.2 Hz), 6.68 (1H, d, J=2.2 Hz), 7.59 (1H, d, J=8.8 Hz)

EXAMPLE 27

(10S,11R,12S)-5-[2-(1-Iminoethyl)amino]ethoxy]-12-[(R)-1-hydroxyethyl]-13-oxo-14-azatetracyclo[8.5.0.0$^{2,7}$.0$^{11,14}$]pentadeca-2,4,6,15(1)-tetraene-15-carboxylic acid

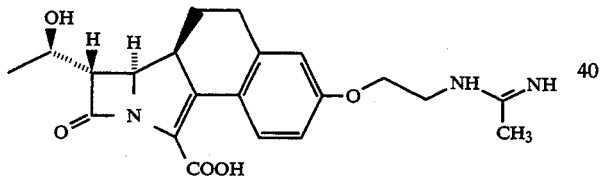

While a suspension of the compound of Example 26 (100 mg) in water (10 ml) was maintained at pH 8.5 by dropwise addition of 2 N-aqueous potassium carbonate solution, benzyl acetamidate hydrochloride (1.554 mg) was added in several portions. The mixture was stirred for a further 20 minutes, at the end of which time it was washed with ethyl acetate-THF (9:1). The aqueous layer was then concentrated under reduced pressure and the residue was purified by Diaion CHP-20 column chromatography (solvent: water→5% ethanol/water→10% ethanol/water) and freeze-dried to give 30 mg of the title compound as powder.

IR (KBr): 3380, 2960, 2925, 1755, 1680, 1600–1580, 1495 cm$^{-1}$ 1H-NMR (D$_2$O) δ: 1.30 (3H, d, J=6.2 Hz), 1.70–1.95 (1H, m), 2.00–2.30 (1H, m), 2.23 (3H, s), 3.01 (2H, brd, J=6.0 Hz), 3.20 (1H, ddd, J=14.0 Hz, 10.6 Hz, 3.0 Hz), 3.55 (1H, dd, J=5.4 Hz, 3.6 Hz), 3.62–3.74 (2H, m), 4.20–4.30 (3H, m), 4.35 (1H, dd, J=10.6 Hz, 3.6 Hz), 6.76–6.86 (2H, m), 7.46 (1H, d, J=8.6 Hz)

EXAMPLE 28

(10S,11R,12S)-5-[2-(Iminomethylamino)ethoxy]-12-[(R)-1-hydroxyethyl]-13-oxo-14-azatetracyclo[8.5.0.0$^{2,7}$.0$^{11,14}$]pentadeca-2,4,6,15(1)-tetraene-15-carboxylic acid

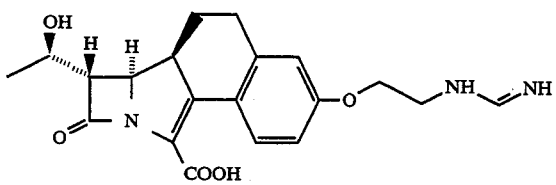

The reaction procedure of Example 27 was repeated except that benzyl formamidate hydrochloride was used in lieu of benzyl acetamidate hydrochloride to give the title compound.

IR (KBr): 3400, 2970, 2930, 1778, 1718, 1610, 1593, 1500 cm$^{-1}$ 1H-NMR (DMSO-d$_6$-D$_2$O) δ: 1.15 (3H, d, J=6.4 Hz), 1.40–1.80 (1H, m), 1.82–2.30 (1H, m), 2.76–3.08 (2H, m), 3.15–3.27 (1H, m), 3.45–3.72 (3H, m), 3.80–4.10 (2H, m), 3.99 (1H, dq, J=6.4 Hz, 6.4 Hz), 4.12 (1H, dd, J=10.8 Hz, 3.2 Hz), 6.50–6.70 (2H, m), 7.73 (1H, d, J=8.2 Hz), 7.95–7.99 (1H, brs)

EXAMPLE 29

Pivaloyloxymethyl (5S,6S,7S)-5-[(R)-1-hydroxyethyl]-4-oxo-11-thia-3-azatricyclo[5.4.0.0$^{3,6}$]undec-1-ene-2-carboxylate

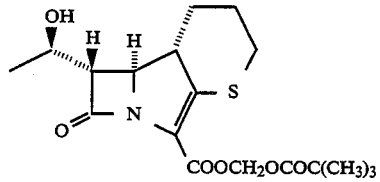

To a solution of the compound of example 7–6) (50 mg) in DMF (1 ml) was added a solution of iodomethyl pivalate (62.3 mg) in DMF (0.5 ml) and the mixture was stirred for 1 hour. To this reaction mixture was added ether and the organic layer was washed successively with water and saturated aqueous sodium chloride solution and dried over anhydrous sodium sulfate. The solvent was then distilled off under reduced pressure and the residue was purified by silica gel column chromatography (solvent:ether) to give 40 mg of the title compound as a colorless amorphous powder.

IR (KBr): 3450, 2975, 2930, 1780, 1785, 1720, 1550 cm$^{-1}$ 1H-NMR (CDCl$_3$) δ: 1.22 (9H, s), 1.34 (3H, d, J=6.2 Hz), 1.42–1.70 (1H, m), 1.70–2.00 (1H, m), 1.97 (1H, brs), 2.12–2.34 (2H, m), 2.48–2.84 (2H, m), 3.11 (1H, ddd, J=11.6 Hz, 9.4 Hz, 1.6 Hz), 3.12 (1H, dd, J=6.4 Hz, 2.2 Hz), 3.77 (1H, dd, J=9.4 Hz, 2.2 Hz), 4.14–4.32 (1H, m), 5.86 (1H, d, J=5.4 Hz), 5.97 (1H, d, J=5.4 Hz)

EXAMPLE 30

(5S,6R,7S)-5-[(R)-1-Hydroxyethyl]-4-oxo-3,9-diazatricyclo[5.4.0.0$^{3,6}$]undec-1-ene-2-carboxylic acid

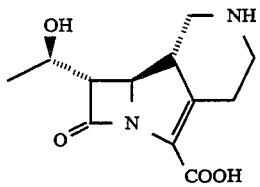

The allyl (5S,6R,7S)-9-allyloxycarbonyl-5-[(R)-1-hydroxyethyl]-4-oxo-3,9-diazatricyclo[5.4.0.0$^{3,6}$]undec-1-ene-2-carboxylate prepared in Example 25-(2) was reacted in the same manner as in Example 26-(3) to give the title compound.

IR (KBr): 3430, 2970, 2930, 1760, 1590 cm$^{-1}$ $^1$H-NMR (D$_2$O) δ: 1.28 (3H, d, J=6.2 Hz), 2.4–2.6 (1H, m), 2.99 (1H, dt, J=3.6 & 13.0 Hz), 3.08 (1H, t, J=13.0 Hz), 3.3 3.6 (4H, m), 3.8–3.9 (2H, m), 4.24 (1H, quintet, J=6.2Hz)

EXAMPLE 31

(5S,6R,7R)-5-[(R)-1-Hydroxyethyl]-4-oxo-3,9-diazatricyclo[5.4.0.0$^{3,6}$]undec-1-ene-2-carboxylic acid

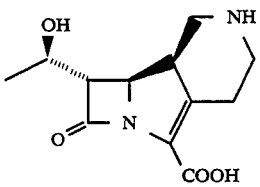

The allyl (5S,6R,7R)-9-allyloxycarbonyl-5-[(R)-1-hydroxyethyl]-4-oxo-3,9-diazatricyclo[5.4.0.0$^{3,6}$]undec-1-ene-2-carboxylate prepared in Example 24-(2) was reacted in the same manner as in Example 26-(3) to give the title compound.

IR (KBr): 3420, 2960, 1765, 1600 cm$^{-1}$ $^1$H-NMR (D$_2$O) δ: 1.26 (3H, d, J=6.2Hz), 2.5–2.7 (1H, m), 2.9–3.2 (2H, m), 3.3–3.8 (4H, m), 3.42 (1H, dd, J=3.5 & 5.6 Hz), 4.24 (1H, dq, J=6.2 & 5.6 Hz), 4.33 (1H, dd, J=3.5 & 10.3 Hz)

EXAMPLE 32

Pivaloyloxymethyl (5S,6R,7S)-9-allyl-5-[(R)-1-hydroxyethyl]-4-oxo-3,9-diazatricyclo[5.4.0.0$^{3,6}$]undec-1-ene-2-carboxylate

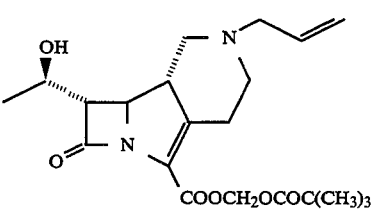

The compound synthesized in Example 25 was reacted in the same manner as in Example 29 to give the title compound.

IR(Neat): 2970, 2930, 2800, 1780, 1755 cm$^{-1}$ $^1$H-NMR (CDCl$_3$) δ: 1.22 (9H, s), 1.33 (3H, d, J=6.2 Hz), 2.3–2.5 (1H, m), 3.0–3.4 (8H, m), 3.17 (1H, dd, J=2.8 & 6.6 Hz), 3.74 (1H, dd, J=2.8 & 7.4 Hz), 4.21 (1H, dq, J=6.2 & 6.6 Hz), 5.2–5.3 (2H, m), 5.7–5.9 (1H, m), 5.83 (1H, d, J=5.4 Hz), 5.94 (1H, d, J=5.4 Hz)

EXAMPLE 33

(5S,6R,7S)-5-[(R)-1-Hydroxyethyl]-9-iminomethyl-4-oxo-3,9-diazatricyclo[5.4.0.0$^{3,6}$]undec-1-ene-2-carboxylic acid

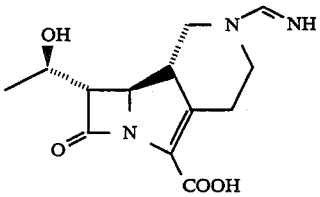

The compound synthesized in Example 30 was reacted in the same manner as in Example 29 to give the title compound.

IR (KBr): 3420, 1760, 1715, 1640, 1590 cm$^{-1}$ $^1$H-NMR(D$_2$O) δ: 1.30 (3H, d, J=6.4 Hz), 2.3–2.6 (1H, m), 3.1–3.6 (4H, m), 3.8–4.0 (1H, m), 3.82 and 3.87 (each 0.5H, dd, J=3.0 & 7.4 Hz), 4.0–4.2 (1H, dd, J=5.8 & 14.0 Hz), 4.21 and 4.22 (each 0.5H, quintet, J=6.4 Hz), 4.36 (1H, dd, J=5.8 & 12.8 Hz), 7.87 and 7.89 (each 0.5H s)

EXAMPLE 34

(5S,6R,7R)-5-[(R)-1-Hydroxyethyl]-9-iminomethyl-4-oxo-3,9-diazatricyclo[5.4.0.0$^{3,6}$]undec-1-ene-2-carboxylic acid

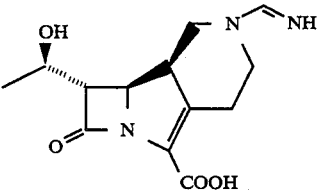

The compound synthesized in Example 31 was reacted in the same manner as in Example 28 to give the title compound.

IR (KBr): 3350, 1780, 1710, 1580 cm$^{-1}$ $^1$H-NMR(D$_2$O) δ: 1.28 and 1.29 (each 1.5H, d, J=6.4 Hz), 2.3–2.6 (1H m), 3.0–3.6 (5H, m), 3.9–4.3 (4H, m), 7.86 and 7.92 (each 0.5H, s)

EXAMPLE 35

(5S,6R,7S)-5-[(R)-1-Hydroxyethyl]-9-(1iminoethyl)-4-oxo-3,9-diazatricyclo[5.4.0.0$^{3,6}$]undec-1-ene-2-carboxylic acid The compound synthesized in Example 30 was reacted in the same manner as in Example 27 to give the title compound.

IR (KBr): 3400, 1760, 1680, 1625, 1580 cm$^{-1}$ $^1$H-NMR(D$_2$O) δ: 1.30 (3H, d, J=6.4 Hz), 2.3–2.6 (1H, m), 2.37 (3H, s), 3.1–3.4 (4H, m), 3.46 and 3.47 (each 0.5H, dd, J=2.8 & 5.8 Hz), 3.84 and 3.87 (each 0.5H, dd, J=2.8 & 5.4 Hz), 4.0–4.5 (2H, m), 4.25 (1H, dq, J=6.4 & 5.8 Hz)

EXAMPLE 36

Allyl (5S,6S,7RS)-5-[(R)-1-(trimethylsilyloxy)-ethyl]-4-oxo-9-oxa-3-azatricyclo[5.4.0.0$^{3,6}$]undec-1ene-2-carboxylate

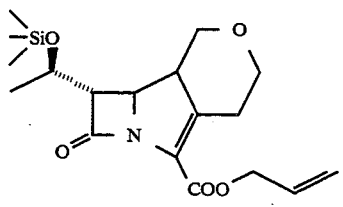

The title compound was synthesized in the same manner as in Example 8.

IR (KBr): 2980, 2950, 2860, 1770, 1745, 1725, 1660 cm$^{-1}$ $^1$H-NMR(CDCl$_3$) δ: 0.13 (9H, s), 1.26 (3H, m), 2.32–2.57 (1H, m), 3.04–3.64 (7H, m), 4.08–4.34 (2H, m), 4.64–4.88 (2H, m), 5.24–5.48 (2H, m), 5.94 (1H, m)

EXAMPLE 37

Sodium (5S,6S,7R)-5-[(R)-1-hydroxyethyl]-4-oxo-8,11-dithia-3-azatricyclo[5.4.0.0$^{3,6}$]undec-1-ene-2-carboxylate

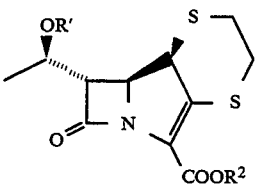

The following compounds were synthesized in the same manner as in Example 8.

(1) Allyl (5S,6S,7R)-5-[(R)-1-(trimethylsilyloxy)ethyl]-4-oxo-8,11-dithia-3-azatricyclo[5.4.0.0$^{3,6}$]undec-1-ene-2-carboxylate (R$^1$=SiMe$_3$, R$^2$=CH$_2$CH=CH$_2$)

IR (KBr): 2960, 2890, 1777, 1698, 1643, 1563 cm$^{-1}$ 1H-NMR (CDCl$_3$) δ: 0.13 (9H, s), 1.22 (3H, d, J=6.2 Hz), 2.92–3.20 (3H, m), 3.34–3.44 (1H, m), 3,58 (1H, ddd, J=5.2 Hz, 2.2 Hz, 0.6 Hz) 4.24 (1H, qd, J=6.2 Hz, 5.2 Hz), 4.40 (1H, dd, J=10.0 Hz, 2.2 Hz), 4.43 (1H, d, J=10.0 Hz), 4.65–4.88 (2H, m), 5.25 (1H, ddd J=10.6 Hz, 2.6 Hz, 1.2 Hz), 5.47 (1H, ddd, J=17.2 Hz, 3.0 Hz, 1.6 Hz), 5.97 (1H, ddt, J=17.2 Hz, 10.6 Hz, 5.6 Hz).

(2) Allyl (5S,6S,7R)-5-[(R)-1-hydroxyethyl]-4-oxo-8,11-dithia-3-azatricyclo[5.4.0.0$^{3,6}$]undec-1-ene-2-carboxylate (R$^1$=H, R$^2$CH$_2$CH=CH$_2$)

IR (KBr): 3360, 3300, 2980, 2930, 1783, 1705, 1648, 1550, 1518 cm$^{-1}$ $^1$H-NMR (CDCl$_3$) δ: 1.32 (3H, d, J=6.4 Hz), 1.88 (1H, d, J=5.0 Hz), 2.96–3.22 (3H, m), 3.33–3.52 (1H, m), 3.61 (1H, ddd, J=5.8 Hz, 2.0 Hz, 1.0 Hz), 4.18–4.34 (1H, m), 4.46 (1H, dd, J=10.0 Hz, 2.0 Hz), 4.48 (1H, d, J=10.0 Hz), 4.72 (1H, ddt, J=13.4 Hz, 5.6 Hz, 1.4 Hz), 4.84 (1H, ddt, J=13.4 Hz, 5.6 Hz, 1.4 Hz), 5.27 (1H, ddd, J=10.6 Hz, 2.8 Hz, 1.4 Hz), 5.46 (1H, ddd, J=17.2 Hz, 2.8 Hz, 1.4 Hz), 5.98 (1H, ddt, J=17.2 Hz, 10.6 Hz, 5.6 Hz)

(3) Title compound (R$^1$=H, R$^2$=Na)

IR (KBr): 3410, 2960, 2920, 1760, 1595, 1560, 1390 cm$^{-1}$ $^1$H-NMR(D$_2$O) δ: 1.28 (3H, d, J=6.6 Hz), 2.95–3.28 (3H, m), 3.38–3.52 (1H, m), 3.58 (1H, dd, J=5.6 Hz, 3.0 Hz), 4.26 (1H, qd, J=6.6 Hz, 5.6 Hz), 4.45 (1H, dd, J=9.8 Hz, 3.0 Hz), 4.62 (1H, d, J=9.8 Hz)

EXAMPLE 38

Sodium (5S,6S,7S)-5-[(R)-1-hydroxyethyl]4-oxo-8,11-dithia-3-azatricyclo[5.4.0.0$^{3,6}$]undec-1-ene-2-carboxylate

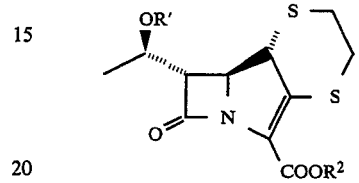

The following compounds were synthesized in the same manner as in Example 8.

(1) Ally (5S,6S,7S)-5-[(R)1-(trimethylsilyloxy)ethyl]-4-oxo-8,11-dithia-3-azatricyclo[5.4.0.0$^{3,6}$]undec-1-ene-2-carboxylate (R$^1$=SiMe$_3$, R$^2$=CH$_2$CH=CH$_2$)

IR(Neat): 2950, 1780, 1710, 1647, 1560 cm$^{-1}$ $^1$H-NMR(CDCl$_3$) δ: 0.14 (9H, s), 1.27 (3H, d, J=6.0 Hz), 2.88–3.20 (4H, m), 3.26 (1H, dd, J=7.0 Hz, 2.8 Hz), 3.82 (1H, dd, J=8.0 Hz, 2.8 Hz), 4.24 (1H, dq, J=7.0 Hz, 6.0 Hz), 4.34 (1H, d, J=8.0 Hz), 4.65–4.89 (2H, m), 5.21–5.31 (1H, m), 5.38–5.52 (1H, m), 5.82–6.07 (1H, m)

(2) Allyl (5S,6S,7S)-5-[(R)-1-hydroxyethyl]-4-oxo-8,11-dithia-3-azatricyclo[5.4.0.0$^{3,6}$]undec-1-ene-2-carboxylate (R$^1$=H, R$^2$=CH$_2$CH=CH$_2$)

IR(Neat): 3450, 2960, 2925, 1780, 1713, 1650, 1560 cm$^{-1}$ $^1$H-NMR(CDCl$_3$) δ: 1.34 (3H, d, J=6.4 Hz), 1.89 (1H, d, J=4.4 Hz), 2.89–3.29 (4H, m), 3.32 (1H, dd, J=6.0 Hz, 2.8 Hz), 3.91 (1H, dd, J=8.0 Hz, 2.8 Hz), 4.18–4.31 (1H, m), 4.36 (1H, d, J=8.0 Hz, 4.72 Hz), 4.72 (1H, ddt, J=13.4 Hz, 5.6 Hz, 1.4 Hz), 4.83 (1H, ddt, J=13.4 Hz, 5.6 Hz, 1.4 Hz), 5.27 (1H, ddd, J=10.4 Hz, 2.8 Hz, 1.4 Hz), 5.45 (1H, ddd, J=17.2 Hz, 2.8 Hz, 1.4 Hz), 5.97 (1H, ddt, J=17.2 Hz, 10.4 Hz, 5.6 Hz)

(3) Title compound (R$^1$=H, R$^2$=Na)

IR(KBr): 3425, 2960, 2920, 1760, 1600, 1560, 1390 cm$^{-1}$ $^1$H-NMR(D$_2$O) δ: 1.28 (3H, d, J=6.4 Hz ), 2.90–3.35 (4H, m), 3.60 (1H, dd, J=5.8 Hz, 2.8 Hz), 3.87 (1H, dd, J=7.6 Hz, 2.8 Hz), 4.25 (1H, qd, J=6.4 Hz, 5.8 Hz), 4.60 (1H, d, J=7.6 Hz)

EXAMPLE 39

Sodium (5S,6S,7R)-5-[(R)-1-hydroxyethyl]-4-oxo-8-oxa-11-thia-3-azatricyclo[5.4.0.0$^{3,6}$]undec-1-ene-2-carboxylate

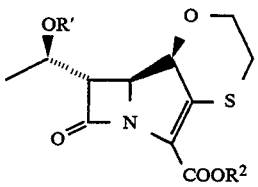

The following compounds were synthesized in the same manner as in Example 8.

(1) Allyl (5S,6S,7R)-5-[(R)-1-(trimethylsilyloxy)ethyl]-4-oxo-8-oxa-11-thia-3-azatricyclo-5.4.0.0³,⁶]undec-1-ene-2-carboxylate (R¹=SiMe₃, R²=CH₂CH=CH₂)

IR (KBr): 2960, 2890, 1772, 1695, 1640, 1575 cm⁻¹
¹H-NMR (CDCl₃) δ: 0.14 (9H, s), 1.20 (3 H, d, J=6.2 Hz), 2.80-3.02 (2H, m), 3.70 (1H, t, J=4.0 Hz), 4.18-4.29 (3H, m), 4.32 (1H, dd, J=9.6 Hz, 4.0 Hz), 4.66-4.88 (2H, m), 4.77 (1H, d, J=9.6 Hz), 5.27 (1H, ddd, J=10.6 Hz, 2.8 Hz, 1.4 Hz), 5.48 (1H, ddd, J=17.2 Hz, 3.2 Hz, 1.4 Hz), 5.98 (1H, ddt, J=17.2 Hz, 10.6 Hz)

(2) Allyl (5S,6S,7R)-5-[(R)-1-hydroxyethyl]-4-oxo-8-oxa-11-thia-3-azatricyclo[5.4.0.0³,⁶]undec-1-ene-2-carboxylate IR (KBr): 3530, 2965, 2940, 2920, 2880, 1765, 1693, 1643, 1577 cm⁻¹ ¹H-NMR(CDCl₃) δ: 1.31 (3H, d, J=6.4 Hz), 1.84 (1H, d, J=5.0 Hz), 2.80-3.06 (2H, m ), 3.75 (1H, dd, J=6.0 Hz, 4.0 Hz ), 4.15-4.36 (3H, m), 4.33 (1H, dd, J=9.2 Hz, 4.0 Hz), 4.74 (1H, ddt, J=13.4 Hz, 5.6 Hz, 1.4 Hz), 4.82 (1H, d, J=9.2 Hz), 4.83 (1H, ddt, J=13.4 Hz, 5.6 Hz, 1.4 Hz), 5.28 (1H, ddd, J=10.6 Hz, 2.8 Hz), 1.4 Hz), 5.46 (1H, ddd, J=17.2 Hz, 2.8 Hz, 1.4 Hz), 5.98 (1H, ddt, J=17.2 Hz, 10.6 Hz, 5.6 Hz)

(3) Title compound (R¹=H, R²=Na)

IR (KBr): 3410, 2960, 2925, 2860, 1780, 1610, 1400 cm⁻¹ ¹H-NMR (D₂O) δ: 1.27 (3H, d, J=6.4 Hz), 2.84-3.10 (2H, m), 3.71 (1H, dd, J=5.2 Hz, 3.8 Hz), 4.20-4.30 (3H, m), 4.34 (1H, dd, J=9.0 Hz, 3.8 Hz ), 4.92 (1H, d, J=9.0 Hz )

EXAMPLE 40

Sodium (5S,6S,7S)-5-[(R)-1-hydroxyethyl]-4-oxo-8-oxa-11-thia-3-azatricyclo[5.4.0.0³,⁶]undec-1-ene-2-carboxylate

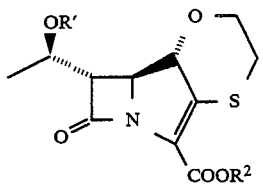

The following compounds were synthesized in the same manner as in Example 8.

(1) Allyl (5S,6S,7S)-5-[(R)-1-(trimethylsilyloxy)ethyl]-4-oxo-8-oxa-11-thia-3-azatricyclo-[5.4.0.0³,⁶]undec-1-ene-2-carboxylate (R¹=SiMe₃, R²=CH₂CH=CH₂)

IR(Neat):2955, 2865, 1780, 1718, 1645, 1565 cm⁻¹
¹H-NMR(CDCl₃) δ: 0.14 (9H, s), 1.29 (3H, d, J=6.2 Hz), 2.51 (1H, dt, J=13.0 Hz, 2.6 Hz), 3.03 (1H, ddd, J=13.0 Hz, 11.4 Hz, 3.8 Hz), 3.18 (1H, dd, J=6.6 Hz, 2.8 Hz), 3.85-4.00 (2H, m), 4.20 (1H, dq, J=6.2 Hz, 4.4 Hz), 4.33 (1H, ddd, J=12.4 Hz, 3.8 Hz, 2.8 Hz), 4.64-4.88 (2H, m), 4.82 (1H, d, J=7.8 Hz), 5.26 (1H, ddd, J=10.2 Hz, 2.8 Hz, 1.4 Hz), 5.45 (1H, ddd, J=17.2 Hz, 2.8 Hz, 1.4 Hz), 5.96 (1H, ddt, J=17.2 Hz, 10.2 Hz, 5.4 Hz)

(2) Allyl (5S,6S,7S)-5-[(R)-1-hydroxyethyl]-4-oxo-8-oxa-11-thia-3-azatricyclo[5.4.0.0³,⁶]undec-1-ene-2-carboxylate (R¹=H, R²=CH₂CH=CH₂)

IR(Neat): 3440, 2975, 2945, 2900, 2850, 1780, 1715, 1650, 1568 cm⁻¹ ¹H-NMR(CDCl₃) δ: 1.37 (3H, d, J=6.4 Hz), 1.94 (1H, d, J=4.6 Hz), 2.53 (1H, dt, J=13.2 Hz, 2.8 Hz), 3.04 (1H, ddd, J=13.0 Hz, 11.6 Hz, 3.8 Hz), 3.24 (1H, dd, J=6.6 Hz, 2.6 Hz), 3.95 (1H, ddd, J=12.4 Hz, 11.6 Hz, 2.6 Hz), 4.00 (1H, dd, J=7.8 Hz, 2.6 Hz), 4.18-4.33 (1H, m), 4.34 (1H, ddd, J=12.4 Hz, 4.0 Hz, 2.6 Hz), 1.4 Hz), 4.85 (1H, d, J=7.8 Hz), 5.28 (1H, ddd, J=10.4 Hz, 2.8 Hz, 1.4 Hz), 5.45 (1H, ddd, J=17.2 Hz, 2.8 Hz, 1.4 Hz), 5.97 (1H, ddt, J=17.2 Hz, 10.4 Hz, 5.6 Hz)

(3) Title compound (R¹=H, R²=Na)

IR (KBr): 3420, 2960, 2920, 2855, 1760, 1603, 1395 cm⁻¹ ¹H-NMR(D₂O) δ: 1.30 (3H, d, J=6.4 Hz), 2.64 (1H, dt, J=13.4 Hz, 2.6 Hz), 3.00 (1H, ddd, J=13.4 Hz, 11.4 Hz, 3.8 Hz), 3.53 (1H, dd, J=5.4 Hz, 2.6 Hz), 3.92-4.07 (2H, m), 4.27 (1H, qd, J=6.4 Hz, 5.4 Hz), 4.36 (1H, ddd, J=12.4 Hz, 3.8 Hz, 2.6 Hz), 5.01 (1H, d, J=5.2 Hz)

We claim:
1. A compound of the formula

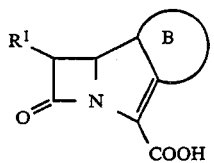

wherein R¹ is (1) a hydrogen atom or (2) C₁₋₆ alkyl, C₃₋₆ alkenyl, C₃₋₆ alkynyl, C₃₋₆ cycloalkyl, C₇₋₁₀ aralkyl or C₆₋₁₀ aryl, the substituent (2) optionally being substituted by 1 to 3 substituents, which may be the same or different, selected from the group consisting of cyano, amino, mono- or di(C₁₋₄)alkylamino, hydroxy, (C₁₋₄)alkyloxy, carbamoyloxy, (C₁₋₄)alkylthio, (C₁₋₄)alkylsulfonyl, halogen, sulfamoyl, (C₁₋₄)alkoxycarbonyl and sulfoxy; and ring B is five- to seven-membered heterocyclic ring containing one or two hetero atom(s) of S, O and N as the ring constituent atom, and may be substituted by 1 to 3 substituents, which are the same or different, selected from the group consisting of (1) C₁₋₆ alkyl which may be substituted by 1 to 3 substituents, which are the same or different, selected from the group consisting of four- to six-membered heterocyclic group having 1 to 4 hetero atoms selected from N, O and S, cyano, amino, mono- or di(C₁₋₄)alkylamino, hydroxy, (C₁₋₄)alkyloxy, carbamoyloxy, (C₁₋₄)alkylthio, (C₁₋₄)alkylsulfonyl, halogen, sulfamoyl, (C₁₋₄)alkoxycarbonyl, imino, (C₁₋₄)alkylimino, carbamoyl and mono- or di(C₁₋₄)alkylcarbamoyl, (2) C₂₋₆ alkenyl, (3) C₆₋₁₀ aryl, (4) C₇₋₁₂ aralkyl, (5) C₃₋₆ cycloalkyl, (6) four- to six-membered heterocyclic group having 1 to 4 hetero atoms selected from N, O and S, (7) cyano, (8) amino, (9) mono- or di(C₁₋₄)alkylamino, (10) hydroxy, (11) (C₁₋₄)alkyloxy, (12) carbamoyloxy (13), (C₁₋₄) alkylthio, (14) (C₁₋₄)alkylsulfonyl, (15) halogen, (16) sulfamoyl, (17) (C₁₋₄)alkoxycarbonyl, (18) imino, (19) (C₁₋₄)alkylimino, (20) carbamoyl and (21) mono- or di(C₁₋₄)alkylcarbamoyl, or a pharmaceutically acceptable salt or ester thereof.

2. A compound of the formula

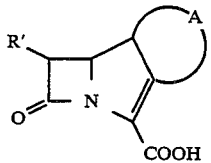

wherein $R^1$ is (1) a hydrogen atom or (2) $C_{1-6}$ alkyl, $C_{3-6}$ alkenyl, $C_{3-6}$ alkynyl, $C_{3-6}$ cycloalkyl, $C_{7-10}$ aralkyl or $C_{6-10}$ aryl, the substituent (2) optionally being substituted by 1 to 3 substituents, which may be the same or different, selected from the group consisting of cyano, amino, mono- or di($C_{1-4}$)alkylamino, hydroxy, ($C_{1-4}$)alkyloxy, carbamoyloxy, ($C_{1-4}$)alkylthio, ($C_{1-4}$)alkylsulfonyl, halogen, sulfamoyl, ($C_{1-4}$)alkoxycarbonyl and sulfoxy; and A is a lower alkylene or lower alkenylene group which has 1 to 4 hetero atoms of an oxygen atom, sulfur atom optionally oxidized and nitrogen atom, carbonyl group or carbonimidoyl group as the ring constituent element, and A may be further condensed with a cyclic hydrocarbon group selected from the group consisting of cyclopropane, cyclopentane, cyclohexane, cyclopentene, cyclohexene, benzene and naphthalene, or a heterocyclic group having 1 to 4 hetero atoms selected from N, O and S, and the optionally condensed group A may be substituted by 1 to 3 substituents, which are the same or different, selected from the group consisting of (1) $C_{1-6}$ alkyl which may be substituted by 1 to 3 substituents, which are the same or different, selected from the group consisting of four- to six-membered heterocyclic group having 1 to 4 hetero atoms selected from N, O and S, cyano, amino, mono- or di($C_{1-4}$)alkylamino, hydroxy, ($C_{1-4}$)alkyloxy, carbamoyloxy, ($C_{1-4}$)alkylthio, ($C_{1-4}$)alkylsulfonyl, halogen, sulfamoyl, ($C_{1-4}$)alkoxycarbonyl, imino, ($C_{1-4}$)alkylimino, carbamoyl and mono- or di($C_{1-4}$)alkylcarbamoyl, (2) $C_{2-6}$ alkenyl, (3) $C_{6-10}$ aryl, (4) $C_{7-12}$ aralkyl, (5) $C_{3-6}$ cycloalkyl, (6) four- to six-membered heterocyclic group having 1 to 4 hetero atoms selected from N, O and S, (7) cyano, (8) amino, (9) mono- or di($C_{1-4}$)alkylamino, (10) hydroxy, (11) ($C_{1-4}$)alkyloxy, (12) carbamoyloxy, (13) ($C_{1-4}$)alkylthio, (14) ($C_{1-4}$)alkylsulfonyl, (15) halogen, (16) sulfamoyl, (17) ($C_{1-4}$)alkoxycarbonyl, (18) imino, (19) ($C_{1-4}$)alkylimino, (20) carbamoyl and (21) mono- or di($C_{1-4}$)alkylcarbamoyl, or a pharmaceutically acceptable salt or ester thereof.

3. The compound which is (5S,6S,7S)-5-[(R)-1-hydroxyethyl]-4-oxo-8-oxa-3-azatricyclo[5.4.0.0$^{3,6}$]-undec-1-2-carboxylic acid 4. The compound which is (5S,6R,7R)-5-[(R)-1-hydroxyethyl]-9-iminomethyl-4-oxo-3,9-diazatricyclo[5.4.0.0$^{3,6}$]undec-1-ene-2-carboxylic acid.

5. (10S,11R,12S)-5-(2-Aminoethoxy)-12-[(R)-1-hydroxyethyl]-13-oxo-14-azatetracyclo[8.5.0.0$^{2,7}$.0$^{11,14}$]pentadeca-2,4,6,15 (1)-tetraene-15-carboxylic acid, or a pharmaceutically acceptable salt or ester thereof.

6. (10S,11R,12S)-5-[2-(1-Iminoethyl)amino]ethoxy]-12-[(R)-1-hydroxyethyl]-13-oxo-14-azatetracyclo[8.5.0.0$^{2,7}$.0$^{11,14}$]pentadeca-2,4,6,15 (1)-tetraene-15-carboxylic acid, or a pharmaceutically acceptable salt or ester thereof.

7. (10S,11R,12S)-5-[2-(Iminomethylamino)ethoxy]-12-[(R)-1-hydroxyethyl]-13-oxo-14-azatetracyclo[8.5.0.0$^{2,7}$.0$^{11,14}$]-pentadeca-2,4,6,15(1)-tetraene-15-carboxylic acid, or a pharmaceutically acceptable salt or ester thereof.

* * * * *